(12) United States Patent
Xu

(10) Patent No.: US 8,329,897 B2
(45) Date of Patent: Dec. 11, 2012

(54) SYNTHESIS OF INHIBITORS OF 11β-HYDROXYSTEROID DEHYDROGENASE TYPE 1

(75) Inventor: Zhenrong Xu, Horsham, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 207 days.

(21) Appl. No.: 12/670,209

(22) PCT Filed: Jul. 25, 2008

(86) PCT No.: PCT/US2008/009048
§ 371 (c)(1),
(2), (4) Date: Jun. 15, 2010

(87) PCT Pub. No.: WO2009/017671
PCT Pub. Date: Feb. 5, 2009

(65) Prior Publication Data
US 2010/0256363 A1    Oct. 7, 2010

Related U.S. Application Data

(60) Provisional application No. 60/962,058, filed on Jul. 26, 2007, provisional application No. 61/001,253, filed on Oct. 31, 2007, provisional application No. 61/049,650, filed on May 1, 2008.

(51) Int. Cl.
| C07D 265/10 | (2006.01) |
|---|---|
| C07D 413/04 | (2006.01) |
| C07D 413/06 | (2006.01) |
| C07D 413/10 | (2006.01) |
| C07D 413/14 | (2006.01) |

(52) U.S. Cl. .................................... 544/96; 544/97
(58) Field of Classification Search ............. 544/96
See application file for complete search history.

(56) References Cited

U.S. PATENT DOCUMENTS

| 3,341,538 A | 9/1967 | Block et al. |
|---|---|---|
| 3,681,349 A | 8/1972 | Schwan et al. |
| 4,136,145 A | 1/1979 | Fuchs et al. |
| 4,136,162 A | 1/1979 | Fuchs et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 7,026,310 B2 | 4/2006 | Emig et al. |
| 7,056,912 B2 | 6/2006 | Emig et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |

(Continued)

FOREIGN PATENT DOCUMENTS

DE    1801556 A1    5/1970

(Continued)

OTHER PUBLICATIONS

International Search Report—(PCT/US2010/023021) Date of Mailing Aug. 5, 2010. Database CA [Online], Chemical Abstracts Service, Fukushima et al., "Preparation of Imidazolidinone Derivatives as 11.beta.-HSD1 Inhibitors", 2007, XP 002531878.
Gavezzotti, "Are Crystal Structures Predictable?", Accounts of Chemical Research, 1994, vol. 27, pp. 309-314.
Vippagunta, et al., "Crystalline Solids", Advanced Drug Deliver Reviews, 2001, vol. 48, pp. 3-26.
U.S. Appl. No. 12/670,205, filed Jul. 25, 2008, Vitae Pharmaceuticals, Inc.
U.S. Appl. No. 12/741,522, filed Apr. 30, 2009, Vitae Pharmaceuticals, Inc.
U.S. Appl. No. 12/990,309, filed Apr. 30, 2009, Vitae Pharmaceuticals, Inc.
U.S. Appl. No. 12/990,296, filed Apr. 30, 2009, Vitae Pharmaceuticals, Inc.

(Continued)

Primary Examiner — Kahsay T Habte
(74) Attorney, Agent, or Firm — McCarter & English, LLP; Steven G. Davis; Michael DeGrazia

(57) ABSTRACT

Disclosed are syntheses of 11β-HSD1 inhibitors and corresponding intermediates that are promising for the treatment of a variety of disease states including diabetes, metabolic syndrome, obesity, glucose intolerance, insulin resistance, hyperglycemia, hypertension, hypertension-related cardiovascular disorders, hyperlipidemia, deleterious gluco-corticoid effects on neuronal function (e.g. cognitive impairment, dementia, and/or depression), elevated intra-ocular pressure, various forms of bone disease (e.g., osteoporosis), tuberculosis, leprosy (Hansen's disease), psoriasis, and impaired wound healing (e.g., in patients that exhibit impaired glucose tolerance and/or type 2 diabetes).

17 Claims, 2 Drawing Sheets

U.S. PATENT DOCUMENTS

| | | | |
|---|---|---|---|
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0124384 A1 | 5/2008 | Blum |
| 2008/0188482 A1 | 8/2008 | Rice et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0264650 A1 | 10/2009 | Cho et al. |
| 2010/0041637 A1 | 2/2010 | Claremon et al. |
| 2010/0197675 A1 | 8/2010 | Claremon et al. |

FOREIGN PATENT DOCUMENTS

| | | |
|---|---|---|
| DE | 19918725 A1 | 10/2000 |
| DE | 19929348 A1 | 12/2000 |
| DE | 100 34 623 | 1/2002 |
| DE | 10034623 | 1/2002 |
| EP | 0415642 A1 | 3/1991 |
| EP | 0454444 A1 | 10/1991 |
| EP | 0640594 A1 | 3/1995 |
| EP | 0645387 A | 3/1995 |
| EP | 0471591 B1 | 5/1995 |
| EP | 0928789 A1 | 7/1999 |
| EP | 1156049 A | 11/2001 |
| EP | 1270724 A2 | 1/2003 |
| EP | 1852425 A | 11/2007 |
| EP | 1864971 A | 12/2007 |
| EP | 1935420 | 6/2008 |
| GB | 1077711 | 8/1967 |
| JP | 6092945 A | 4/1994 |
| JP | 7157681 | 6/1995 |
| JP | 2009110842 A2 | 4/1997 |
| JP | 09151179 | 6/1997 |
| JP | 2002179572 A2 | 6/2002 |
| JP | 2003096058 | 4/2003 |
| JP | 2003300884 A2 | 10/2003 |
| JP | 2005-206503 A | 8/2005 |
| JP | 2005239670 | 9/2005 |
| JP | 2005272321 A | 10/2005 |
| JP | 2007 140188 | 6/2007 |
| JP | 2007 254409 | 10/2007 |
| WO | WO 92/07838 | 5/1992 |
| WO | WO 93/07128 | 4/1993 |
| WO | WO 93/13103 | 7/1993 |
| WO | WO 95/31440 | 11/1995 |
| WO | WO 96/14297 A | 5/1996 |
| WO | WO 96/23787 | 8/1996 |
| WO | WO 97/36605 | 10/1997 |
| WO | WO 98/57940 | 12/1998 |
| WO | WO 99/05125 | 2/1999 |
| WO | WO 99/06395 | 2/1999 |
| WO | WO 01/00595 A1 | 1/2001 |
| WO | WO 01/44200 A2 | 6/2001 |
| WO | WO 01/55063 | 8/2001 |
| WO | WO 02/06244 A1 | 1/2002 |
| WO | WO 02/06277 A1 | 1/2002 |
| WO | WO 02/22572 A2 | 3/2002 |
| WO | WO 03/043988 A1 | 5/2003 |
| WO | WO 03/057673 A | 7/2003 |
| WO | WO 03/093261 A1 | 11/2003 |
| WO | WO 2004/004722 A1 | 1/2004 |
| WO | WO 2004/009559 A2 | 1/2004 |
| WO | WO 2004/014859 A2 | 2/2004 |
| WO | WO 2004/094375 A | 11/2004 |
| WO | WO 2005/000845 | 1/2005 |
| WO | WO 2005/086700 A2 | 9/2005 |
| WO | WO 2005/108361 | 11/2005 |
| WO | WO 2005/108361 A | 11/2005 |
| WO | WO 2005/113525 A1 | 12/2005 |
| WO | WO 2006/003494 A2 | 1/2006 |
| WO | WO 2006/014357 A | 2/2006 |
| WO | WO 2006/024627 A2 | 3/2006 |
| WO | WO 2006/024628 A | 3/2006 |
| WO | WO 2006/031715 A | 3/2006 |
| WO | WO 2006/040329 | 4/2006 |
| WO | WO 2006/044174 | 4/2006 |
| WO | WO 2006/049952 A | 5/2006 |
| WO | WO 2006/066924 A2 | 6/2006 |
| WO | WO 2006/066948 A1 | 6/2006 |
| WO | WO 2006/090792 A1 | 8/2006 |
| WO | WO 2006/104280 A | 10/2006 |
| WO | WO 2007/008529 A2 | 1/2007 |
| WO | WO 2007/051810 | 5/2007 |
| WO | WO 2007/061661 A2 | 5/2007 |
| WO | WO 2007/068330 A1 | 6/2007 |
| WO | WO 2007/079186 A2 | 7/2007 |
| WO | WO 2007/081569 A2 | 7/2007 |
| WO | WO 2007/081570 A | 7/2007 |
| WO | WO2007/081571 A2 | 7/2007 |
| WO | WO 2007/084314 A2 | 7/2007 |
| WO | WO 2007/109456 A2 | 9/2007 |
| WO | WO 2007/118185 A2 | 10/2007 |
| WO | WO 2007/124254 | 11/2007 |
| WO | WO 2007/124329 A | 11/2007 |
| WO | WO 2007/124337 | 11/2007 |
| WO | WO 2007/127693 A | 11/2007 |
| WO | WO 2008/000951 | 1/2008 |
| WO | WO 2008/031227 A1 | 3/2008 |
| WO | WO 2008/036715 A1 | 3/2008 |
| WO | WO 2008/046758 A | 4/2008 |
| WO | WO 2008/059948 A | 5/2008 |
| WO | WO 2008/106128 | 9/2008 |
| WO | WO 2008/106128 A | 9/2008 |
| WO | WO 2008/118332 A2 | 10/2008 |
| WO | WO 2009/017664 | 2/2009 |
| WO | WO 2009/017664 A1 | 2/2009 |
| WO | WO 2009/017671 | 2/2009 |
| WO | WO 2009/061498 | 5/2009 |
| WO | WO 2009/063061 | 5/2009 |
| WO | WO 2009/075835 | 6/2009 |
| WO | WO 2009/088997 | 7/2009 |
| WO | WO 2009/094169 A | 7/2009 |
| WO | WO 2009/100872 | 8/2009 |
| WO | WO 2009/102428 | 8/2009 |
| WO | WO 2009/102460 | 8/2009 |
| WO | WO 2009/117109 | 9/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | WO 2010/010149 | 1/2010 |
| WO | WO 2010/010157 | 1/2010 |
| WO | WO 2010/010174 | 1/2010 |
| WO | WO 2010/011314 | 1/2010 |
| WO | WO 2010/023161 | 3/2010 |
| WO | WO 2010/046445 | 4/2010 |
| WO | WO 2010/091067 | 8/2010 |
| WO | WO 2010/127237 | 11/2010 |

OTHER PUBLICATIONS

U.S. Appl. No. 12/745,663, filed Nov. 7, 2008, Vitae Pharmaceuticals, Inc.

U.S. Appl. No. 12/811,577, filed Jan. 7, 2009, Vitae Pharmaceuticals, Inc.

U.S. Appl. No. 12/747,391, filed Dec. 10, 2008, Vitae Pharmaceuticals, Inc.

U.S. Appl. No. 12/863,634, filed Jan. 21, 2009, Vitae Pharmaceuticals, Inc.

U.S. Appl. No. 12/867,374, filed Feb. 13, 2009, Vitae Pharmaceuticals, Inc.
U.S. Appl. No. 12/933,027, filed Mar. 18, 2009, Vitae Pharmaceuticals, Inc.
U.S. Appl. No. 12/741,532, filed Sep. 27, 2010, Vitae Pharmaceuticals, Inc.
U.S. Appl. No. 12/771,499, filed Apr. 30, 2010, Vitae Pharmaceuticals, Inc.
International Search Report and Written Opinion—(PCT/US2008/009048) Date of Mailing Dec. 4, 2008.
International Search Report—(PCT/US2009/004261) Date of Mailing Oct. 21, 2009.
Shibata, et al., "Cycloaddition of Oxetanes with Heterocumulenes Catalysed by Organotin Iodine-Lewis Base Complex", Journal of Heterocyclic Chemistry, vol. 24, 1987, pp. 361-363.
MS Bitar, "Glucocorticoid Dynamics and Impaired Wound Healing in Diabetes Mellitus", Am J Pathol., 1998, vol. 152, pp. 547-554.
MS Bitar, et al., "Heat-Shock Protein 72/73 and Impaired Wound Healing in Diabetic and Hypercortisolemic States", Sugery, 1999, vol. 125, pp. 594-601.
MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.
MS Bitar, "Insulin and Glucocorticoid-Dependent Suppression of the IGF-I System in Diabetic Wounds", Surgery, 2000, vol. 127, pp. 687-695.
Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CAS RN: 20057-45-8 abstract.
Chimica Therapeutica, 1968, vol. 3(5), pp. 321-324, 1968.
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract.
Zhurnal Organicheskoi Khimii, 1978, vol. 14(5), pp. 1092-1094.
Database CA [Online], Chemical Abstracts Service, Fukushima et al., "Preparation of Imidazolidinone Derivatives as 11.beta.-HSD1 Inhibitors", XP 002531878.
"Khimila Elementoorganicheskikh Soedineni", 1982, vol. 1982 pp. 22-26.
"Zhurnal Organicheskoi Khimii", 1982, vol. 18, PT 11, p. 2468.
Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063 abstract.
Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract.
Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.
Ho-Jane Shue et al., "Cyclic Urea Derivatives as Potent NK1 Selective Antagonists", Bioorganic & Medicinal Chemistry Letters, 2005, vol. 15, pp. 3896-3899.
Ho-Jane Shue et al., "Cyclic Urea Derivatives as Potent NK1 Selective Antagonists, Part II: Effects of Fluoro and Benzylic Methyl Substitutions", Bioorganic & Medicinal Chemistry Letters, 2006, vol. 16, pp. 1065-1069.
Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Malgorzata Wamil and Jonathan R. Seckl, "Inhibition of 11β-hydroxysteroid Dehydrogenase Type 1 as a Promising Therapeutic Target", Drug Discovery Today, 2007, vol. 12, pp. 504-520.
Muehlstadt, et al., "Cyclisation reactions of beta, gamma-unsaturated derivatives of carbonic acid, IX.", Journal Fuer Praktische Chemie, vol. 328, 1986, pp. 163-172, XP002504062 p. 164, compound 4j.
Schoellkopf, et al., "Umsetzungen Alphametallierter Isocyanide Mit Einigen 1,3-Dipolen/Reactions of Alpha-Metalated Osicyanides with Some 1,3-Dipoles", Liebigs Annalen Der Chemie, Verlag Chemie GmbH. Weinheim, DE, 1980, vol. 4, pp. 600-610.
Suga, Seiji et al., ""N-Acyliminium Ion Pool" as a Heterodiene in [4+2] Cycloaddition Reaction", Organic Letters, 2003, vol. 5, pp. 945-947.
Suga, Seiji et al., "Cycloaddition of "N-Acyliminium Ion Pools" with Carbon-Carbon Multiple Bonds", Bulletin of the Chemical Society of Japan, Chemical Society of Japan, 2005, vol. 78, pp. 1206-1217.
Tamaru et al., "Urea as the Most Reactive and Versatile Nitrogen Nucleophile for the Palladium(2+)—Catalyzed Cyclization of Unsaturated Amines", Journal of the American Chemical Society, 1988, vol. 110, pp. 3994-4002.
Yoshida, Masaaki et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.
Yoshinao Tamaru, "Palladium(2+)-Catalyzed intramolecular Aminocarbonylation of 3-Hydroxy-4-pentenylamines and 4-Hydroxy-5-hexenylamines", J. Org. Chem., 1988, pp. 5731-5741.
International Search Report & Written Opinion—(PCT/US2008/009017) Date of Mailing Apr. 12, 2008.
International Search Report & Written Opinion—(PCT/US2008/002517) Date of Mailing Dec. 29, 2008.
International Search Report—(PCT/US2009/002653) Date of Mailing Jul. 3, 2009.
International Search Report—(PCT/US2009/002641) Date of Mailing Jul. 3, 2009.
International Search Report—(PCT/US2009/002629) Date of Mailing Jul. 3, 2009.
International Search Report—(PCT/US2009/002633) Date of Mailing Jul. 3, 2009.
International Search Report—(PCT/US2008/012618) Date of Mailing Dec. 3, 2009.
International Search Report—(PCT/US2009/000057) Date of Mailing Mar. 25, 2009.
International Search Report—(PCT/US2008/013539) Date of Mailing Mar. 19, 2009.
International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Columbus, Ohio, US, 2007, Database accession No. 958700-63-5, Abstract, XP002556893.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-14-6, Abstract, XP002556898.
Database File Registry [Online], Chemical Abstracts Service, Columbus, Ohio, US, 2007, Database accession No. 958625-83-7, Abstract, XP002556899.
Database File Registry [Online], Chemical Abstracts Service, Columbus, Ohio, US, 2007, Database accession No. 958599-31-0, Abstract, XP002556900.

SYNTHESIS OF INHIBITORS OF 11β-HYDROXYSTEROID DEHYDROGENASE TYPE 1

RELATED APPLICATIONS

The present application is a U.S. national stage application claiming the benefit of International Application No. PCT/US2008/009048, filed on Jul. 25, 2008, which claims the benefit of U.S. Provisional Application No. 60/962,058, filed on Jul. 26, 2007, U.S. Provisional Application No. 61/001,253, filed Oct. 31, 2007 and U.S. Provisional Application No. 61/049,650, filed May 1, 2008. The entire teachings of the above applications are incorporated herein by reference.

BACKGROUND OF THE INVENTION

Inhibitors of 11β-Hydroxysteroid Dehydrogenase Type 1 (11β-HSD1) are promising drugs for the treatment of a number of diseases and disorders as described in detail in U.S. Provisional Patent Application No. 60/962,058, filed Jul. 26, 2007; U.S. Provisional Patent Application No. 61/001,253, filed Oct. 31, 2007; U.S. Provisional Patent Application No. 61/049,650, filed May 1, 2008; and International Application No. PCT/US2008/009048, filed Jul. 25, 2008; all of which are herein incorporated by reference in their entirety.

For example, 11β-HSD1 inhibitors are promising for the treatment of diabetes, metabolic syndrome, obesity, glucose intolerance, insulin resistance, hyperglycemia, hypertension, hypertension-related cardiovascular disorders, hyperlipidemia, deleterious gluco-corticoid effects on neuronal function (e.g. cognitive impairment, dementia, and/or depression), elevated intra-ocular pressure, various forms of bone disease (e.g., osteoporosis), tuberculosis, leprosy (Hansen's disease), psoriasis, and impaired wound healing (e.g., in patients that exhibit impaired glucose tolerance and/or type 2 diabetes).

There is a need for better, for example, more economical and more efficient methods for synthesis of the 11β-HSD1 inhibitors.

SUMMARY OF THE INVENTION

The present invention provides economical and efficient methods for the synthesis of 11β-HSD1 inhibitors, for example, oxazinone compounds and tertiary alcohol oxazinone compounds as disclosed herein.

One embodiment of the present invention is a method of preparing an oxazinone compound represented by structural formula (I):

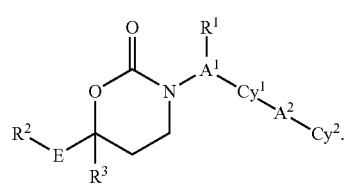

$R^1$ is (a) absent or (b) is selected from optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_3$)alkoxy($C_1$-$C_3$)alkoxy, and optionally substituted ($C_1$-$C_3$)alkoxy($C_1$-$C_3$)alkyl;

E is (a) a bond or (b) ($C_1$-$C_3$)alkylene or ($C_1$-$C_2$)alkoxy, wherein the O is attached to $R^2$, each of which is optionally substituted with 1 to 4 groups independently selected from methyl, ethyl, trifluoromethyl and oxo;

$R^2$ is selected from optionally substituted ($C_1$-$C_6$)alkyl, optionally substituted aryl, optionally substituted heteroaryl, optionally substituted cycloalkyl or optionally substituted heterocyclyl;

$R^3$ is selected from optionally substituted ($C_1$-$C_6$)alkyl, optionally substituted ($C_2$-$C_6$)alkenyl, optionally substituted ($C_2$-$C_6$)alkynyl, optionally substituted ($C_3$-$C_5$)cycloalkyl ($C_1$-$C_4$)alkyl, optionally substituted ($C_1$-$C_3$)alkoxy($C_1$-$C_3$) alkoxy and optionally substituted ($C_1$-$C_3$)alkoxy($C_1$-$C_3$) alkyl;

$A^1$ is (a) a bond, or (b) ($C_1$-$C_3$)alkylene, $CH_2CH_2O$, wherein the oxygen is attached to $Cy^1$;

$Cy^1$ is optionally substituted aryl, optionally substituted heteroaryl, optionally substituted monocyclic cycloalkyl or optionally substituted monocyclic heterocyclyl;

$A^2$ is (a) a bond, O, S or $NR^4$, wherein $R^4$ is ($C_1$-$C_3$)alkyl or ($C_3$-$C_6$)cycloalkyl; or (b) ($C_1$-$C_3$)alkylene or ($C_1$-$C_2$)alkoxy, each of which is optionally substituted with 1 to 4 groups independently selected from methyl, ethyl, or trifluoromethyl.

$Cy^2$ is (a) hydrogen or (b) optionally substituted aryl, optionally substituted heteroaryl, optionally substituted cycloalkyl or optionally substituted heterocyclyl.

The method comprises the step of reacting a β-haloalcohol compound, for example a β-haloalcohol compound represented by structural formula (II)

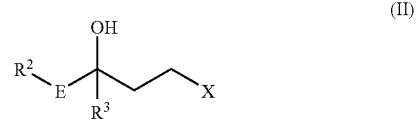

with an isocyanate compound represented by structural formula (III)

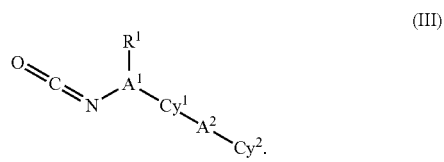

X is a leaving group

Another embodiment of the present invention is a method of preparing an epoxide compound represented by structural formula (IV):

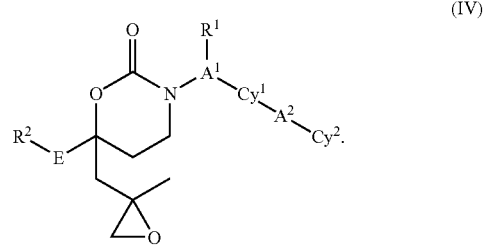

The method comprises the step of oxidizing with an epoxidation reagent a 2-methyl-2-propenyl intermediate represented by the following structural formula:

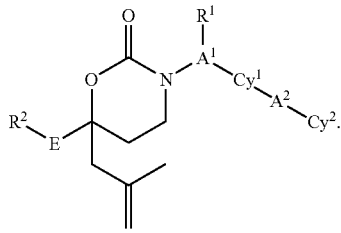

(V)

$A^1, A^2, Cy^1, Cy^2, R^1, R^2$ and E in structural formulas (IV) and (V) are as defined in structural formula (I).

Another embodiment of the present invention is a method of preparing tertiary alcohol oxazinone compound represented by structural formula (VI):

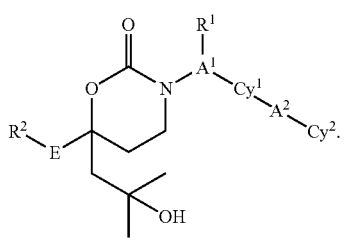

(VI)

The method comprises the step of reducing the epoxide group of the epoxide compound represented by structural formula (IV) with a reducing agent. $A^1, A^2, Cy^1, Cy^2, R^1, R^2$ and E in structural formula (VI) are as defined in structural formula (V).

In an alternative embodiment, the tertiary alcohol oxazinone compound represented by structural formula (VI) can be prepared using the compound of structural formula VII:

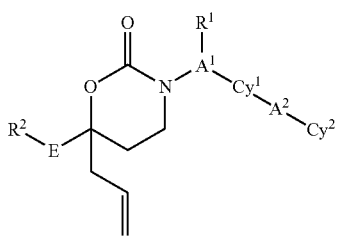

(VII)

following the synthetic scheme set forth in FIG. 2. Example 22 provides details of the synthetic steps of FIG. 2 for the preparation of (S)-3-((S)-1-(4-bromophenyl)ethyl)-6-(2-hydroxy-2-methylpropyl)-6-phenyl-1,3-oxazinan-2-one.

$A^1, A^2, Cy^1, Cy^2, R^1, R^2$ and E in structural formula (VII) are as defined in structural formula (I).

Another embodiment of the present invention is an epoxide compound represented by structural formula (IV) or a salt thereof.

Yet another embodiment of the present invention is a 2-methyl-2-propenyl intermediate represented by structural formula (V) or a salt thereof.

Other embodiments of the present invention are the epoxide compounds and salts thereof, and 2-methyl-2-propenyl intermediates and salts thereof as prepared with the methods of the present invention, in particular, the epoxide compounds and 2-methyl-2-propenyl intermediates corresponding to the above described embodiments.

DETAILED DESCRIPTION OF THE INVENTION

Figure 1:
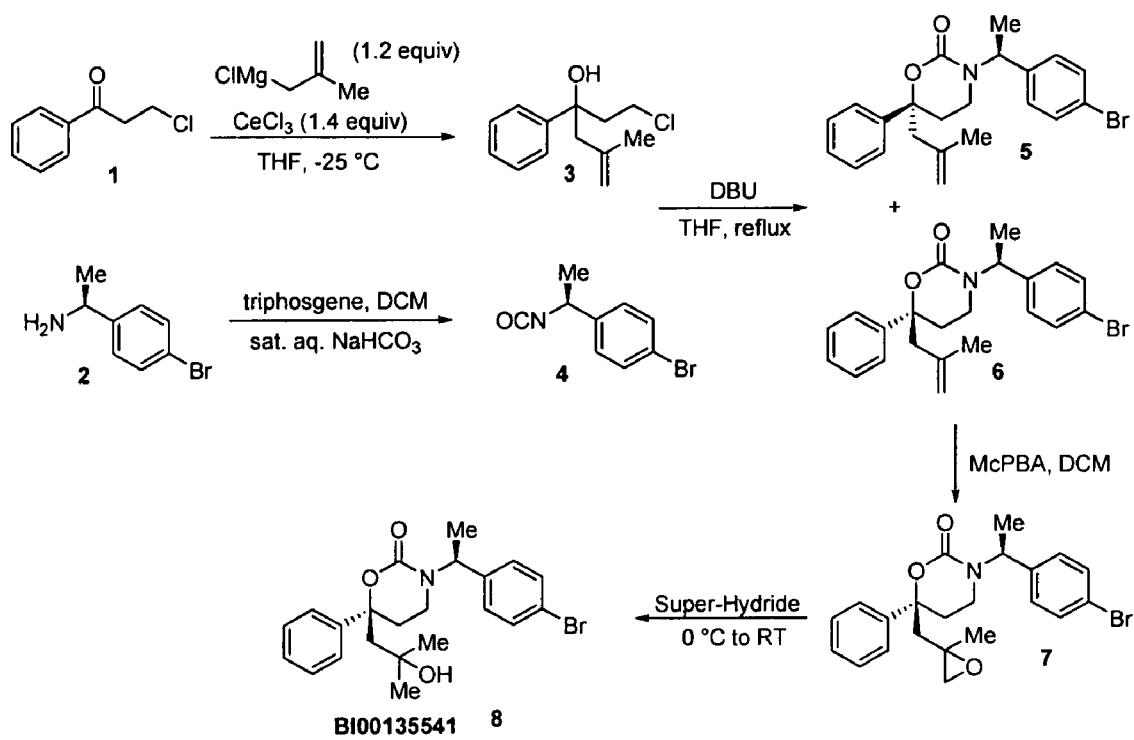
FIG. 1 is a schematic, showing the synthesis of a specific tertiary alcohol oxazinone compound, a 11β-HSD1 inhibitor, using the methods disclosed herein.
Figure 2:
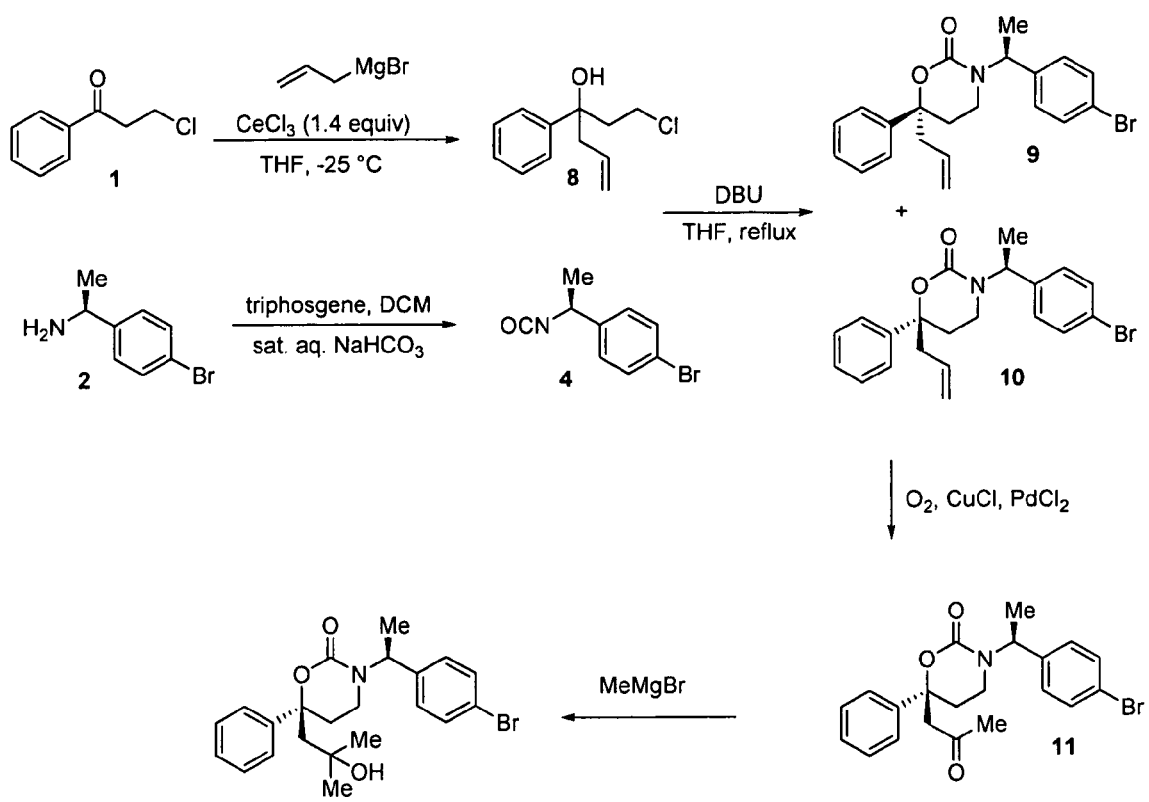
FIG. 2 is a schematic, showing the synthesis of a specific tertiary alcohol oxazinone compound, a 11β-HSD1 inhibitor, using the methods disclosed herein.

The present invention provides methods for synthesizing 11β-HSD1 inhibitors, for example, oxazinone compounds and tertiary alcohol oxazinone compounds as disclosed herein.

The oxazinone compound represented by structural formula (I), for example, compounds 5 and 6 (see Figure), can be prepared by reacting a β-haloalcohol compound represented by structural formula (II) with an isocyanate compound represented by structural formula (III). Both, the β-haloalcohol compound and the isocyanate compound can be prepared from commercially available compounds using methods known in the art (see, Exemplification section).

The tertiary alcohol oxazinone compound represented by structural formula (VI) such as, for example, compound 8 (see FIG. 1) is prepared by first oxidizing 2-methyl-2-propenyl intermediate represented by structural formula (V) with an epoxidation reagent to obtain the epoxide compound represented by structural formula (IV). The 2-methyl-2-propenyl intermediate is an oxazinone compound that can be prepared using the method described in the previous paragraph, wherein $R^3$ is 2-methyl-2-propenyl. In a second step, the epoxide group of the epoxide compound is reduced with a reducing agent to form the tertiary alcohol oxazinone compound.

Oxazinone compounds and tertiary alcohol oxazinone compounds represented by structural formulas (I) and (VI), respectively, for which $Cy^1$ is phenyl substituted with a leaving group (e.g., —Br) and optionally substituted with one or more additional substituents, can be used to prepare biaryl group containing 11β-HSD1 inhibitors, for example, by using a "Suzuki" coupling reaction as described in Example 111 of U.S. Provisional Patent Application No. 60/962,058, filed Jul. 26, 2007. Alternatively, oxazinone compounds represented by structural formulas (I) and (VI), respectively, for which $Cy^1$ is phenyl substituted with a leaving group (e.g., —Br) and optionally substituted with one or more additional substituents, can be used to prepare biaryl group containing 11β-HSD1 inhibitors, by conversion of the leaving group (e.g. —Br) to a boronic acid or boronate ester, followed by using a "Suzuki" coupling reaction with $Cy^2$-Cl or $Cy^2$-Br (see EXAMPLE 23). Alternatively, biaryl group containing 11β-HSD1 inhibitors can be obtained from isocyanate compounds that already contain the biaryl group using the methods of the present invention. The synthesis of a variety of biaryl compounds is provided in the Exemplification section.

A detailed description of each reaction in the syntheses is provided below. In the discussion below, $A^1, A^2, Cy^1, Cy^2, R^1, R^2$ and E have the meanings indicated above unless otherwise noted. In cases where the synthetic intermediates and final products described below contain potentially reactive functional groups, for example amino, hydroxyl, thiol, sulfonamide, amide and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 2007, herein incorporated by reference in its entirety). Such protecting group manipulations are assumed in the discussion below and not described explicitly. The term "protected" as used herein in combination with terms denoting chemical groups, for example, protected piperidinyl, refers to the chemical group with its functional groups that may interfere with a desired reaction having been reacted with a protective group, e.g., the ring nitrogen atom in the case piperidine.

Oxazinone Compounds

The oxazinone compound represented by structural formula (I) is prepared by reacting a β-haloalcohol compound represented by structural formula (II) with an isocyanate compound represented by structural formula (III) as shown above. Typically, the reaction of the a β-haloalcohol with the isocyanate compound is carried out in the presence of a base. More typically, the reaction is carried out in the presence of a non-nucleophilic base. Most typically, the reaction is carried out in the presence of a non-nucleophilic amine base. Suitable non-nucleophilic amide bases include, but are not limited to as lithium amide ($LiNH_2$), sodium amide ($NaNH_2$), lithium dimethylamide, lithium diethylamide, lithium diisopropylamide, lithium dicyclohexylamide, silicon-based amides, such as sodium and potassium bis(trimethylsilyl)amide, lithium tetramethylpiperidide, and lithium tetramethylpiperidine. Other non-nucleophilic bases include but are not limited to sodium hydride, sodium tert-pentoxide and sodium tert-butoxide. Examples of suitable non-nucleophilic amine bases include, but are not limited to, diisopropylethylamine, 2,2,6,6-tetramethylpiperidine, 4-dimethylaminopyridine, 2,6-di-tert-butyl-4-methylpyridine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), 2,8,9-trimethyl-2,5,8,9-tetraaza-1-phosphabicyclo[3.3.3]undecane and the like. Most typically, the base is 1,8-diazabicyclo[5.4.0]undec-7-ene. Although an excess of either β-haloalcohol compound or isocyanate compound can be used, the isocyanate compound is more commonly used in excess. Typically, from about one to about ten equivalents of base relative to β-haloalcohol are used, more typically from about one to about six equivalents, and, even more typically, from one to about 5 equivalents. Typically the reaction is carried out in an anhydrous aprotic, non-nucleophilic solvent at β-haloalcohol compound concentrations between about 0.01 M and 5 M. β-Haloalcohol compound concentrations are more typically, however, between about 0.05 M and 2 M. Suitable solvents include, but are not limited to ethereal solvents such as diethyl ether, tetrahydrofuran (THF), tert-butyl-methyl ether and 1,4-dioxane, and non-ethereal solvents such as dimethyl formamide and dimethyl sulfoxide and the like. Suitable reaction temperatures generally range from about 0° C. to about the boiling point of the solvent. More typically, temperatures are sufficiently high to allow refluxing, for example, about 68° C. for tetrahydrofuran.

Epoxide Compounds

The epoxide compound represented by structural formula (IV) is prepared by oxidizing the propenyl group of the 2-methyl-2-propenyl intermediate represented by structural formula (V) with an epoxidation reagent. The 2-methyl-2-propenyl intermediate is an oxazinone compound that can be prepared using the method described in the previous paragraphs (e.g., the reaction of a compound of Formula II with a compound of Formula III). Suitable epoxidation reagents include, but are not limited to peroxides (e.g., hydrogen peroxide, t-butyl hydroperoxide), peroxycarboxylic acids (e.g., 3-chloroperbenzoic acid (MCPBA), peracetic acid, pertrifluoroacetic acid), magnesium bis(monoperoxyphthalate) hexahydrate, potassium monoperoxysulfate optionally in the presence of 1,2:4,5-di-O-isopropylidene-β-D-erythro-2,3-hexodiulo-2,6-pyranose, dimethyldioxirane and the like. Typically, the epoxidation reagent is a peroxycarboxylic acid, and, most typically, it is 3-chloroperbenzoic acid. Typically, from about one to about ten equivalents of epoxidation reagent relative to 2-methyl-2-propenyl intermediate are used, more typically from about one to about six equivalents, and, most typically, from about one to about 2 equivalents. Typically the reaction is carried out in an aprotic, non-nucleophilic solvent at 2-methyl-2-propenyl intermediate concentrations between about 0.01 M and 5 M. 2-Methyl-2-propenyl intermediate concentrations are more typically, however, between about 0.05 M and 2 M. Suitable solvents include, but are not limited to, halogenated solvents (e.g., chloroform, dichloromethane and 1,2-dichloroethane, acetonitrile, dimethylformamide (DMF), dimethylacetamide (DMA), or hexamethylphosphorus triamide and ethereal solvents such as diethyl ether, tetrahydrofuran (THF) and 1,4-dioxane. Typically, the solvent is a halogenated solvent. More typically, the solvent is dichloromethane or 1,2-dichloroethane. Most typically, the solvent is dichloromethane. Suitable reaction temperatures generally range from about 0° C. to about the boiling point of the solvent used. Most typically, the reaction is carried out at ambient temperature.

Tertiary Alcohol Oxazinone Compounds

The tertiary alcohol oxazinone compound represented by structural formula (VI) is prepared by reducing the epoxide group of the epoxide compound represented by structural formula (IV) with a reducing agent. Suitable reducing agents include, but are not limited to hydride reducing agents such as lithium triethylborohydride, $LiAlH_4$, $LiBH_4$, lithium tri-t-butoxyaluminum hydride in the presence of triethylborane, potassium tri-sec-butylborohydride or sodium bis(2-methoxyethoxy)aluminum hydride and the like. Other suitable reducing agents include, but are not limited to $BH_3.Et_3N$—$LiClO_4$, lithium di-tert-butylbiphenyl, or hydrogen or sodium formate in the presence of palladium on charcoal. Most typically, the reducing agent is lithium triethylborohydride (super hydride). Typically, from about one to about ten equivalents of reducing agent relative to the epoxide compound are used, more typically from about one to about six equivalents, and, most typically, from about one to about 2 equivalents. Typically the reaction is carried out in an anhydrous aprotic, non-nucleophilic solvent at epoxide compound concentrations between about 0.01 M and 5 M. Epoxide compound concentrations are more typically, however, between about 0.05 M and 2 M. Suitable solvents include, but are not limited to ethereal solvents such as diethyl ether, tetrahydrofuran (THF), tert-butyl-methyl ether and 1,4-dioxane, and non-ethereal solvents such as dimethyl formamide and dimethyl sulfoxide and the like. Typically, the solvent is an ethereal solvent. Most typically, the solvent is anhydrous tetrahydrofuran. Suitable reaction temperatures generally range from about 0° C. to about ambient temperature.

The processes for preparing the oxazinone compound represented by structural formula (I), the epoxide compound represented by structural formula (IV) and the tertiary alcohol oxazinone compound represented by structural formula (VI)

as described in the previous three paragraphs and for the compounds represented by structural formulas (I), (IV), (V), (VI) and (VII) can further be described according to the following preferred embodiments. Note that $R^3$ and X refer to the preparation of an oxazinone compound only.

In a first preferred embodiment, $Cy^1$, $Cy^2$, $R^2$, $R^3$ and X are as defined in structural formulas (I) to (VI) (see summary of invention) and $R^1$ is absent or is $(C_1-C_6)$alkyl; $A^1$ is a bond, $CH_2$, or $CH_2CH_2$, or CH when $R^1$ is present; $A^2$ is a bond, O, $OCH_2CO$ or $CH_2$; X is a Cl, Br, I or $—OSO_2R$, wherein R is $(C_1-C_4)$alkyl optionally substituted with one or more F, or phenyl optionally substituted with halogen, $(C_1-C_4)$alkyl or $NO_2$; and E is a bond or $(C_1-C_3)$alkylene.

In a second preferred embodiment, $R^1$, $R^2$, $R^3$, X and E are as defined in the first preferred embodiment and $A^1$ is a bond or CH when $R^1$ is present; $A^2$ is a bond; $Cy^2$ is hydrogen; $Cy^1$ is phenyl substituted with Cl, Br, I or $OSO_2CF_3$, and optionally substituted with one or more additional substituents.

In a third preferred embodiment, $A^2$, $Cy^2$, $R^1$, $R^2$, $R^3$, X and E are as defined in the second preferred embodiment and $A^1$ is —CH, $R^1$ is present and $Cy^1$ is represented by the following structural formula:

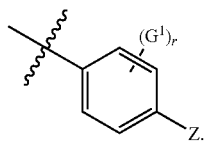

Z is a Cl, Br, I, $OSO_2CF_3$, $OSO_2Me$, or $OSO_2C_6H_4Me$, r is 0, 1, 2 or 3; and each G' is independently selected from the group consisting of $(C_1-C_4)$alkyl, halo$(C_1-C_4)$ alkyl, $(C_1-C_4)$ alkoxy, halogen, cyano and nitro.

In a fourth preferred embodiment, $A^1$, $A^2$, $Cy^1$, $Cy^2$, $R^2$, $R^3$, X, E, r, $G^1$ and Z are defined as in the third preferred embodiment and $R^1$ is methyl or ethyl.

In a fifth preferred embodiment, $A^1$, $A^2$, $Cy^1$, $Cy^2$, $R^1$, X, E, r, $G^1$ and Z are defined as in the fourth preferred embodiment and $R^2$ is phenyl, thienyl, or pyridyl, each optionally substituted with halogen, nitro, cyano, $(C_1-C_6)$alkyl, protected hydroxy$(C_1-C_3)$alkyl, $(C_1-C_3)$alkoxy, protected $CONH_2$, protected carboxylic acid and $SO_2Me$; and with regard to the preparation of an oxazinone compound, $R^3$ is methyl, ethyl, propyl, butyl, vinyl, allyl, 2-methyl-2-propenyl, or ethoxyethyl, each optionally substituted with up to two groups independently selected from $(C_1-C_4)$alkyl, $(C_1-C_4)$alkoxy, $(C_1-C_4)$alkoxycarbonyl, benzyloxycarbonyl, protected hydroxy $(C_1-C_4)$alkyl, cyano$(C_1-C_4)$alkyl, protected $(C_1-C_4)$ alkylamino, di$(C_1-C_4)$alkylamino, halogen, cyano, oxo, nitro, protected hydroxy, protected amino, $MeSO_2—$, $MeSO_2N(Me)(C_1-C_4)$alkyl, protected $MeSO_2NH(C_1-C_4)$ alkyl, protected $H_2NC(=O)CMe_2(C_1-C_4)$alkyl, protected $H_2NC(=O)CHMe(C_1-C_4)$alkyl and protected $H_2NC(=O)CH_2(C_1-C_4)$alkyl.

In a sixth preferred embodiment, $A^1$, $A^2$, $Cy^1$, $Cy^2$, $R^1$, $R^2$, X, E, r, $G^1$ and Z are defined as in the fifth preferred embodiment and, with regard to the preparation of an oxazinone compound, $R^3$ is vinyl, allyl, 2-methyl-2-propenyl, $MeSO_2NHCH_2CH_2CH_2$, protected $H_2NC(=O)CH_2CH_2$, protected $H_2NC(=O)CMe_2CH_2$, 2-cyano-2-methylpropyl, 2-oxopropyl or $(C_1-C_4)$alkoxycarbonylmethyl.

In a seventh preferred embodiment, $A^1$, $A^2$, $Cy^1$, $Cy^2$, $R^1$, $R^3$, X, E, r, $G^1$ and Z are defined as in the sixths preferred embodiment and $R^2$ is phenyl optionally substituted with 1, 2 or 3 substituents selected from halo, cyano, protected $CONH_2$, $(C_1-C_4)$alkyl, $(C_1-C_4)$alkoxy and $SO_2Me$.

In an eight preferred embodiment, $A^1$, $A^2$, $Cy^1$, $Cy^2$, $R^1$, $R^2$, X, E, r, $G^1$ and Z are defined as in the seventh preferred embodiment and, with regard to the preparation of an oxazinone compound, $R^3$ is allyl, 2-methyl-2-propenyl, protected $H_2NC(=O)CMe_2CH_2$ or 2-cyano-2-methylpropyl.

In a ninth preferred embodiment, $A^1$, $A^2$, $Cy^1$, $Cy^2$, $R^1$, $R^2$, X, A E, r, $G^1$ and Z are defined as in the seventh preferred embodiment and, with regard to the preparation of an oxazinone compound, $R^3$ is 2-methyl-2-propenyl or 2-cyano-2-methylpropyl.

In a tenth preferred embodiment, $A^1$, $A^2$, $Cy^1$, $Cy^2$, $R^1$, $R^3$, X, E, r, $G^1$ and Z are defined as in the ninth preferred embodiment and $R^2$ is phenyl or fluorophenyl.

In an eleventh preferred embodiment, $A^1$, $A^2$, $R^1$, $R^2$, $R^3$, X and E are defined as in the first preferred embodiment and $Cy^1$ is phenyl, cyclopropyl, cyclohexyl, pyrrolidinyl, piperidinyl, azepanyl, pyridyl, thiazolyl, pyrimidinyl, each optionally substituted with 1 to 4 groups; and $Cy^2$ is phenyl, thienyl, pyridyl, cyclopropyl, piperidinyl, piperazinyl, morpholinyl, thiazolyl, oxadiazolyl, thiadiazolyl, pyrazolyl, S,S-dioxothiazinyl, pyridazinyl, pyrimidinyl, pyrazinyl, benzimidazolyl, benztriazolyl, oxodihydropyridyl, oxodihydropyridazinyl, oxodihydropyrimidinyl and oxodihydropyrazinyl, each optionally substituted by 1 to 4 groups; wherein substituents for a ring carbon atom of $Cy^1$ and $Cy^2$ are independently selected from halogen, cyano, oxo, nitro, protected hydroxy, protected amino, $(C_1-C_4)$alkyl, $(C_3-C_4)$cycloalkyl, $(C_3-C_4)$cycloalkyl$(C_1-C_2)$alkyl, $(C_1-C_4)$alkoxy, $(C_1-C_4)$alkoxycarbonyl, benzoxycarbonyl, protected $CONH_2$, protected $(C_r-C_4)$alkylaminocarbonyl, di$(C_1-C_4)$alkylaminocarbonyl, protected $(C_3-C_4)$cycloalkylaminocarbonyl, $\{(C_1-C_4)$alkyl$\}\{(C_3-C_4)$cycloalkyl$\}$aminocarbonyl and protected $(C_1-C_4)$ alkylcarbonylamino, wherein suitable substituents for a substitutable ring nitrogen atom in $Cy^2$ are selected from the group consisting of $(C_r-C_4)$alkyl, $(C_3-C_4)$cycloalkyl, $(C_3-C_4)$cycloalkyl$(C_1-C_2)$alkyl, $(C_1-C_4)$alkoxycarbonyl, $(C_1-C_4)$alkylcarbonyl and benzyloxycarbonyl. For the process of preparing an oxazinone compound, each substitutable ring nitrogen atom of $Cy^2$, if present, is either bonded to $A^2$, protected or substituted.

In a twelfth preferred embodiment, $A^1$, $A^2$, $Cy^1$, $Cy^2$, $R^2$, $R^3$, X and E are defined as in the eleventh preferred embodiment and $R^1$ is methyl or ethyl.

In a thirteenth preferred embodiment, $A^1$, $A^2$, $Cy^1$, $Cy^2$, $R^1$, X and E are defined as in the twelfth preferred embodiment and $R^2$ is phenyl, thienyl, or pyridyl, each optionally substituted with halogen, nitro, cyano, $(C_1-C_6)$alkyl, protected hydroxy$(C_1-C_3)$alkyl, $(C_1-C_3)$alkoxy, protected $CONH_2$, protected carboxylic acid and $SO_2Me$; and, with regard to the preparation of an oxazinone compound, $R^3$ is methyl, ethyl, propyl, butyl, vinyl, allyl, 2-methyl-2-propenyl, or ethoxyethyl each optionally substituted with up to two groups independently selected from $(C_1-C_4)$alkyl, $(C_1-C_4)$alkoxy, $(C_1-C_4)$alkoxycarbonyl, benzyloxycarbonyl, protected hydroxy $(C_1-C_4)$alkyl, cyano$(C_1-C_4)$alkyl, protected $(C_1-C_4)$ alkylamino, di$(C_1-C_4)$alkylamino, halogen, cyano, oxo, nitro, protected hydroxy, protected amino, $MeSO_2—$, $MeSO_2N(Me)(C_1-C_4)$alkyl, protected $MeSO_2NH(C_1-C_4)$ alkyl, protected $H_2NC(=O)CMe_2(C_1-C_4)$alkyl, protected $H_2NC(=O)CHMe(C_1-C_4)$alkyl and protected $H_2NC(=O)CH_2(C_1-C_4)$alkyl.

In a fourteenth preferred embodiment, $A^1$, $A^2$, $Cy^1$, $R^1$, $R^2$, $R^3$, X and E are defined as in the thirteenth preferred embodiment and $Cy^2$ is optionally substituted and selected from the group consisting of benzimidazolyl, benzotriazolyl, oxodihydropyridyl, oxodihydropyridazinyl, oxodihydropyrimidinyl, oxodihydropyrazinyl, piperidinyl, pyridinyl, pyridazinyl, pyrimidinyl, pyrazinyl, pyrazolyl, thiazolyl and thiadiazolyl.

In a fifteenth preferred embodiment, $A^1$, $A^2$, $Cy^1$, $Cy^2$, $R^1$, $R^2$, X and E are defined as in the fourteenth preferred embodiment and, with regard to the preparation of an oxazinone compound, $R^3$ is vinyl, allyl, 2-propenyl-2-methyl, $MeSO_2NHCH_2CH_2CH_2$, protected $H_2NC(=O)CH_2CH_2$, protected $H_2NC(=O)CMe_2CH_2$, 2-cyano-2-methylpropyl, 2-oxopropyl or $(C_1-C_4)$alkoxycarbonylmethyl.

In a sixteenth preferred embodiment, $A^1$, $A^2$, $Cy^1$, $Cy^2$, $R^1$, $R^3$, X and E are defined as in the fifteenth preferred embodiment and $R^2$ is phenyl optionally substituted with 1, 2 or 3 substituents selected from halo, cyano, protected $CONH_2$, $(C_1-C_4)$alkyl, $(C_1-C_4)$alkoxy and $SO_2Me$.

In a seventeenth preferred embodiment, $A^1$, $A^2$, $Cy^1$, $Cy^2$, $R^1$, $R^2$, X and E are defined as in the sixteenth preferred embodiment and with regard to the preparation of an oxazinone compound, $R^3$ is allyl, 2-propenyl-2-methyl, protected $H_2NC(=O)CMe_2CH_2$ or 2-cyano-2-methylpropyl.

In an eighteenth preferred embodiment, $A^1$, $A^2$, $Cy^1$, $Cy^2$, $R^1$, $R^2$, X and E are defined as in the seventeenth preferred embodiment and, with regard to the preparation of an oxazinone compound, $R^3$ is 2-propenyl-2-methyl, or 2-cyano-2-methylpropyl.

In a nineteenth preferred embodiment, $A^1$, $A^2$, $Cy^1$, $Cy^2$, $R^1$, $R^2$, $R^3$, X and E are defined as in the eighteenth preferred embodiment and $R^2$ is phenyl or fluorophenyl.

In a twentieth preferred embodiment, $A^1$, $A^2$, $Cy^1$, $Cy^2$, $R^1$, $R^2$, $R^3$, X and E are are defined as in the nineteenth preferred embodiment and suitable substituents for a substitutable ring nitrogen atom in the group represented by $Cy^2$ are selected from the group consisting of $(C_1-C_4)$alkyl, $(C_3-C_4)$cycloalkyl, $(C_3-C_4)$cycloalkyl$(C_1-C_2)$alkyl, $(C_1-C_4)$alkoxycarbonyl and $(C_1-C_4)$alkylcarbonyl; and suitable substituents for a substitutable ring carbon atom in the $Cy^2$ is selected from the group consisting fluorine, chlorine, cyano, protected hydroxy, protected amino, $(C_1-C_4)$alkyl, $(C_3-C_4)$cycloalkyl, $(C_3-C_4)$cycloalkyl$(C_1-C_2)$alkyl, $(C_1-C_4)$alkoxy, protected $CONH_2$, protected $(C_1-C_4)$alkylaminocarbonyl, di$(C_1-C_4)$alkylaminocarbonyl, protected $(C_3-C_4)$cycloalkylaminocarbonyl, $\{(C_1-C_4)$alkyl$\}\{(C_3-C_4)$cycloalkyl$\}$aminocarbonyl and protected $(C_1-C_4)$alkylcarbonylamino.

In a twenty-first preferred embodiment, with regard to the preparation of an oxazinone compound, $A^1$, $A^2$, $Cy^1$, $Cy^2$, $R^1$, $R^2$, X and E are as defined in any one of the above preferred embodiments and $R^3$ is 2-methyl-2-propenyl.

In a twenty-second preferred embodiment, with regard to the preparation of an oxazinone compound, $A^1$, $A^2$, $Cy^1$, $Cy^2$, $R^1$, $R^2$, X and E are as defined in any one of the above preferred embodiments and $R^3$ is 2-propenyl.

In a twenty-third preferred embodiment, $A^1$, $A^2$, $Cy^1$, $R^1$, $R^2$, X and E are as defined in any one of the above preferred embodiments and $Cy^2$ is represented by one of the following structural formulas:

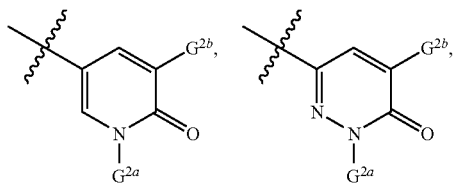

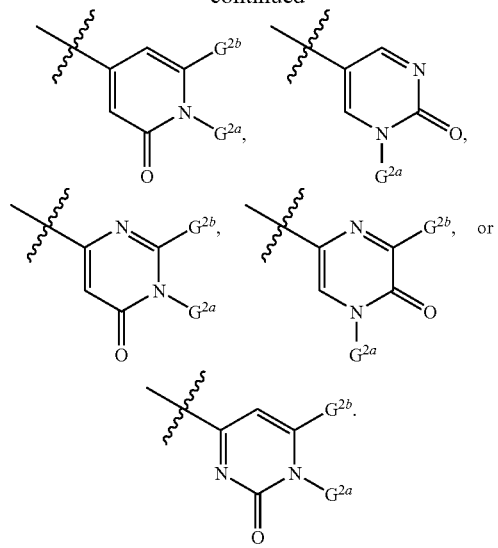

$G^{2a}$ is $(C_1-C_4)$alkyl, $(C_3-C_4)$cycloalkyl or $(C_1-C_4)$haloalkyl; $G^{2b}$ is hydrogen, fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl or $(C_1-C_4)$alkylcarbonylamino.

Other embodiments of the present invention are the epoxide compounds and salts thereof, and 2-methyl-2-propenyl intermediates and salts thereof as prepared with the methods of the present invention, in particular, the epoxide compounds and 2-methyl-2-propenyl intermediates corresponding to the above described preferred embodiments.

The following individual compounds can be prepared by a suitable choice of starting materials:

(S)-3-((S)-1-(4-(1,5-dimethyl-6-oxo-1,6-dihydropyridazin-3-yl)phenyl)ethyl)-6-(2-hydroxy-2-methylpropyl)-6-phenyl-1,3-oxazinan-2-one (S)-3-((S)-1-(4-(1,4-dimethyl-6-oxo-1,6-dihydropyridazin-3-yl)phenyl)ethyl)-6-(2-hydroxy-2-methylpropyl)-6-phenyl-1,3-oxazinan-2-one (S)-3-((S)-1-(4-(1,2-dimethyl-1H-benzo[d]imidazol-6-yl)phenyl)ethyl)-6-(2-hydroxy-2-methylpropyl)-6-phenyl-1,3-oxazinan-2-one (S)-6-(2-hydroxy-2-methylpropyl)-3-((S)-1-(4-(1-methyl-1H-benzo[d]imidazol-5-yl)phenyl)ethyl)-6-phenyl-1,3-oxazinan-2-one (S)-3-((S)-1-(4-(1,2-dimethyl-1H-benzo[d]imidazol-5-yl)phenyl)ethyl)-6-(2-hydroxy-2-methylpropyl)-6-phenyl-1,3-oxazinan-2-one (S)-3-((S)-1-(4-(1-(cyclopropylmethyl)-6-oxo-1,6-dihydropyridazin-3-yl)phenyl)ethyl)-6-(2-hydroxy-2-methylpropyl)-6-phenyl-1,3-oxazinan-2-one (S)-3-((S)-1-(4-(1-cyclopropyl-6-oxo-1,6-dihydropyridazin-3-yl)phenyl)ethyl)-6-(2-hydroxy-2-methylpropyl)-6-phenyl-1,3-oxazinan-2-one (S)-3-((S)-1-(4-(1-cyclopropyl-2-oxo-1,2-dihydropyridin-4-yl)phenyl)ethyl)-6-(2-hydroxy-2-methylpropyl)-6-phenyl-1,3-oxazinan-2-one 2-(4-((S)-1-((S)-6-(2-hydroxy-2-methylpropyl)-2-oxo-6-phenyl-1,3-oxazinan-3-yl)ethyl)phenyl)nicotinonitrile (S)-3-((S)-1-(4-(1-(cyclopropylmethyl)-6-oxo-1,6-dihydropyridin-3-yl)phenyl)ethyl)-6-(2-hydroxy-2-methylpropyl)-6-phenyl-1,3-oxazinan-2-one N-ethyl-5-(4-((S)-1-((S)-6-(2-hydroxy-2-methylpropyl)-2-oxo-6-phenyl-1,3-oxazinan-3-yl)ethyl)phenyl)picolinamide 5-(4-((S)-1-((S)-6-(2-hydroxy-2-methylpropyl)-2-oxo-6-phenyl-1,3-oxazinan-3-yl)ethyl)phenyl)-N-methylpicolinamide 5-(4-((S)-1-((S)-6-(2-hydroxy-2-methylpropyl)-2-oxo-6-phenyl-1,3-oxazinan-3-yl)ethyl)phenyl)-N,N-dimethylpicolinamide (S)-3-((S)-1-(4-(1H-benzo[d][1,2,3]triazol-6-yl)phenyl)ethyl)-6-(2-hydroxy-2-methylpropyl)-6-phenyl-1,3-oxazinan-2-one (S)-6-(2-hydroxy-2-methylpropyl)-3-((S)-1-(4-(2-methyl-1H-benzo[d]imidazol-6-yl)phenyl)ethyl)-6-phenyl-1,3-oxazinan-2-one (S)-6-(2-hydroxy-2-methylpropyl)-6-phenyl-3-((S)-1-(4-(1,5,6-trimethyl-2-oxo-1,2-dihydropyridin-4-yl)phenyl)ethyl)-1,3-oxazinan-2-one 2-(4-((S)-1-((S)-6-(2-hydroxy-2-methylpropyl)-2-oxo-6-phenyl-1,3-oxazinan-3-yl)ethyl)phenyl)nicotinonitrile 2-(4-((S)-1-((S)-6-(2-hydroxy-2-methylpropyl)-2-oxo-6-phenyl-1,3-oxazinan-3-yl)ethyl)phenyl)isonicotinonitrile N-tert-butyl-6-(4-((S)-1-((S)-6-(2-hydroxy-2-methylpropyl)-2-oxo-6-phenyl-1,3-oxazinan-3-yl)ethyl)phenyl)nicotinamide (S)-3-((S)-1-(4-(2-ethoxy-6-methylpyridin-4-yl)phenyl)ethyl)-6-(2-hydroxy-2-methylpropyl)-6-phenyl-1,3-oxazinan-2-one (S)-3-((S)-1-(4-(1-ethyl-6-methyl-2-oxo-1,2-dihydropyridin-4-yl)phenyl)ethyl)-6-(2-hydroxy-2-methylpropyl)-6-phenyl-1,3-oxazinan-2-one (S)-3-((S)-1-(4-(6-ethoxy-5-methylpyridin-3-yl)phenyl)ethyl)-6-(2-hydroxy-2-methylpropyl)-6-phenyl-1,3-oxazinan-2-one (S)-3-((S)-1-(4-(1-ethyl-5-methyl-6-oxo-1,6-dihydropyridin-3-yl)phenyl)ethyl)-6-(2-hydroxy-2-methylpropyl)-6-phenyl-1,3-oxazinan-2-one N-cyclopropyl-6-(4-((S)-1-((S)-6-(2-hydroxy-2-methylpropyl)-2-oxo-6-phenyl-1,3-oxazinan-3-yl)ethyl)phenyl)nicotinamide (S)-6-(2-hydroxy-2-methylpropyl)-3-((S)-1-(4-(1-isopropyl-6-oxo-1,6-dihydropyridazin-3-yl)phenyl)ethyl)-6-phenyl-1,3-oxazinan-2-one (S)-6-(2-hydroxy-2-methylpropyl)-3-((S)-1-(4-(6-oxo-1-(2,2,2-trifluoroethyl)-1,6-dihydropyridazin-3-yl)phenyl)ethyl)-6-phenyl-1,3-oxazinan-2-one (S)-3-((S)-1-(4-(1-ethyl-6-oxo-1,6-dihydropyridazin-3-yl)phenyl)ethyl)-6-(2-hydroxy-2-methylpropyl)-6-phenyl-1,3-oxazinan-2-one (S)-6-(2-hydroxy-2-methylpropyl)-3-((S)-1-(4-(1-isopropyl-2-oxo-1,2-dihydropyridin-4-yl)phenyl)ethyl)-6-phenyl-1,3-oxazinan-2-one (S)-6-(2-hydroxy-2-methylpropyl)-3-((S)-1-(4-(6-oxo-1-(2,2,2-trifluoroethyl)-1,6-dihydropyridin-3-yl)phenyl)ethyl)-6-phenyl-1,3-oxazinan-2-one 6-(4-((S)-1-((S)-6-(4-fluorophenyl)-6-(2-hydroxy-2-methylpropyl)-2-oxo-1,3-oxazinan-3-yl)ethyl)phenyl)pyrazine-2-carboxamide 2-(4-((S)-1-((S)-6-(2-hydroxy-2-methylpropyl)-2-oxo-6-phenyl-1,3-oxazinan-3-yl)ethyl)phenyl)-N,N-dimethylthiazole-5-carboxamide (S)-6-(2-hydroxy-2-methylpropyl)-3-((S)-1-(4-(2-oxo-1-(2,2,2-trifluoroethyl)-1,2-dihydropyridin-4-yl)phenyl)ethyl)-6-phenyl-1,3-oxazinan-2-one (S)-3-((S)-1-(4-(1-ethyl-2-oxo-1,2-dihydropyridin-4-yl)phenyl)ethyl)-6-(2-hydroxy-2-methylpropyl)-6-phenyl-1,3-oxazinan-2-one (S)-3-((S)-1-(4-(1,6-dimethyl-2-oxo-1,2-dihydropyridin-4-yl)phenyl)ethyl)-6-(2-hydroxy-2-methylpropyl)-6-phenyl-1,3-oxazinan-2-one 6-(4-((S)-1-((S)-6-(4-fluorophenyl)-6-(2-hydroxy-2-methylpropyl)-2-oxo-1,3-oxazinan-3-yl)ethyl)phenyl)pyrazine-2-carbonitrile (S)-3-((S)-1-(4-(1-ethyl-6-oxo-1,6-dihydropyridin-3-yl)phenyl)ethyl)-6-(4-fluorophenyl)-6-(2-hydroxy-2-methylpropyl)-1,3-oxazinan-2-one (S)-3-((S)-1-(4-(1,5-dimethyl-6-oxo-1,6-dihydropyridin-3-yl)phenyl)ethyl)-6-(2-hydroxy-2-methylpropyl)-6-phenyl-1,3-oxazinan-2-one (S)-6-(4-fluorophenyl)-6-(2-hydroxy-2-methylpropyl)-3-((S)-1-(4-(1-methyl-6-oxo-1,6-dihydropyridazin-3-yl)phenyl)ethyl)-1,3-oxazinan-2-one 6-(4-((S)-1-((S)-6-(2-hydroxy-2-methylpropyl)-2-oxo-6-phenyl-1,3-oxazinan-3-yl)ethyl)phenyl)-N,N-dimethylnicotinamide (S)-6-(4-fluorophenyl)-6-(2-hydroxy-2-methylpropyl)-3-((S)-1-(4-(6-methylpyridazin-3-yl)phenyl)ethyl)-1,3-oxazinan-2-one 4-(4-((S)-1-((S)-6-(2-hydroxy-2-methylpropyl)-2-oxo-6-phenyl-1,3-oxazinan-3-yl)propyl)phenyl)-2,6-dimethylpyridine 1-oxide 5-(4-((S)-1-((S)-6-(4-fluorophenyl)-6-(2-hydroxy-2-methylpropyl)-2-oxo-1,3-oxazinan-3-yl)ethyl)phenyl)pyrazine-2-carbonitrile 5-fluoro-2-(4-((S)-1-((S)-6-(2-hydroxy-2-methylpropyl)-2-oxo-6-phenyl-1,3-oxazinan-3-yl)ethyl)phenyl)pyridine 1-oxide (S)-6-(2-hydroxy-2-methylpropyl)-3-((S)-1-(4-(5-methylpyrazin-2-yl)phenyl)ethyl)-6-phenyl-1,3-oxazinan-2-one (S)-6-(2-hydroxy-2-methylpropyl)-3-((S)-1-(4-(1-isopropyl-6-oxo-1,6-dihydropyridin-3-yl)phenyl)ethyl)-6-phenyl-1,3-oxazinan-2-one 6-(4-((S)-1-((S)-6-(2-hydroxy-2-methylpropyl)-2-oxo-6-phenyl-1,3-oxazinan-3-yl)ethyl)phenyl)-N-methylnicotinamide (S)-6-(2-hydroxy-2-methylpropyl)-3-((S)-1-(4-(2-methylpyrimidin-5-yl)phenyl)ethyl)-6-phenyl-1,3-oxazinan-2-one (S)-6-(2-hydroxy-2-methylpropyl)-3-((S)-1-(4-(1-methyl-2-oxo-1,2-dihydropyridin-4-yl)phenyl)propyl)-6-phenyl-1,3-oxazinan-2-one (S)-6-(2-hydroxy-2-methylpropyl)-3-((S)-1-(4-(1-methyl-6-oxo-1,6-dihydropyridazin-3-yl)phenyl)ethyl)-6-phenyl-1,3-oxazinan-2-one (S)-6-(2-hydroxy-2-methylpropyl)-3-((S)-1-(4-(1-methyl-6-oxo-1,6-dihydropyridin-3-yl)phenyl)propyl)-6-phenyl-1,3-oxazinan-2-one (S)-3-((S)-1-(4-(1-ethyl-6-oxo-1,6-dihydropyridin-3-yl)phenyl)ethyl)-6-(2-hydroxy-2-methylpropyl)-6-phenyl-1,3-oxazinan-2-one (S)-3-((S)-1-(4-(1-ethyl-6-oxo-1,6-dihydropyridin-3-yl)phenyl)propyl)-6-(2-hydroxy-2-methylpropyl)-6-phenyl-1,3-oxazinan-2-one 6-(4-((S)-1-((S)-6-(2-hydroxy-2-methylpropyl)-2-oxo-6-phenyl-1,3-oxazinan-3-yl)ethyl)phenyl)nicotinamide (S)-3-((S)-1-(4-(5-fluoropyridin-2-yl)phenyl)ethyl)-6-(2-hydroxy-2-methylpropyl)-6-phenyl-1,3-oxazinan-2-one (S)-6-(2-hydroxy-2-methylpropyl)-3-((S)-1-(4-(2-methylpyrimidin-4-yl)phenyl)ethyl)-6-phenyl-1,3-oxazinan-2-one (S)-6-(2-hydroxy-2-methylpropyl)-6-phenyl-3-((S)-1-(4-(pyrimidin-4-yl)phenyl)ethyl)-1,3-oxazinan-2-one (S)-6-(2-hydroxy-2-methylpropyl)-3-((S)-1-(4-(6-methylpyridazin-3-yl)phenyl)ethyl)-6-phenyl-1,3-oxazinan-2-one (S)-6-(2-hydroxy-2-methylpropyl)-6-phenyl-3-((S)-1-(4-(pyrazin-2-yl)phenyl)ethyl)-1,3-oxazinan-2-one (S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one 6-(4-((S)-1-((S)-6-(2-hydroxy-2-methylpropyl)-2-oxo-6-phenyl-1,3-oxazinan-3-yl)ethyl)phenyl)nicotinonitrile (S)-3-((S)-1-(4-(2,6-dimethylpyridin-4-yl)phenyl)ethyl)-6-(2-hydroxy-2-methylpropyl)-6-phenyl-1,3-oxazinan-2-one (S)-3-((S)-1-(4-(2,6-dimethylpyridin-4-yl)phenyl)ethyl)-6-(4-fluorophenyl)-6-(2-hydroxy-2-methylpropyl)-1,3-oxazinan-2-one 4-(4-((S)-1-((S)-6-(2-hydroxy-2-methylpropyl)-2-oxo-6-phenyl-1,3-oxazinan-3-yl)ethyl)phenyl)-2,6-dimethylpyridine 1-oxide 6-(4-((S)-1-((S)-6-(4-fluorophenyl)-6-(2-hydroxy-2-methylpropyl)-2-oxo-1,3-oxazinan-3-yl)ethyl)phenyl)nicotinonitrile 4-(4-((S)-1-((S)-6-(4-fluorophenyl)-6-(2-hydroxy-2-methylpropyl)-2-oxo-1,3-oxazinan-3-yl)ethyl)phenyl)-2,6-dimethylpyridine 1-oxide 4-(4-((S)-1-((S)-6-(4-fluorophenyl)-6-(2-hydroxy-2-methylpropyl)-2-oxo-1,3-oxazinan-3-yl)ethyl)phenyl)-2-methylpyridine 1-oxide (S)-6-(2-hydroxy-2-methylpropyl)-3-((S)-1-(4-(1-methyl-6-oxo-1,6-dihydropyridin-3-yl)phenyl)ethyl)-6-phenyl-1,3-oxazinan-2-one (S)-6-(4-fluorophenyl)-6-(2-hydroxy-2-methylpropyl)-3-((S)-1-(4-(pyridin-2-yl)phenyl)ethyl)-1,3-oxazinan-2-one (S)-6-(4-fluorophenyl)-6-(2-hydroxy-2-methylpropyl)-3-((S)-1-(4-(6-methoxypyridin-3-yl)phenyl)ethyl)-1,3-oxazinan-2-one (S)-6-(2-hydroxy-2-methylpropyl)-6-phenyl-3-((S)-1-(4-(pyridin-2-yl)phenyl)ethyl)-1,3-oxazinan-2-one (S)-6-(2-hydroxy-2-methylpropyl)-3-((S)-1-(4-(6-methoxypyridin-3-yl)phenyl)ethyl)-6-phenyl-1,3-oxazinan-2-one (S)-6-(2-hydroxy-2-methylpropyl)-3-((S)-1-(4-(2-methylpyridin-4-yl)phenyl)ethyl)-6-phenyl-1,3-oxazinan-2-one (S)-6-(4-fluorophenyl)-6-(2-hydroxy-2-methylpropyl)-3-((S)-1-(4-(2-methylpyridin-4-yl)phenyl)ethyl)-1,3-oxazinan-2-one (S)-6-(4-fluorophenyl)-6-(2-hydroxy-2-methylpropyl)-3-((S)-1-(4-(1-methyl-6-oxo-1,6-dihydropyridin-3-yl)phenyl)ethyl)-1,3-oxazinan-2-one (S)-3-((S)-1-(4'-fluorobiphenyl-4-yl)ethyl)-6-(2-hydroxy-2-methylpropyl)-6-phenyl-1,3-oxazinan-2-one (S)-3-((S)-1-(2',4'-difluorobiphenyl-4-yl)ethyl)-6-(4-fluorophenyl)-6-(2-hydroxy-2-methylpropyl)-1,3-oxazinan-2-one As used herein, "β-haloalcohol compound," refers to compound represented by structural formula (II)

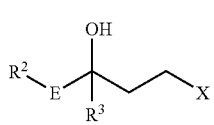

(II)

wherein X includes any suitable leaving group as described herein, not just halogen.

Suitable leaving groups include, but are not limited to halides, alkylsulfonates, trifluoromethanesulfonate (triflate) and phenylsulfonates which are optionally substituted with a methyl, halogen, nitro and the like, for example, methanesulfonate (mesylate), p-toluenesulfonate (tosylate), p-bromobenzenesulfonate (brosylate), p-nitrobenzenesulfonate (nosylate) and the like. Typically, leaving groups are Cl, Br, I or —OSO$_2$R, wherein R is (C$_1$-C$_4$)alkyl optionally substituted with one or more F, or phenyl optionally substituted with halogen, (C$_1$-C$_4$)alkyl or NO$_2$. Most typically, leaving groups are Cl, Br, I or —OSO$_2$R.

The term "biaryl group" as used herein refers to a group where an optionally substituted aryl or optionally substituted heteroaryl is bonded to another optionally substituted aryl or optionally substituted heteroaryl (e.g., biphenyl).

The term "alkyl" as used herein refers to a straight chain or branched saturated hydrocarbyl group having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl (c-Pr), cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like.

The term "aryl" means an aromatic radical which is a phenyl group, a naphthyl group, an indanyl group or a tetrahydronaphthalene group. An aryl group is optionally substituted with 1-4 substituents. Exemplary substituents include alkyl, alkoxy, alkylthio, alkylsulfonyl, halogen, trifluoromethyl, dialkylamino, nitro, cyano, CO$_2$H, CONH$_2$, N-monoalkyl-substituted amido and N,N-dialkyl-substituted amido.

The term "heteroaryl" means a 5- and 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A heteroaryl is optionally substituted. Exemplary substituents include alkyl, alkoxy, alkylthio, alkylsulfonyl, halogen, trifluoromethyl, dialkylamino, nitro, cyano, CO$_2$H, CONH$_2$, N-monoalkyl-substituted amido and N,N-dialkyl-substituted amido, or by oxo to form an N-oxide.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, dihydropyridine, tetrahydropyridine, piperazine, 1-(2,2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1,6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl. A heterocyclyl can be optionally substituted with 1-4 substituents. Exemplary substituents include alkyl, haloalkyl, halogen and oxo.

The term "alkoxy group" (also herein referred to as "alkoxy") as used herein, refers to an alkyl-O— group or a cycloalkyl-O— group, where the preferred alkyl and cycloalkyl groups and optional substituents thereon are those given above. An alkoxy group can be unsubstituted or substituted with one or more substituents.

The term "alkenyl group" (also herein referred to as "alkenyl") as used herein, refers to a straight chain or branched hydrocarbyl group which includes one or more double bonds. Typically, an alkenyl group includes between 2 and 12 carbon atoms (i.e., ($C_2$-$C_{12}$)-alkenyl). Suitable alkenyl groups include but are not limited to n-butenyl, cyclooctenyl and the like. An alkenyl group can be unsubstituted or substituted with one or more substituents.

The term "alkynyl" group (also herein referred to as "alkynyl") as used herein, refers to a straight chain or branched hydrocarbyl group which includes one or more triple bonds. The triple bond of an alkynyl group can be unconjugated or conjugated to another unsaturated group. Suitable alkynyl groups include, but are not limited to, ($C_2$-$C_8$)-alkynyl groups, such as ethynyl, propynyl, butynyl, pentynyl, hexynyl, methylpropynyl, 4-methyl-1-butynyl, 4-propyl-2-pentynyl-, and 4-butyl-2-hexynyl. An alkynyl group can be unsubstituted or substituted with one or more substituents.

The term "alkylene group" (also herein referred to as "alkylene) as used herein, refers to a group represented by —[$CH_2$]$_z$—, wherein z is a positive integer, preferably from one to eight, more preferably from one to four.

The terms "cycloalkyl alkyl", "alkoxy alkyl" and the like, that is, terms that consist of a combination of terms as defined above refer to groups that contain the groups referred to by the terms. For example, a ($C_a$-$C_b$)alkoxy($C_c$-$C_d$)alkyl is a group that includes an alkoxy group with between a and b carbon atoms that is covalently bonded to an alkyl group with between c and d carbon atoms.

The above groups can be unsubstituted or optionally substituted. Suitable substituents are those which do not substantially interfere with the reactions described herein, that is, that do not substantially decrease the yield (e.g., a decrease of greater than 50%) or cause a substantial amount of by-product formation (e.g., where by-products represent at least 50% of the theoretical yield). However, "interfering" substituents can be used, provided that they are first converted to a protected form. Suitable protecting groups are known in the art and are disclosed, for example, in Greene and Wuts, "Protective Groups in Organic Synthesis", John Wiley & Sons (2007).

Suitable substituents for above groups include, for example, unless otherwise indicated, ($C_1$-$C_4$)alkyl, ($C_1$-$C_4$) alkoxy, ($C_1$-$C_4$)alkoxycarbonyl, benzyloxycarbonyl, hydroxy($C_1$-$C_4$)alkyl, cyano($C_1$-$C_4$)alkyl, ($C_1$-$C_4$)alkylamino, di($C_1$-$C_4$)alkylamino, halogen, cyano, oxo, nitro, hydroxy, amino, $MeSO_2$—, $MeSO_2N(Me)(C_1$-$C_4$)alkyl, $MeSO_2NH(C_1$-$C_4$)alkyl, $H_2NC(\!=\!O)CMe_2(C_1$-$C_4$)alkyl, $H_2NC(\!=\!O)CHMe(C_1$-$C_4$)alkyl, $H_2NC(\!=\!O)CH_2(C_1$-$C_4$) alkyl, —OR, —$NR_2$, —COOR, —$CONR_2$, —$SO_kR$ (k is 0, 1 or 2), wherein each R is independently —H, an alkyl group, a cycloalkyl group or an aryl group.

When a disclosed compound or its pharmaceutically acceptable salt is named or depicted by structure, it is to be understood that solvates or hydrates of the compound or its physiologically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

Protecting groups for an hydroxyl group —OH and reactions and conditions for protecting and deprotecting the hydroxyl group are well known in the art and are disclosed, for example, in Greene and Wuts, "Protective Groups in Organic Synthesis", John Wiley & Sons (2007), Chapter 2 and references cited therein. For example, a protecting group may protect a hydroxyl group as ether. Such protecting groups include, but are not limited to methyl, methoxymethyl, methylthiomethyl, (phenyldimethylsilyl)methoxymethyl, benzyloxymethyl, p-methoxybenzyloxymethyl, [3,4-dimethoxybenzyl)oxy]methyl, p-nitrobenzyloxymethyl, o-nitrobenzyloxymethyl, [(R)-1-(2-nitrophenyl)ethoxy]methyl, (4-methoxyphenoxy)methyl, guaiacolmethyl, [(p-phenylphenyl)oxy]methyl, t-butoxymethyl, 4-pentenyloxymethyl, siloxymethyl, 2-methoxyethoxymethyl, 2-cyanoethoxymethyl, bis(2-chloroethoxy)methyl, 2,2,2-trichloroethoxymethyl, 2-(trimethylsilyl)ethoxymethyl, menthoxymethyl, O-bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl, S,S-dioxide, 1-[(2-chloro-4-methyl)phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, 2,3,3a,4,5,6,7,7a-octahyrdo-7,8,8-trimethyl-4,7-methanobenzofuran-2-yl, 1-ethoxyethyl, 1-(2-chloroethoxy)ethyl, 2-hydroxyethyl, 2-bromoethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1,-dianisyl-2,2,2,-trichloroethyl, 1,1,1,3,3,3-hexafluoro-2-phenylisopropyl, 1-(2-cyanoethoxy)ethyl, 2-trimethylsilylethyl, 2-(benzylthio)ethyl, 2-(phenylselenyl)ethyl, t-butyl, cyclohexyl, 1-methyl-1'-cyclopropylmethyl, allyl, prenyl, cinnamyl, 2-phenallyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, 2,6-difluorobenzyl, p-cyanobenzyl, fluorosbenzyl, 4-fluorousalkoxybenzyl, trimethylsilylxylyl, p-phenylbenzyl, 2-phenyl-2-propyl (cumyl), p-acylaminobenzyl, p-azidobenzyl, 4-azido-3-chlorobenzyl, 2- and 4-trifluoromethylbenzyl, p-(methylsulfinyl)benzyl, p-siletanylbenzyl, 4-acetoxybenzyl, 4-(2-trimethylsilyl)ethoxymethoxybenzyl, 2-naphthylmethyl, 2- and 4-picolyl, 3-methyl-2-picolyl N-oxido, 2-quinolinylmethyl, 6-methoxy-2-(4-methylphenyl)-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, tris(4-t-butylphenyl)methyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"tris(benzoyloxyphenyl)methyl, 4,4'-dimethoxy-3"-[N-(imidazolylmethyl)trityl, 4,4'-dimethoxy-3"-[N-(imidazolylethyl)carbamoyl]trityl, bis(4-methoxyphenyl)-1'-pyrenylmethyl, 4-(17-tetrabenzo[a,c,g,i]fluorenylmethyl)-4,4"-dimethoxytrityl, 9-anthryl, 9-(9-phenyl)xanthenyl, 9-phenylthioxanthyl, 9(9-phenyl-10-oxo)anthryl, 1,3-benzodithiolan-2-yl, 4,5-bis(ethoxycarbonyl-[1,3]-dioxolan-2-yl, benzisothiazolyl S,S-dioxido, trimethylsilyl, triethylsilyl, triisopropylsilyl, dimethylisopropylsiyl, diethylisopropylsilyl, dimethylthexylsilyl, 2-norbornyldimethylsily, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, sisyl, (2-hydroxystyryl)dimethylsilyl, (2-hydroxystyryl)diisopropylsily, t-butylmethoxyphenylsilyl, t-butoxydiphenylsilyl, 1,1,3,3-tetraisopropyl-3-[2-(triphenylmethoxy)ethoxy]disiloxane-1-yl, fluorous silyl. Alternatively, suitable protecting groups protect the hydroxyl group as esters, for example, formate, benzoylformate, acetate, chloroacetate, dichloroacetate, trichloroacetate, trichloroacetamidate, trifluoroacetate, methoxyacetate, triphenylmethoxyacetate, phenoxyacetate, p-chlorophenoxyacetate, phenylacetate, p-P-phenylacetate, diphenylacetate, 3-phenylpropionate, bisfluorous chain type propanoyl (Bfp-OR), 4-pentenoate, 4-oxopentanoate (levulinate), 4,4-(ethylenedithio)pentanoate, 5-[3-Bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate (mesitoate), 4-bromobenzoate, 2,5-difluorobenzoate, p-nitrobenzoate, picolinate, nicotinate, 2-(azidomethyl)benzoate, 4-azidobutyrate, (2-azidomethyl)phenylacetate, 2-{[(tritylthio)oxy]methyl}benzoate, 2-{[(4-methoxytritylthio)oxy]methyl}benzoate, 2-{[methyl(tritylthio)amino]methyl}benzoate, 2{{[4-methoxytrityl)thio]methylamino}-methyl}benzoate, 2-(allyloxy)phenylacetate, 2-(prenyloxymethyl)benzoate, 6-(levulinyloxymethyl)-3-methoxy-2- and 4-nitrobenzoate, 4-benzyloxybutyrate, 4-trialkylsiloxybutrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzenesulfonate, 4-methylthiomethoxy)butyrate, 2-methylthiomethoxymethyl)benzoate, 2-(chloroacetoxymethyl)benzoate, 2[(2-chloroacetoxy)ethyl]benzoate, 2-[2-(benzyloxy)ethyl]benzoate, 2-[2-(4-methoxybenzyloxy)ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate tiglorate), o-(methoxycarbonyl)benzoate, p-P-benzoate, α-naphthoate, nitrate, alkyl N,N,N',N'-tetramethylphosphorodiamidate, 2-chlorobenzoate, as sulfonates, sulfenates and sulfinates such as sulfate, allylsulfonate, ethanesulfonate (mesylate), benzylsulfonate, tosylate, 2-[(4-nitrophenyl)ethyl]sulfonate, 2-trifluoromethylsulfonate, 4-monomethoxytritylsulfenate, alkyl 2,4-initrophenylsulfenate, 2,2,5,5-tetramethylpyrrolidin-3-one-1-sulfinate, borate, dimethylphosphinothioyl, as carbonates such as alkyl methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethypsilyl]ethyl carbonate, 2-(phenylsulfonyl)ethyl carbonate, 2-(triphenylphosphonio)ethyl carbonate, cis-[4-[[(-methoxytrityl)sulfenyl]oxy]tetraydrofuran-3-yl]oxy carbonate, isobutyl carbonate, t-butyl carbonate, vinyl carbonate, allyl carbonate, cinnamyl carbonate, propargyl carbonate, p-chlorophenyl carbonate, p-nitrophenyl carbonate, 4-ethoxyl-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-ylmethyl carbonate, 2-dansylethyl carbonate, 2-(4-nitrophenyl)ethyl, 2-(2,4-nitrophenyl)ethyl, 2-(2-nitrophenyl)propyl, 2-(3,4-methylenedioxy-6-nitrophenylpropyl, 2-cyano-1-phenylethyl carbonate, 2-(2-pyridyl)amino-1-phenylethyl carbonate, 2-[N-methyl-N-(2-pyridyl)]amino-1-phenylethyl carbonate, phenacyl carbonate, 3',5'-dimethoxybenzoin carbonate, methyl dithiocarbonate, S-benzyl thiocarbonate, and carbamates such as dimethylthiocarbamate, N-phenylcarbamate, and N-methyl-N-(o-nitrophenyl) carbamate.

Protecting groups for a carbonyl group and reactions and conditions for protecting and deprotecting the carbonyl group are well known in the art and are disclosed, for example, in Greene and Wuts, "Protective Groups in Organic Synthesis", John Wiley & Sons (2007), Chapter 4 and references cited therein. For example, a protecting group may protect a carbonyl group as acetal or ketal. These acetals and ketals include acyclic acetals and ketals (e.g., dimethyl, diisopropyl, bis(2,2,2-trichloroethyl), cyclic acetals and ketals (e.g., 1,3-dioxanes, 1,3-dioxolanes, 1,3-dioxapane and the like), chiral acetals and ketals (e.g., (4R,5R)-diphenyl-1,3-dioxolane, 4,5-dimethyl-1,3-dioxolane, trans-1,2-cyclohexanediol ketal and the like), dithio acetals and ketals (e.g., S,S'-dimethyl, S,S'-diethyl, S,S'-dipropyl, 1,3-dithiane and the like), and monothio acetals and ketals.

Protecting groups for a carboxyl group and reactions and conditions for protecting and deprotecting the carboxyl group are well known in the art and are disclosed, for example, in Greene and Wuts, "Protective Groups in Organic Synthesis", John Wiley & Sons (2007), Chapter 5 and references cited therein. For example, a protecting group may protect a carboxyl group as ester. These esters include, but are not limited to substituted methyl esters (e.g., 9-fluorenylmethyl, methoxymethyl, methoxyethoxymethyl and the like), 2-substituted ethyl esters (e.g., 2,2,2-trichloroethyl, 2-haloethyl, 2-(trimethylsilyl)ethyl and the like), 2,6-dialkylphenyl esters (e.g., 2,6-dimethylphenyl, 2,6-di-t-butyl-4-methylphenyl, pentafluorophenyl and the like), substituted benzyl esters (e.g., triphenylmethyl, diphenylmethyl, 9-anthrylmethyl and the like), silyl esters (e.g., trimethylsilyl, triethylsilyl, t-butyldimethylsilyl and the like. Alternatively, for example, a protecting group may protect a carboxyl group as amide (e.g., N,N-dimethyl, pyrrolidinyl, piperidinyl and the like) or hydrazide (e.g., N-phenyl).

Protecting groups for an amino group and reactions and conditions for protecting and deprotecting the amino group are well known in the art and are disclosed, for example, in Greene and Wuts, "Protective Groups in Organic Synthesis", John Wiley & Sons (2007), Chapter 7 and references cited therein. For example, a protecting group may protect an amino group as carbamate (e.g., 9-fluorenylmethyl, 2,2,2-trichloroethyl, 4-phenylacetoxybenzyl, 2-methylthioethyl, m-nitrophenyl, and the like) or amide (e.g., formamide, acetamide, 3-phenylpropanamide).

Protecting groups for an aromatic heterocycle such as, for example, imidazole, pyrrole, and indole, and reactions and conditions for protecting and deprotecting the aromatic heterocycles are well known in the art and are disclosed, for example, in Greene and Wuts, "Protective Groups in Organic Synthesis", John Wiley & Sons (2007), Chapter 7 and references cited therein. For example, a protecting group may protect an aromatic heterocycle as N-sulfonyl derivative (e.g., N,N-dimethylsulfonamide, methanesulfoneamide, mesitylenesulfonamide and the like), carbamate (e.g., benzyl, 2,2,2-trichloroethyl, 2-(trimethylsilyl)ethyl and the like), N-alkyl and N-aryl derivatives, N-trialkylsilyl, N-allyl, N-benzyl, amino acetal derivative, or amide.

Protecting groups for an amide group, and reactions and conditions for protecting and deprotecting the amide group are well known in the art and are disclosed, for example, in Greene and Wuts, "Protective Groups in Organic Synthesis", John Wiley & Sons (2007), Chapter 7 and references cited therein. For example, a protecting group may protect an amide group as N-methylamide, N-allylamide, N-t-butylamide and the like.

Protecting groups for a sulfonamide group, and reactions and conditions for protecting and deprotecting the sulfonamide group are well known in the art and are disclosed, for example, in Greene and Wuts, "Protective Groups in Organic Synthesis", John Wiley & Sons (2007), Chapter 7 and references cited therein. For example, a protecting group may protect a sulfonamide group as N-t-butylsulfonamide, N-diphenylmethylsulfonamide, N-benzylsulfonamide and the like. A description of example embodiments of the invention follows.

The following abbreviations have the indicated meanings:

| Abbreviation | Meaning |
| --- | --- |
| A % | Area percentage |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| c-Pr | cyclopropyl |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIBAL-H | diisobutylaluminum hydride |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| dr | diastereomer ratio |
| EDC•HCl, EDCI | 1-[3-(dimethylamino)propyl]-3-ethylcarbodiimide hydrochloride |
| Equiv | equivalents |
| EtOAc | ethyl acetate |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |

-continued

| Abbreviation | Meaning |
|---|---|
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| m-CPBA | meta-chloroperoxybenzoic acid |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| rt | room temperature |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| T$_{ext}$ | External temperature |
| T$_{int}$ | Internal temperature |
| TFA | trifluoroacetic acid |
| Tlc, TLC | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |

EXEMPLIFICATION

Synthesis of Compound 8 of FIG. 1

FIG. 1 shows a preferred synthesis of a specific tertiary alcohol oxazinone compound (compound 8) known to be a 11β-HSD1 inhibitor. Compounds 3 to 8 of FIG. 1 were synthesized as described in Examples 1 to 4.

Example 1

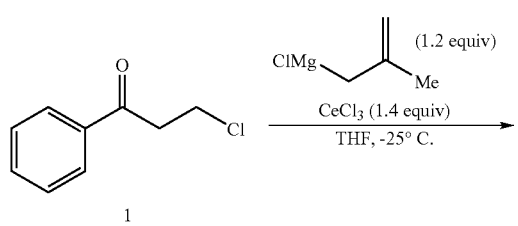

1

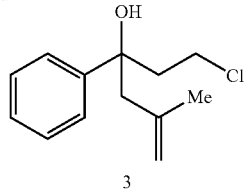

3

1-Chloro-5-methyl-3-phenyl-hex-5-en-3-ol (3). To a stirred suspension of magnesium turnings (46.7 g, 1.94 mol) in 1500 mL of THF (KF<100 ppm) was charged 53.0 mL of 1 M DIBAL-H in hexane under nitrogen at room temperature. Then beta-methylallylic chloride (160 g, 1.77 mol) was introduced while maintaining the internal temperature below 30° C. The resulting solution was agitated for 2 h at room temperature. The solution was titrated in the presence of 1,1'-bipyridine to indicate 0.8 M of the corresponding Grignard reagent. To a dry flask containing 307.0 g of anhydrous CeCl$_3$ (1.25 mol) at room temperature under nitrogen was added 1556.8 mL of the Grignard reagent (0.8 M, 1.25 mol). The resulting slurry was cooled to −10° C. and agitated for 0.5 h. To the slurry was added 200 g of the ketone (1.19 mol) in 200 mL of THF while maintaining the internal temperature below 0° C. After the mixture was stirred for 0.5 h, 1200 mL of 1 M HCl was added to obtain a clear solution while maintaining the internal temperature below 30° C. After the phase cut, the aqueous layer was extracted with EtOAc (500 mL). The combined organic layers were washed with brine and dried over sodium sulfate. Removal of the solvent under vacuum produced the crude product, which was chased with THF to achieve KF<500 ppm. The crude product (306 g, 83 wt %, 95% yield) was used directly for subsequent coupling. Analytical data for 3: $^1$H-NMR spectroscopy (500 MHz, CDCl$_3$) δ 7.38-7.37 (d. J=7.8 Hz, 2H), 7.33 (t, 7.9 Hz, 2H), 7.24 (t, J=7.4 Hz, 1H), 4.91 (s, 1H), 4.76 (s, 1H), 3.57 (ddd, J=5.6, 10.7, and 10.7, 1H), 3.13 (ddd, J=4.7, 10.7 and 10.7 Hz, 1H), 2.66 (d, J=13.3 Hz, 1H), 2.54 (d, J=11.3 Hz, 1H), 2.53 (s, 1H), 2.36 (ddd, J=5.4, 10.6 and 13.9 Hz. 1H), 2.29 (ddd, J=5.6, 11.3 and 13.3 Hz, 1H), 1.29 (s, 3H). $^{13}$C-NMR spectroscopy (125 MHz, CDCl$_3$) δ 144.3, 141.4, 128.0, 126.6, 124.8, 116.1, 74.2, 51.2, 46.0, 39.9, 23.9.

Example 2

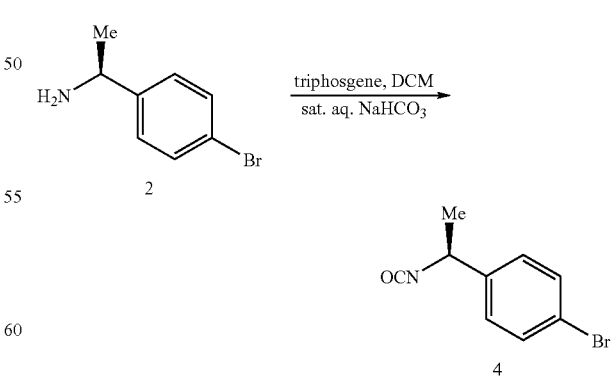

1-Bromo-4-((S)-1-isocyanato-ethyl)-benzene (4). To a 10 L jacketed reactor was charged 241 g of sodium bicarbonate (2.87 mol, 2.30 equiv) and 5 L of deionized water. The resulting solution was agitated for 10-20 min, until the solids dissolved (homogeneous). To the clear solution was charged 250 g (1.25 mol, 1.00 equiv) of (S)-(−)-1-(4-bromophenyl)ethylamine as a solution in 1.00 L of dichloromethane. An additional 4 L of dichloromethane was charged to the reactor. The biphasic solution was agitated and cooled to $T_{int}$=2-3° C. Triphosgene (126 g, 424 mmol, 0.340 equiv) was charged to the reactor in approximately two equal portions ~6 min apart. It should be noted that a slight exotherm was noted upon the addition of triphosgene. The resulting murky solution was agitated at $T_{int}$=2-5° C. for 30 min, at which point HPLC analysis indicates >99 A % conversion (220 nm). The dichloromethane layer was cut and dried with anhydrous sulfate. The resulting solution was passed through a celite plug and concentrated to ~1.5 L which fine particles of a white solid developed. The solution was filtered and concentrated to a thick oil via reduced pressure to produce 239 g of product (93.7 wt %, 79.4% yield). The material was used in the following coupling without further purification. Analytical data for 4: $^1$H-NMR spectroscopy (400 MHz, CD2Cl2) δ 7.53 (d, J=11.4 Hz, 2H), 7.26 (d, J=8.2 Hz, 2H), 4.80 (q, J=6.7 Hz, 1H), 1.59 (d, J=6.7 Hz, 3H).

Example 3

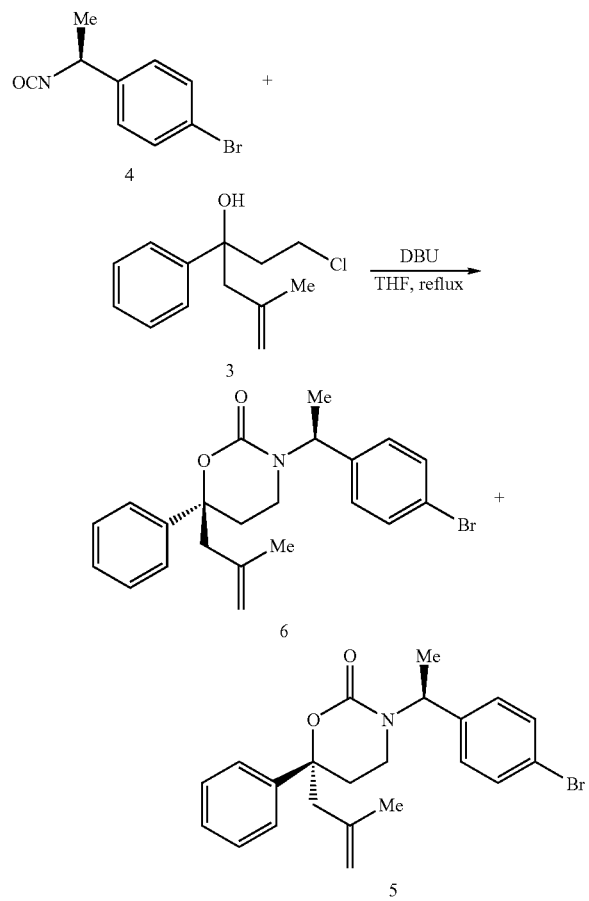

(R)-3-[(S)-1-(4-Bromo-phenyl)-ethyl]-6-(2-methyl-allyl)-6-phenyl-perhydro-1,3-oxazin-2-one (6) To a dried 10 L jacketed reactor under a nitrogen atmosphere was charged 1-chloro-5-methyl-3-phenyl-hex-5-en-3-ol (3, 167 g, 81.7 wt %, 610 mmol, 1.00 equiv), 1-bromo-4-((S)-1-isocyanato-ethyl)-benzene (4, 219 g, 93.7 wt %, 911 mmol, 1.50 equiv), anhydrous tetrahydrofuran (3.00 L), and then 1,8-diazabicyclo[5.4.0]undec-7-ene (DBU, 409 mL, 2.73 mol, 4.50 equiv). The resulting solution was agitated and refluxed ($T_{int}$=67-69° C., $T_{ext}$=75° C.) for 19 h, at which point HPLC analysis indicates ~1A % (220 nm) of the 1-chloro-5-methyl-3-phenyl-hex-5-en-3-ol (3) remains. The dark solution was cooled to Tint=20-25° C. Two liters of tetrahydrofuran were removed by distillation under reduced pressure. The remaining dark solution was diluted with 4.0 L of ethyl acetate and 1.0 L of hexanes. The resulting solution was washed with 4.0 L of a 1.0 M aqueous solution of hydrogen chloride (note: the wash is slightly exothermic). The aqueous solution was cut and the remaining organic solution was dried with anhydrous sodium sulfate, filtered and then concentrated to an oil via reduced pressure. The resulting material was subjected to flash silica chromatography (5-30% ethyl acetate/hexanes, 1.74 kg of silica) to produce 137.8 g of material (59 wt %, 3.1:1 diastereomeric ratio favoring the desired diastereomer 6, 32.3% yield). The material was used in the following epoxidation without further purification.

Analytical data for (R)-3-[(S)-1-(4-bromo-phenyl)-ethyl]-6-(2-methyl-allyl)-6-phenyl-perhydro-1,3-oxazin-2-one (6): $^1$H-NMR spectroscopy (500 MHz, CD2Cl2) δ 7.42-7.35 (m, 3H), 7.33-7.31 (m, 2H), 7.25-7.23 (m, 2H), 6.80-6.74 (m, 2), 5.55 (q, J=7.1 Hz, 1H), 5.37-5.36 (m, 1H), 4.89 (s, 1H), 4.69 (s, 1H), 2.96-2.93 (m, 1H), 2.61 (dd, J=13.8 and 26.4 Hz, 2H), 2.37-2.25 (m, 3H), 1.68 (s, 3H), 1.50 (d, J=7.1 Hz, 3H). $^{13}$C-NMR spectroscopy (125 MHz, CD2Cl2) δ 152.5, 141.5, 140.1, 138.3, 130.6, 128.1, 128.0, 126.9, 124.4, 120.2, 115.3, 82.4, 52.1, 50.1, 35.6, 29.8, 23.4, 14.5.

Analytical data for (S)-3-[(S)-1-(4-bromo-phenyl)-ethyl]-6-(2-methyl-allyl)-6-phenyl-perhydro-1,3-oxazin-2-one (5): $^1$H-NMR spectroscopy (400 MHz, CD2Cl2) δ 7.50-7.48 (m, 2H), 7.43-7.39 (m, 2H), 7.35-7.32 (m, 3H), 7.20-7.18 (m, 2H), 5.60 (q, J=7.1 Hz, 1H), 4.85 (s, 1H), 4.66 (s, 1H), 2.73-2.67 (m, 2H), 2.60 (dd, J=13.9 and 19.4 Hz, 2H), 2.28 (dt, J=3.3 and 13.7 Hz, 1H), 2.14-2.05 (m, 1H), 1.66 (s, 3H), 1.24 (d, J=7.2 Hz, 3H). $^{13}$C-NMR spectroscopy (100 MHz, CD2Cl2) δ 153.4, 142.5, 141.0, 140.1, 131.8, 129.3, 128.9, 127.8, 125.3, 121.5, 116.3, 83.9, 53.2, 51.0, 36.6, 31.3, 24.3, 15.4.

Example 4

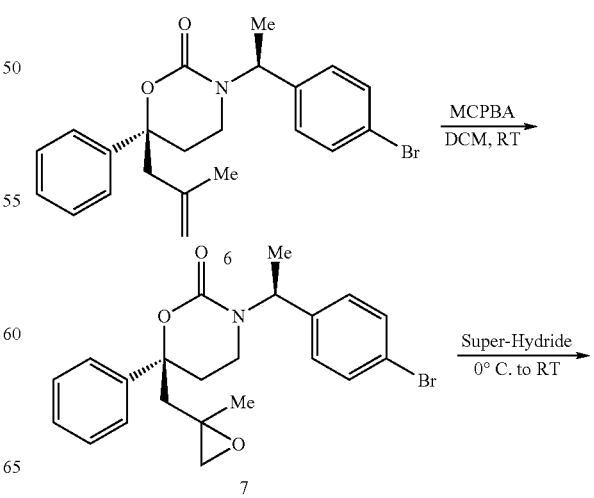

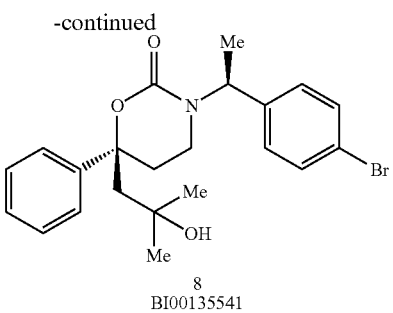

8
BI00135541

(S)-3-[(S)-1-(4-Bromo-phenyl)-ethyl]-6-(2-hydroxy-2-methyl-propyl)-6-phenyl-perhydro-1,3-oxazin-2-one (8; BI00135541). To a 1.0 L 2-neck RBF was charged (R)-3-[(S)-1-(4-bromo-phenyl)-ethyl]-6-(2-methyl-allyl)-6-phenyl-perhydro-1,3-oxazin-2-one (6, 135.8 g, 59 wt %, 3.1:1 dr, 193 mmol, 1.00 equiv), dichloromethane (700 mL), and then 3-chloroperbenzoic acid (MCPBA, 70%, 95.3 g, 386 mmol, 2.0 equiv). The resulting solution was agitated at RT ($T_{int}$=20-25° C.) for 1 h, which HPLC analysis indicates >99 A % (220 nm) conversion. The resulting solution was diluted with 700 mL of methyl tert-butyl ether (MTBE) and washed with 1×500 mL of 30 wt % solution of sodium thiosulfate and 1×500 mL of saturated aqueous solution of sodium bicarbonate. The wash sequence were repeated until the peak on an HPLC trace of the organic solution that corresponds to a HPLC sample peak of MCPBA is <2.5 A % (220 nm), which in this example the wash sequence was repeated 3 times. The resulting organic layer was dried with anhydrous sodium sulfate, filtered and then concentrated to an oil via reduced pressure. The resulting material was diluted with 200 mL of anhydrous tetrahydrofuran and then concentrated to a thick oil via reduced pressure to provide (S)-3-[(S)-1-(4-bromo-phenyl)-ethyl]-6-(2-methyl-oxiranylmethyl)-6-phenyl-perhydro-1,3-oxazin-2-one (7) which was used directly in the following reduction.

To a 2.0 L 3-neck oven-dried RBF was charged the crude (S)-3-[(S)-1-(4-bromo-phenyl)-ethyl]-6-(2-methyl-oxiranyl-methyl)-6-phenyl-perhydro-1,3-oxazin-2-one (7) and 750 mL of anhydrous tetrahydrofuran. The resulting solution was agitated and cooled to $T_{int}$=2-3° C. To the agitated clear solution was charged 1.0 M lithium triethylborohydride in tetrahydrofuran (Super Hydride, 348 mL, 348 mmol, 1.8 equiv). The addition is exothermic and addition controlled to maintain $T_{int}$=<8° C. The resulting solution was agitated at $T_{int}$=2-3° C. for 1.5 h and then allowed to warm to $T_{int}$=10-13° C. over a 2.5 h, which HPLC analysis indicates ~94 A % (220 nm) conversion. To the agitated solution was charged a solution of hydrogen peroxide (95.7 mL of a 35 wt % aqueous solution diluted with 400 mL of water, 1.08 mol, 5.60 equiv). The addition is highly exothermic and addition controlled to maintain $T_{int}$=<25° C. The resulting solution was diluted with 1.00 L of methyl tert-butyl ether (MTBE) and washed with 1.00 L of water followed by 500 mL of a ~30 wt % solution of sodium thiosulfate. The organic solution was dried with anhydrous sodium sulfate, filtered, and then concentrated via reduced pressure. The resulting material was subjected to flash silica chromatography (10-60% ethyl acetate, 600 g of silica) to produce 68 g of material consisting of both diastereomers (1.98:1 dr) and 41 g of the desired diastereomer (>99:1 dr). The material consisting of the mixed fractions was recrystallized from 250 mL of isopropyl acetate (IPAC) and 200 mL of heptane (anti-solvent) to produce upon filtration 31.3 g of product (95.7 A % at 220 nm, 74:1 dr). The two samples were combined to produce 72.3 g of product (83.6% yield for the two step operation). Analytical data for 8: $^1$H-NMR spectroscopy (400 MHz, $CDCl_3$) δ 7.37-7.29 (m, 5H), 7.25-7.21 (m, 2H), 6.82-6.79 (m, 2H), 5.61 (q, J=6.9 Hz, 1H), 2.83 (ddd, J=2.5, 5.4 and 11.6 Hz, 1H), 2.39 (ddd, J=5.7, 12.0 and 14.1 Hz, 1H), 2.27 (ddd, J=2.6, 4.8 and 14.0 Hz, 1H), 2.21-2.14 (m, 3H), 2.08 (s, 1H), 1.49 (d, J=7.0 Hz, 3H), 1.18 (s, 3H), 1.13 (s, 3H). $^{13}$C-NMR spectroscopy (100 MHz, $CDCl_3$) δ 153.2, 142.6, 138.5, 131.6, 129.13, 129.10, 128.0, 125.3, 121.6, 84.2, 71.4, 54.1, 53.3, 36.4, 33.6, 32.1, 30.8, 15.6.

Synthesis of Oxazinones: Reaction of a β-haloalcohol and an isocyanate

Example 5

6-allyl-6-(4-fluorophenyl)-3-((S)-1-phenylethyl)-1,3-oxazinan-2-one

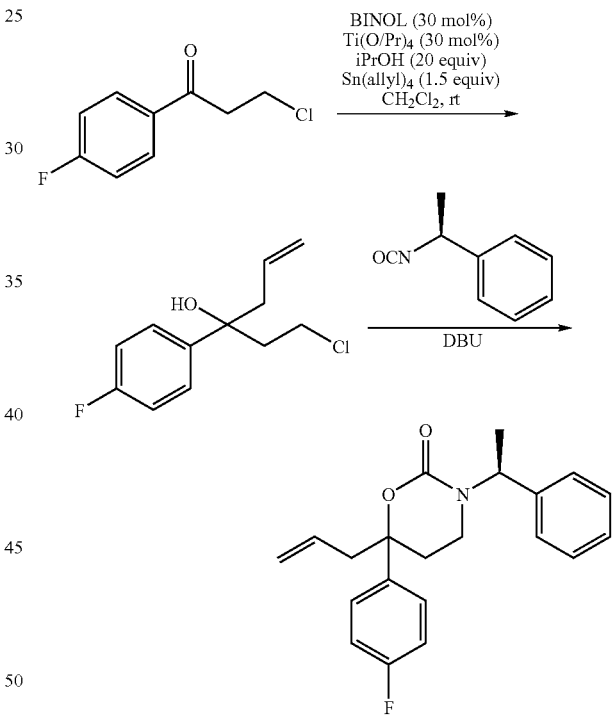

Step 1. 1-Chloro-3-(4-fluorophenyl)hex-5-en-3-ol

To a solution of 1,1'-bi-2-naphthol (0.2280 g, 0.80 mmol, 0.26 equiv), $CH_2Cl_2$ (5 mL) and titanium(IV) isopropoxide (0.2243 g, 0.79 mmol, 0.26 equiv) were added 2-propanol (3.1620 g, 52.6 mmol, 17 equiv), tetraallylstannane (1.2538 g, 4.43 mmol, 1.43 equiv), and 3-chloro-1-(4-fluorophenyl)propan-1-one (0.5760 g, 3.09 mmol, 1.0 equiv) successively. The reaction mixture was stirred at rt under nitrogen for 22 h. The reaction was quenched with satd aq $NH_4Cl$ and extracted with EtOAc. The organic layer was dried over $Na_2SO_4$. After the solvents were evaporated, the residue was purified by chromatography on silica gel eluted with hexanes/ethyl acetate to afford 1-chloro-3-(4-fluorophenyl)hex-5-en-3-ol as an oil.

Step 2. 6-Allyl-6-(4-fluorophenyl)-3-((S)-1-phenylethyl)-1,3-oxazinan-2-one

A mixture of 1-chloro-3-(4-fluorophenyl)hex-5-en-3-ol (0.0889 g, 0.39 mmol, 1.0 equiv), (S)-(−)α-methylbenzyl isocyanate (0.0823 g, 0.56 mmol, 1.44 equiv), and DBU (0.1397 g, 0.92 mmol, 2.36 equiv) in THF (2 mL) was heated to reflux for 17 h. After the solvent was removed, the residue was purified by chromatography on silica gel eluted with hexanes/ethyl acetate to give 0.0990 g (75%) of the product as a mixture of diastereomers. Selected fractions contained the individual diastereomers.

Isomer 1: (R)-6-allyl-6-(4-fluorophenyl)-3-((S)-1-phenylethyl)-1,3-oxazinan-2-one. LC-MS Method 1, $t_R$=1.89 min, m/z=340 (M+1). $^1$H NMR (CDCl$_3$) 7.36-7.27 (m, 7H), 7.10-7.05 (m, 2H), 5.79-5.67 (m, 2H), 5.09-4.98 (m, 2H), 2.72-2.68 (m, 2H), 2.64-2.53 (m, 2H), 2.22-2.16 (m, 1H), 2.09-2.01 (m, 1H), 1.26 (d, J=7.3 Hz, 3H).

Isomer 2: (S)-6-allyl-6-(4-fluorophenyl)-3-((S)-1-phenylethyl)-1,3-oxazinan-2-one. LC-MS Method 1, $t_R$=1.86 min, m/z=340 (M+1). $^1$H NMR (CDCl$_3$) 7.29-7.24 (m, 2H), 7.14-7.08 (m, 3H), 7.05-7.00 (m, 2H), 6.88-6.85 (m, 2H), 5.77-5.63 (m, 2H), 5.10-5.00 (m, 2H), 2.93-2.88 (m, 1H), 2.65-2.52 (m, 2H), 2.32-2.17 (m, 3H), 1.51 (d, J=7.0 Hz, 3H).

Example 6

6-allyl-3-((S)-1-(4-bromophenyl)ethyl)-6-(4-fluorophenyl)-1,3-oxazinan-2-one with hexanes/ethyl acetate to afford of 1-chloro-3-(4-fluorophenyl)hex-5-en-3-ol (3.0049 g, 97%) as an oil. LC-MS Method 1 $t_R$=1.79 min, m/z 213, 211 (M-OH)$^+$; $^1$H NMR (400 MHz, CDCl$_3$) δ 7.37-7.32 (m, 2H), 7.07-7.02 (m, 2H), 5.57-5.47 (m, 1H), 5.20-5.19 (m, 1H), 5.16 (m, 1H), 3.59-3.52 (m, 1H), 3.24-3.18 (m, 1H), 2.70 (dd, J=13.8, 5.9 Hz, 1H), 2.50 (dd, J=13.8, 8.5 Hz, 1H), 2.29 (t, J=7.9 Hz, 2H), 2.22 (s, 1H); $^{19}$F NMR (376 MHz, CDCl$_3$) δ −116.52 (m).

Step 2. (R)-6-allyl-3-((S)-1-(4-bromophenyl)ethyl)-6-(4-fluorophenyl)-1,3-oxazinan-2-one and (S)-6-allyl-3-((S)-1-(4-bromophenyl)ethyl)-6-(4-fluorophenyl)-1,3-oxazinan-2-one A mixture of 1-chloro-3-(4-fluorophenyl)hex-5-en-3-ol (0.4129 g, 1.8 mmol, 1.0 equiv), (S)-(−)-1-(4-bromophenyl)ethyl isocyanate (0.5005 g, 2.2 mmol, 1.2 equiv), and DBU (0.7375 g, 4.8 mmol, 2.7 equiv) in THF (10 mL) was heated to reflux for 25 h. The mixture was diluted with EtOAc and washed with 1 N aq HCl. The aqueous phase was extracted with EtOAc (2×). The combined organic phase was dried over Na$_2$SO$_4$. After the solvents were evaporated, the crude product was directly used in the next step without further purification.

An analytical sample was purified by chromatography on silica gel eluted with hexanes/ethyl acetate to afford the two diastereomers of 6-allyl-3-((S)-1-(4-bromophenyl)ethyl)-6-(4-fluorophenyl)-1,3-oxazinan-2-one.

Isomer 1: (S)-6-allyl-3-((S)-1-(4-bromophenyl)ethyl)-6-(4-fluorophenyl)-1,3-oxazinan-2-one. LC-MS Method 1

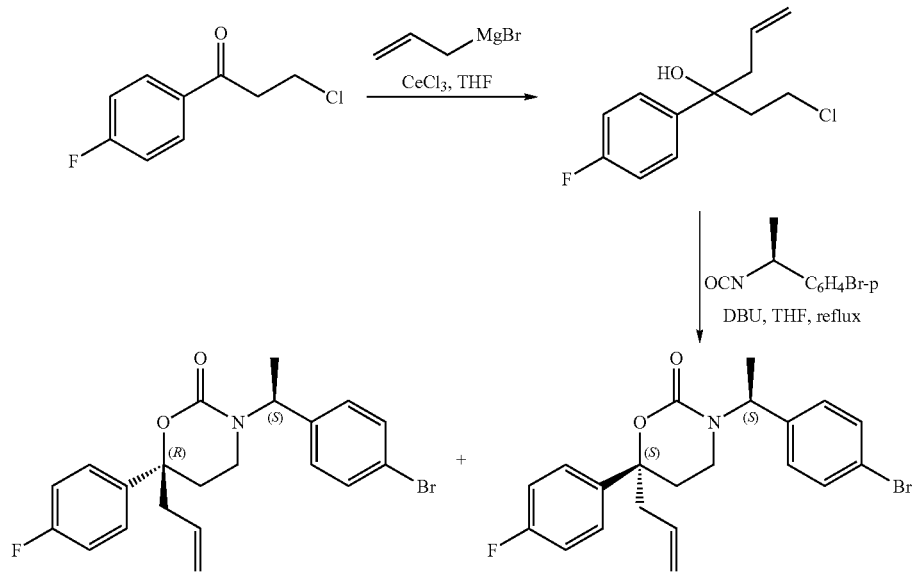

Step 1. 1-chloro-3-(4-fluorophenyl)hex-5-en-3-ol

A 250-mL flask was charged with anhydrous CeCl$_3$ (5.58 g, 22.6 mmol) and THF (40 mL). The mixture was vigorously stirred for 3.5 h at rt. The suspension was then cooled to −78° C. and a solution of allylmagnesium bromide (1.0 M in THF, 21 mL, 21.0 mmol) was added. After stirring for 2 h at −78° C., a solution of 3-chloro-1-(4-fluorophenyl)propan-1-one (2.522 g, 13.5 mmol) in THF (30 mL) was added via cannula. The reaction mixture was allowed to slowly warm to 8° C. while stirring overnight (18 h). The reaction was then quenched with satd aq NaHCO$_3$, extracted with EtOAc, and dried over Na$_2$SO$_4$. After the solvents were evaporated, the residue was purified by chromatography on silica gel eluted $t_R$=2.03 min, m/z 420, 418 (MH$^+$); $^1$H NMR (400 MHz, CDCl$_3$) δ 7.46 (d, J=8.2 Hz, 2H), 7.31-7.28 (m, 2H), 7.17 (d, J=8.2 Hz, 2H), 7.07 (t, J=8.5 Hz, 2H), 5.76-5.66 (m, 2H), 5.10-4.99 (m, 2H), 2.75-2.52 (m, 4H), 2.23-2.19 (m, 1H), 2.08-2.00 (m, 1H), 1.24 (d, J=7.0 Hz, 3H); $^{19}$F NMR (376 MHz, CDCl$_3$) δ −115.07 (m).

Isomer 2: (R)-6-allyl-3-((S)-1-(4-bromophenyl)ethyl)-6-(4-fluorophenyl)-1,3-oxazinan-2-one. LC-MS Method 1 $t_R$=1.98 min, m/z 420, 418 (MH$^+$); $^1$H NMR (400 MHz, CDCl$_3$) δ 7.25-7.20 (m, 4H), 7.05-7.01 (m, 2H), 6.71 (d, J=8.5 Hz, 2H), 5.74-5.64 (m, 1H), 5.58 (q, J=7.0 Hz, 1H), 5.09-4.99 (m, 2H), 2.92-2.87 (m, 1H), 2.63-2.50 (m, 2H), 2.33-2.16 (m, 3H), 1.47 (d, J=7.0 Hz, 3H); $^{19}$F NMR (376 MHz, CDCl$_3$) δ −114.91 (m).

Example 7

6-methyl-6-phenyl-3-m-tolyl-1,3-oxazinan-2-one

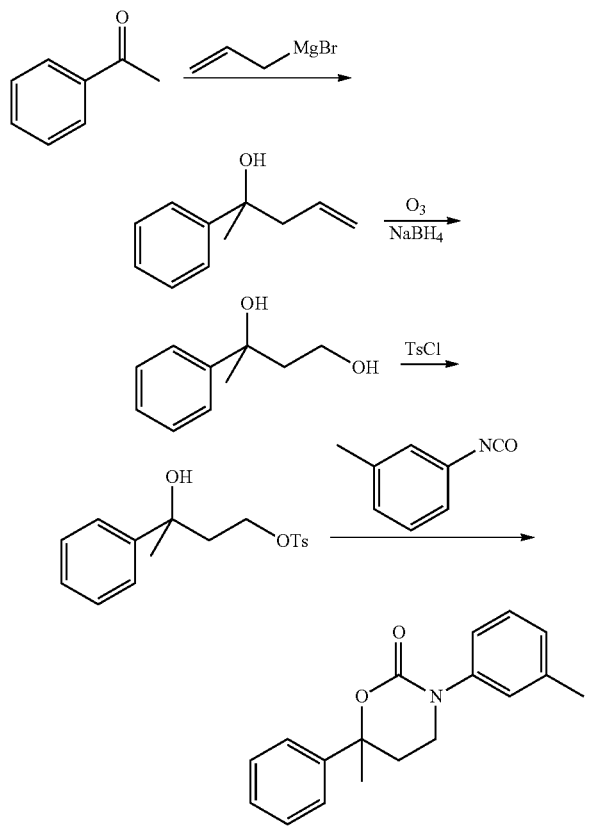

Step 1. 2-Phenylpent-4-en-2-ol

To a solution of acetophenone (30 g, 0.25 mol) in dry THF (250 mL) at −78° C. was added dropwise 1M allylmagnesium bromide (1.25 L, 1.25 mol). After addition was complete, the mixture was allowed to stir at rt for 3 h. The reaction was quenched with satd aq NH$_4$Cl solution (30 mL). The mixture was extracted with EtOAc (200 mL). The organic layer was washed with brine (30 mL), dried over anhydrous Na$_2$SO$_4$ and concentrated to give 2-phenylpent-4-en-2-ol (40.2 g), which was used for the next step without purification.

Step 2. 3-Phenylbutane-1,3-diol

A solution of 2-phenylpent-4-en-2-ol (74 g, 0.457 mol) in dry CH$_2$Cl$_2$ (1 L) was treated with ozone at −78° C. until the mixture turned blue. The system was then flushed with oxygen to remove excess ozone. NaBH$_4$(42.8 g, 1.143 mol) was added to the mixture in portions at −20° C. The mixture was stirred overnight at rt. The mixture was quenched with water and the layers were separated. The aqueous layer was extracted with CH$_2$Cl$_2$ (2×). The organic layers were combined, washed with brine, dried over anhydrous Na$_2$SO$_4$ and concentrated to give 3-phenylbutane-1,3-diol (67.8 g), which was used for the next step without purification.

Step 3. 3-Hydroxy-3-phenylbutyl 4-methylbenzenesulfonate

To a solution of 3-phenylbutane-1,3-diol (68 g, 0.41 mol) in dry CH$_2$Cl$_2$ (500 mL) was added dropwise a solution of TsCl (78 g, 0.41 mol) and triethylamine (71 mL, 0.45 mol) in dry CH$_2$Cl$_2$ (500 mL) at 0° C. The mixture was stirred overnight. The mixture was poured into water and separated. The aqueous layer was extracted with CH$_2$Cl$_2$ (200 mL) twice. The organic layer was combined, washed with brine, dried over anhydrous Na$_2$SO$_4$ and concentrated to give the crude product. The crude product was purified by column chromatography to give 3-hydroxy-3-phenylbutyl 4-methylbenzenesulfonate (62 g, 42%). $^1$H NMR (400 MHz, CDCl$_3$): δ=1.55 (s, 3H), 1.93 (w, 1H), 2.19~2.24 (q, 2H), 2.45 (s, 3H), 3.87~4.01 (m, 1H), 4.09~4.16 (m, 1H), 7.19~7.34 (m, 7H), 7.68~7.76 (d, 2H).

Step 4. 6-methyl-6-phenyl-3-m-tolyl-1,3-oxazinan-2-one

To a solution of 3-hydroxy-3-phenylbutyl 4-methylbenzenesulfonate (1 g, 3.12 mmol) and DBU (1.4 g, 9.26 mmol) in CH$_2$Cl$_2$ (15 mL) was added a solution of 3-methylphenyl isocyanate (623 mg, 4.68 mmol) in CH$_2$Cl$_2$ (5 mL) at 0° C. over 0.5 h. The mixture was stirred at rt overnight. The mixture was concentrated to give the crude product, which was purified by column chromatography and then by preparative HPLC to afford 6-methyl-6-phenyl-3-m-tolyl-1,3-oxazinan-2-one. LC-MS Method 2, t$_R$=2.706 min, m/z=282. $^1$H NMR (CDCl$_3$) 1.75 (s, 3H), 2.30 (s, 3H), 2.35-2.50 (m, 2H), 3.30 (m, 1H), 3.50 (m, 1H), 6.95 (m, 2H), 7.05 (m, 1H), 7.20-7.30 (m, 1H), 7.35 (m, 1H), 7.42-7.50 (m, 4H).

Step 5. Enantiomers of 6-methyl-6-phenyl-3-m-tolyl-1,3-oxazinan-2-one

Chiral preparative SFC using a ChiralPak-AD, 400×25 mm I.D, 20 μm (Daicel Chemical Industries, Ltd) column maintained at 35 C eluted with 70:30 supercritical CO$_2$/0.1% diethylamine in MeOH at a flow rate of 70 mL min$^{-1}$ and a nozzle pressure of 100 bar afforded two isomers.

Isomer 1 (90 mg) gave the following spectral data: $^1$H NMR (400 MHz, CDCl$_3$): δ=1.62 (m, 1H), 1.76 (s, 3H), 2.31 (s, 3H), 2.48 (m, 2H), 3.28 (m, 1H), 3.50 (m, 1H), 6.95 (m, 1H), 7.04 (m, 1H), 7.23 (t, 1H), 7.35 (m, 1H), 7.44 (m, 4H);

Isomer 2 (100 mg) gave the following spectral data: (400 MHz, CDCl$_3$): δ=1.62 (m, 1H), 1.76 (s, 3H), 2.31 (s, 3H), 2.48 (m, 2H), 3.28 (m, 1H), 3.50 (m, 1H), 6.95 (m, 1H), 7.04 (m, 1H), 7.23 (t, 1H), 7.35 (m, 1H), 7.44 (m, 4H).

Example 8

6-allyl-3-((S)-1-cyclohexylethyl)-6-(4-fluorophenyl)-1,3-oxazinan-2-one

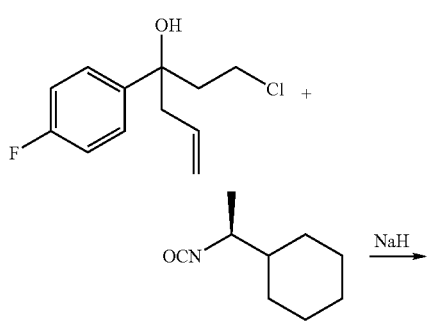

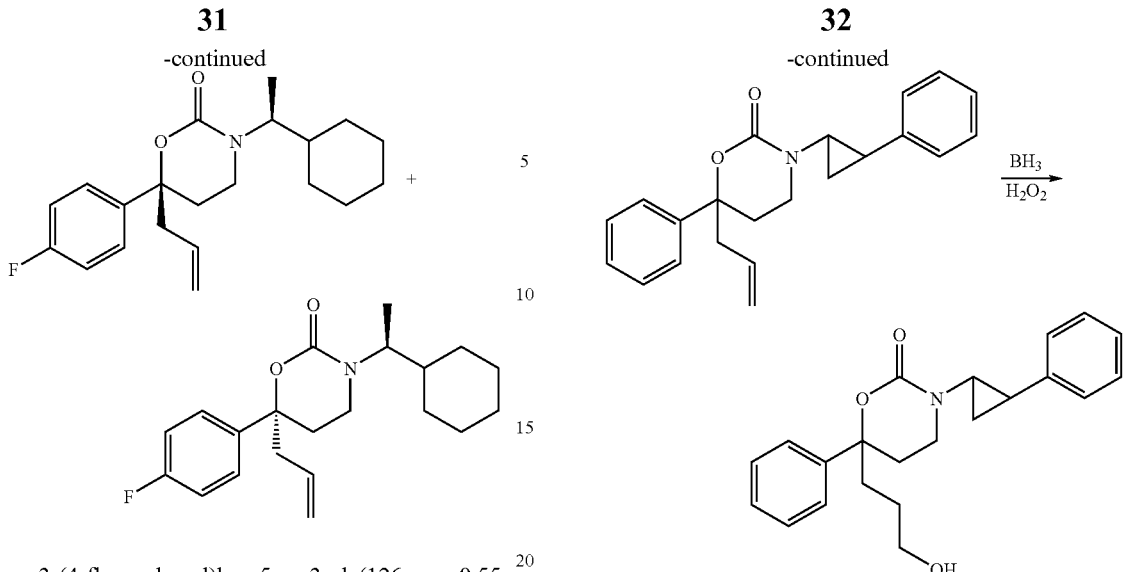

1-chloro-3-(4-fluorophenyl)hex-5-en-3-ol (126 mg, 0.55 mmol), (S)-(+)-1-cyclohexylethyl isocyanate (160 mg, 1.44 equiv.) and proton sponge (271 mg, 2.3 equiv.) were dissolved in dry THF (5 mL) and heated to reflux for 3 h. The mixture was then cooled to 0° C. and NaH (22 mg, 1.0 equiv.) was added slowly. After 5 min, the mixture was heated to reflux overnight. LC-MS showed the reaction was complete. The mixture was diluted with EtOAc (50 mL) and washed with 1% aq HCl (2×15 mL), satd aq NaHCO$_3$ (10 mL) and brine (10 mL), and dried over Na$_2$SO$_4$. After filtration and concentration, the residue was purified by chromatography on a 12-g silica cartridge eluted with a 10-45% EtOAc in hexanes gradient to afford two isomeric products.

Isomer 1: (R)-6-allyl-3-((S)-1-cyclohexylethyl)-6-(4-fluorophenyl)-1,3-oxazinan-2-one (57.5 mg, 30%). LC-MS Method 1, $t_R$=2.05 min, m/z=346. $^1$H NMR (CDCl$_3$) 7.29 (m, 2H), 7.02 (m, 2H), 5.70 (m, 1H), 5.05 (dd, 2H), 3.94 (m, 1H), 3.06 (m, 1H), 2.68-2.49 (m, 3H), 2.33 (m, 1H), 2.14 (m, 1H), 1.17 (d, 3H), 0.78 (m, 2H)

Isomer 2: (S)-6-allyl-3-((S)-1-cyclohexylethyl)-6-(4-fluorophenyl)-1,3-oxazinan-2-one (56 mg, 29%). LC-MS Method 1, $t_R$=2.06 min, m/z=346. $^1$H NMR (CDCl$_3$) 7.27 (m, 2H), 7.03 (t, 2H), 5.71 (m, 1H), 5.05 (dd, 2H), 3.95 (m, 1H), 2.92 (m, 1H), 2.72 (m, 1H), 2.57 (m, 2H), 2.22 (m, 2H), 1.49 (d, 1H), 1.32 (m, 1H), 0.86 (d, 3H).

Example 9

6-(3-hydroxypropyl)-6-phenyl-3-(2-phenylcyclopropyl)-1,3-oxazinan-2-one

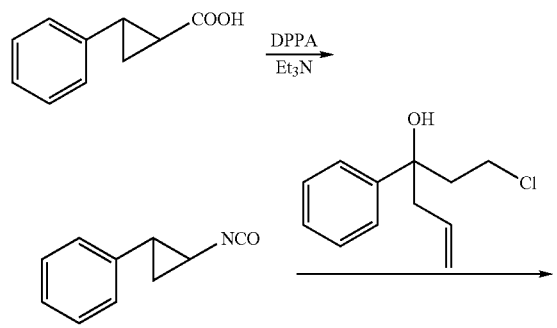

Step 1
To a solution of 2-phenylcyclopropanecarboxylic acid (1.0 g, 6.17 mmol) in dry toluene (20 mL) was added triethylamine (934 mg, 9.26 mmol) and DPPA (2.0 g, 7.41 mmol) under N$_2$, and the reaction mixture was refluxed for 3 h. The solution was concentrated to give (2-isocyanatocyclopropyl)benzene (800 mg), which was used for the next step without further purification.

Step 2
To a solution of (2-isocyanatocyclopropyl)benzene (800 mg, 5.03 mmol) in THF (15 mL) was added DBU (1.61 g, 10.48 mmol) and 1-chloro-3-phenylhex-5-en-3-ol (880 mg, 4.19 mmol), and the mixture was refluxed overnight. The solution was diluted with EtOAc, and washed with 1 N HCl (2×15 mL). The aqueous phase was extracted with EtOAc. The combined organic layers were washed with brine, dried over Na$_2$SO$_4$, filtered and concentrated to give crude product, which was purified by preparative TLC to afford 6-allyl-6-phenyl-3-(2-phenylcyclopropyl)-1,3-oxazinan-2-one (100 mg, 6%). $^1$H NMR (CDCl$_3$): 1.05-1.21 (m, 3H), 1.36-1.42 (m, 1H), 2.13-2.34 (m, 1H), 2.39-2.61 (m, 2H), 2.92-3.15 (m, 1H), 3.76-4.01 (m, 1H), 4.95-5.10 (m, 2H), 5.42-5.73 (m, 1H), 6.95-6.99 (m, 1H), 7.10-7.24 (m, 10H).

Step 3
To a solution of 6-allyl-6-phenyl-3-(2-phenylcyclopropyl)-1,3-oxazinan-2-one (200 mg, 0.60 mmol) in dry THF (5 mL) was added dropwise 1 M of BH$_3$/THF (1.8 mL, 1.8 mmol) at 0° C. under N$_2$. After stirring at rt for 2 h, the reaction mixture was cooled to 0° C. again, and water (0.1 mL), 3 M of aqueous NaOH solution (0.1 mL), and 30% H$_2$O$_2$ (0.3 mL) were added sequentially. After the mixture was stirred at rt for another 2 h, 1 N aqueous HCl (0.5 mL) was added. The mixture was extracted with EtOAc. The organic layer was washed with brine, dried over Na$_2$SO$_4$, filtered and concentrated to give the crude product, which was purified by preparative TLC followed by preparative HPLC to afford two isomers.

Isomer 1 (20 mg, 9%): LC-MS Method 3 $t_R$=1.151, min, m/z=352.2; $^1$H NMR (CDCl$_3$) 0.83 (m, 2H), 1.12 (m, 1H), 1.23 (m, 4H), 1.68 (m, 1H), 1.97 (m, 2H), 2.16 (m, 1H), 2.21 (m, 1H), 2.84 (m, 1H), 3.13 (m, 1H), 3.52 (m, 2H), 4.14 (m, 1H), 7.03 (m, 2H), 7.11 (m, 1H), 7.17 (m, 2H), 7.29 (m, 4H), 7.46-7.63 (m, 1H).

Isomer 2 (15 mg, 7%): LC-MS Method 3 $t_R$=1.149, min, ink=352.2; $^1$H NMR (CDCl$_3$) 0.85 (m, 2H), 1.11 (m, 1H), 1.26 (m, 3H), 1.67 (m, 2H), 1.96 (m, 2H), 2.18 (m, 1H), 2.27 (m, 1H), 2.83 (m, 1H), 3.13 (m, 1H), 3.52 (m, 2H), 4.15 (m, 1H), 7.02 (m, 2H), 7.11 (m, 1H), 7.15 (m, 2H), 7.26 (m, 3H), 7.29 (m, 2H), 7.46-7.63 (m, 1H).

Example 10

(R)-3-((S)-1-(4-bromophenyl)propyl)-6-(3-hydroxypropyl)-6-phenyl-1,3-oxazinan-7-one

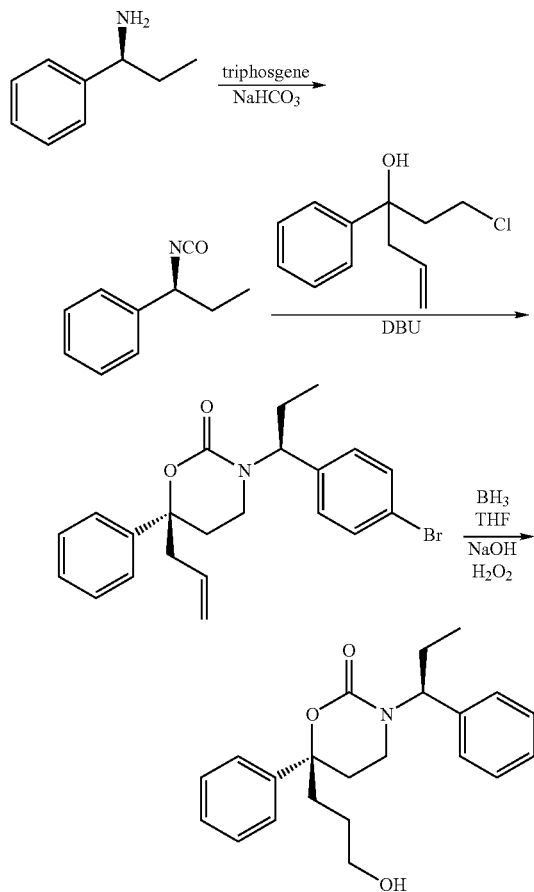

Step 1

To a solution of (S)-1-phenylpropan-1-amine (3.00 g, 14 mmol) in the mixture of methylene chloride (50 mL) and saturated NaHCO$_3$ (50 mL) was added triphosgene (1.40 g, 4.60 mmol) at 0° C. The mixture was stirred for 15 minutes. The organic phase was separated, dried and concentrated to give (S)-(1-isocyanatopropyl)benzene (3.0 g, 88%). $^1$H NMR (CDCl$_3$): δ=0.93 (q, 3H), 1.81 (m, 2H), 4.50 (m, 1H), 7.13 (m, 2H), 7.22 (m, 1H), 7.50 (m, 2H).

Step 2

A mixture of (S)-(1-isocyanatopropyl)benzene (3.0 g, 12.5 mmol), 1-chloro-3-phenylhex-5-en-3-ol (3.6 g, 12.5 mmol) and DBU (3.80 g, 25 mmol) in tetrahydrofuran (20 mL) was heated to reflux overnight. The mixture was washed by 1 N HCl and extracted with EtOAc. The organic phase was concentrated to give the crude product which was purified by column chromatography to give (R)-6-allyl-3-((S)-1-(4-bromophenyl)propyl)-6-phenyl-1,3-oxazinan-2-one (1.0 g, 20%). $^1$H NMR (400 MHz, CDCl$_3$): δ=0.92 (t, 3H), 1.72-2.00 (m, 4H), 2.06-2.31 (m, 4H), 2.53 (m, 2H), 2.82 (m, 1H), 4.99 (m, 2H), 5.32 (m, 1H), 5.69 (m, 1H), 6.72 (m, 1H), 7.12 (m, 4H), 7.25 (m, 4H).

Step 3

To a solution of (R)-6-allyl-3-((S)-1-(4-bromophenyl)propyl)-6-phenyl-1,3-oxazinan-2-one (100 mg, 0.242 mmol) in tetrahydrofuran (10 mL) was added BH$_3$ THF (3 mL, 1 mol/L) at 0° C. under nitrogen. The formed mixture was stirred for 2 h. Then the reaction was quenched by water, followed by 3 mol/L NaOH and H$_2$O$_2$ (3 mL). The PH of the mixture was adjusted to <7 with 5% HCl. The organic phase was separated, extracted by EtOAc, and concentrated to give the crude product, which was purified by preparative HPLC to give (R)-3-((S)-1-(4-bromophenyl)propyl)-6-(3-hydroxypropyl)-6-phenyl-1,3-oxazinan-2-one (15 mg, 15%). LC-MS Method 3 $t_R$=1.36, min, m/z=432, 434; $^1$H NMR (CDCl$_3$): δ=0.99 (t, 3H), 1.29 (m, 1H), 1.63 (m, 1H), 1.98 (m, 4H), 2.20-2.42 (m, 2H), 2.48 (m, 1H), 3.08 (m, 1H), 3.49 (m, 1H), 5.30 (m, 1H), 6.92 (m, 2H), 7.26 (m, 4H), 7.35 (m, 2H).

Example 11

(R)-3-((R)-1-(2',4'-difluorobiphenyl-4-yl)ethyl)-6-(4-fluorophenyl)-6-(2-hydroxyethyl)-1,3-oxazinan-2-one

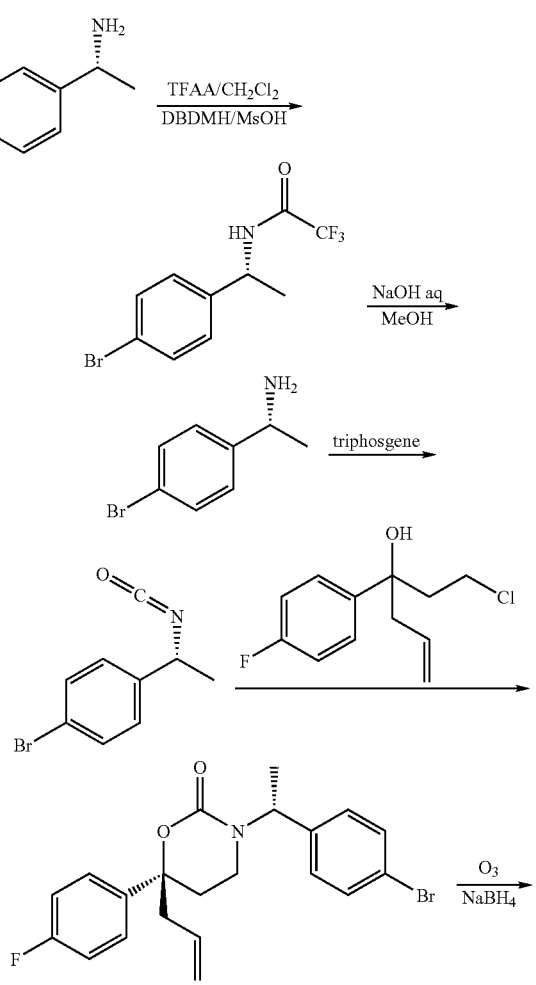

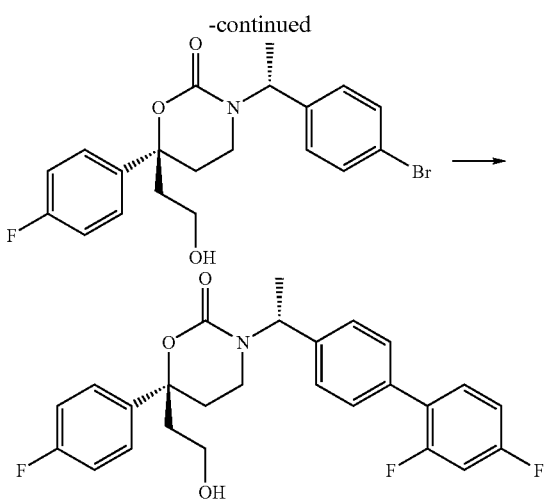

Step 1

TFAA (134 mL, 948 mmol) was dissolved in CH$_2$Cl$_2$ (600 mL) and cooled in an ice water bath. A solution of (S)-1-phenylpropan-1-amine (112.8 g, 930 mmol) in CH$_2$Cl$_2$ (200 mL) was added dropwise and then the ice bath was removed. The reaction mixture was stirred for 3 hrs at ambient temperature. Then the above mixture was cooled in an ice bath and MsOH (160 mL, 2.5 mol) was added dropwise followed by DBDMH (130 g, 454 mmol). The reaction mixture was left stirring overnight at rt and then quenched with water and brine. The combined organic phases were dried over NaSO$_4$, filtered and concentrated to give (R)-N-(1-(4-bromophenyl)ethyl)-2,2,2-trifluoroacetamide (120 g, 44%) as a off-white solid. $^1$H NMR (CDCl$_3$): 1.56 (m, 3H), 1.86 (m, 2H), 5.11 (m, 1H), 6.63 (m, 1H), 7.18 (m, 2H), 7.50 (m, 2H).

Step 2

(R)-N-(1-(4-bromophenyl)ethyl)-2,2,2-trifluoroacetamide (20 g, 68 mmol) was dissolved in methanol (200 mL) and cooled in an ice-water bath. Then aqueous NaOH (2 M, 100 mL) was added to the above mixture. The reaction mixture was stirred overnight at ambient temperature. The reaction mixture was concentrated and then partitioned between CH$_2$Cl$_2$ and water. The aqueous layer was extracted with addition CH$_2$Cl$_2$ and the combined organic phases were dried over Na$_2$SO$_4$, filtered and concentrated to give (R)-1-(4-bromophenyl)ethan amine (9.8 g, 73%). $^1$H NMR (DMSO): 1.19 (m, 3H), 3.92 (m, 1H), 7.28 (m, 2H), 7.42 (m, 2H).

Step 3

To a solution of (S)-1-(4-bromophenyl)propan-1-amine (5 g, 25 mmol) in CH$_2$Cl$_2$ (10 mL) was added saturated aqueous NaHCO$_3$ (10 mL) and then triphosgene (2.45 g, 8 mmol) at 0□. Then the reaction mixture was stirred for 15 minutes at 0° C. under nitrogen. The reaction mixture was extracted with CH$_2$Cl$_2$ twice. The combined organic phases were dried over Na$_2$SO$_4$, filtered and concentrated to afford (R)-1-bromo-4-(1-isocyanatoethyl)benzene (2.5 g, 44%), which was used for the next step without purification.

Step 4

To a solution of (R)-1-bromo-4-(1-isocyanatoethyl)benzene (2.5 g, 11 mmol) in THF anhydrous (40 mL) was added 1-chloro-3-(4-fluorophenyl)hex-5-en-3-ol (1.69 g, 7 mmol) and DBU (5.68 g, 33 mmol) at ambient temperature and the reaction mixture was refluxed overnight. The reaction mixture was extracted with 1 N aq HCl and EtOAc. The combined organic phases were dried over Na$_2$SO$_4$, filtered and concentrated to afford the residue, which was purified by column chromatography to give two isomers.

Isomer 1: (R)-6-allyl-3-((R)-1-(4-bromophenyl)ethyl)-6-(4-fluorophenyl)-1,3-oxazinan-2-one (334 mg, 7%). $^1$H NMR (CD$_3$OD): 1.50 (m, 3H), 2.16-2.38 (m, 2H), 2.46 (m, 1H), 2.60 (m, 2H), 3.10 (m, 1H), 5.05 (m, 2H), 5.48 (m, 1H), 5.66 (m, 1H), 6.82 (m, 2H), 7.08 (m, 2H), 7.26 (m, 4H).

Isomer 2: (S)-6-allyl-3-((R)-1-(4-bromophenyl)ethyl)-6-(4-fluorophenyl)-1,3-oxazinan-2-one.

Step 5

A solution of (R)-6-allyl-3-((R)-1-(4-bromophenyl)ethyl)-6-(4-fluorophenyl)-1,3-oxazinan-2-one (334 mg, 0.80 mmol) in dry CH$_2$Cl$_2$ (20 mL) was treated with ozone at −78° C. until the reaction mixture became blue. Then the mixture was flushed with oxygen to remove excess ozone. To the above mixture was added NaBH$_4$ (273 mg, 7 mmol) at 0° C. and the reaction mixture was stirred for 4 hrs at ambient temperature under nitrogen. The reaction mixture was washed with water and then extract with CH$_2$Cl$_2$ twice. The combined organic phases were dried over NaSO$_4$, filtered and concentrated to give the residue, which was purified by preparative HPLC to afford (S)-3-((R)-1-(4-bromophenyl)ethyl)-6-(4-fluorophenyl)-6-(2-hydroxyethyl)-1,3-oxazinan-2-one (118 mg, 35%). $^1$H NMR (CD$_3$OD): 1.50 (m, 3H), 2.12 (m, 2H), 2.29 (m, 2H), 2.50 (m, 1H), 3.10 (m, 1H), 3.33 (m, 1H), 3.68 (m, 1H), 4.56 (m, 1H), 5.50 (m, 1H), 6.86 (m, 2H), 7.10 (m, 2H), 7.30 (m, 4H).

Step 6

To a solution of (S)-3-((R)-1-(4-bromophenyl)ethyl)-6-(4-fluorophenyl)-6-(2-hydroxyethyl)-1,3-oxazinan-2-one (109 mg, 0.26 mmol), 2,4-difluorophenylboronic acid (49 mg, 0.31 mmol) and Pd(PPh$_3$)$_4$ (30 mg, 0.03 mmol) in dioxane (8 mL) was added a solution of CsCO$_3$ (2 M, 1 mL) at 0□. Then the reaction mixture was refluxed overnight under nitrogen. The reaction mixture was washed with water and then extract with CH$_2$Cl$_2$ twice. The combined organic phases were dried over Na$_2$SO$_4$, filtered and concentrated to give the residue, which was purified by preparative HPLC to afford (S)-3-((R)-1-(2',4'-difluorobiphenyl-4-yl)ethyl)-6-(4-fluorophenyl)-6-(2-hydroxyethyl)-1,3-oxazinan-2-one (49 mg, 42%). LC-MS Method 3 $t_R$=1.41, min, m/z=456; $^1$H NMR (CD$_3$OD): 1.55 (m, 3H), 2.12 (m, 2H), 2.22-2.46 (m, 3H), 2.52 (m, 1H), 3.12 (m, 1H), 3.33 (m, 1H), 3.68 (m, 1H), 5.56 (m, 1H), 7.08 (m, 6H), 7.08 (m, 2H), 7.35 (m, 5H). 443-155-3.

(R)-3-((R)-1-(2',4'-difluorobiphenyl-4-yl)ethyl)-6-(4-fluorophenyl)-6-(2-hydroxyethyl)-1,3-oxazinan-2-one was prepared from (S)-6-allyl-3-((R)-1-(4-bromophenyl)ethyl)-6-(4-fluorophenyl)-1,3-oxazinan-2-one following procedures analogous to those described in Steps 5 and 6 immediately above. LC-MS Method 3 $t_R$=1.47, min, m/z=456; $^1$H NMR (CD$_3$OD) 1.35 (m, 3H), 2.18 (m, 2H), 2.40 (m, 1H), 2.51 (m, 1H), 2.82 (m, 2H), 3.33 (m, 1H), 3.71 (m, 1H), 4.22-4.48 (m, 1H), 5.62 (m, 1H), 7.03 (m, 2H), 7.18 (m, 2H), 7.38 (m, 4H), 7.50 (m, 3H).

Example 12

(R)-3-((S)-1-(4-bromophenyl)ethyl)-6-(3-hydroxypropyl)-6-phenyl-1,3-oxazinan-2-one

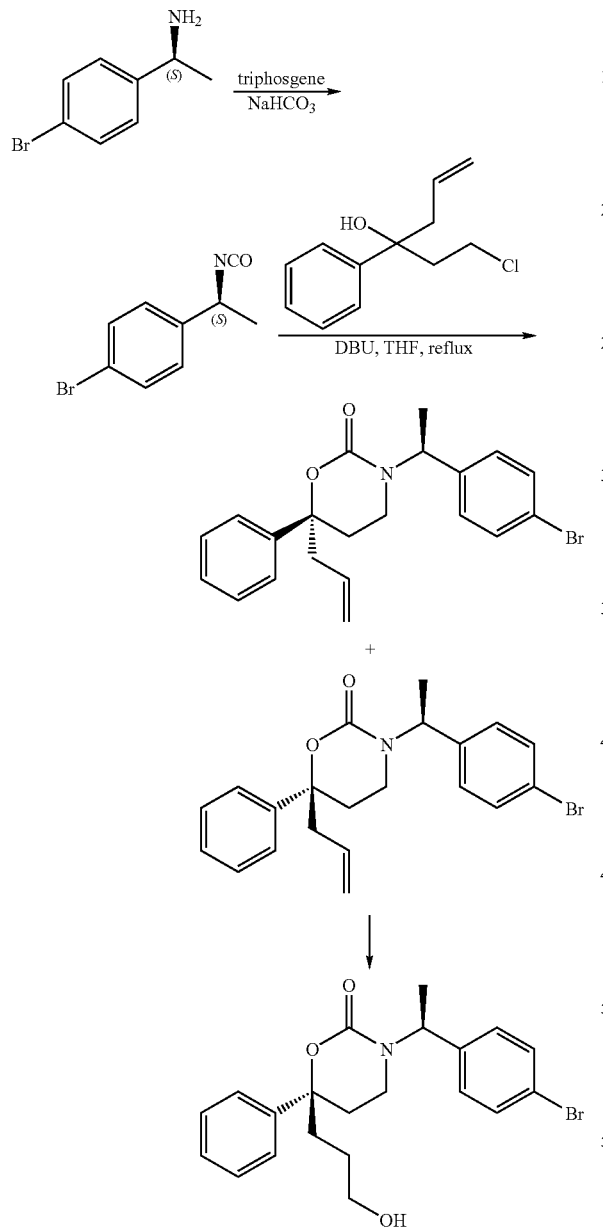

Step 1

To a solution of (S)-1-(4-bromophenyl)ethanamine (40 g, 0.2 mol) in methylene chloride (600 mL) and satd aq NaHCO$_3$ (600 mL) was added triphosgene (27 g, 0.025 mol) at 0° C. The mixture was stirred for 15 min. The organic phase was separated, dried and concentrated to give 1-bromo-4-(1-isocyanato-ethyl)-benzene (35 g, crude).

Step 2

A mixture of 1-chloro-3-phenyl-hex-5-en-3-ol (27.5 g, 130 mmol), (S)-(−)-1-(-bromophenyl)ethyl isocyanate (35 g, 160 mmol), and DBU (80 g, 325 mmol) in THF (400 mL) was heated to reflux for 25 h. The mixture was diluted with EtOAc and washed with 1 N aq HCl. The aqueous phase was extracted with EtOAc (3×). The combined organic phase was dried over Na$_2$SO$_4$. After the solvents were evaporated, the crude product was purified by column chromatography to give (R)-6-allyl-3-((S)-1-(4-bromophenyl)ethyl)-6-phenyl-1,3-oxazinan-2-one (30 g, yield 45%).

Step 3

The title compound was prepared from (R)-6-allyl-3-((S)-1-(4-bromophenyl)ethyl)-6-phenyl-1,3-oxazinan-2-one following a procedure analogous to that described in Example 78. LC-MS Method 2 $t_R$=1.36 min, m/z=440.1; $^1$H NMR (CDCl$_3$) 1.26-1.39 (m, 1H), 1.42 (d, 3H), 1.58-1.71 (m, 1H), 1.85-1.95 (m, 2H), 2.11-2.45 (m, 3H), 2.79 (m, 1H), 3.52 (m, 2H), 5.54 (m, 1H), 6.67 (d, 2H), 7.12-7.31 (m, 7H).

Synthesis of Biaryls Via Suzuki Synthesis

Example 13

3-(biphenyl-3-yl)-6-methyl-6-phenyl-1,3-oxazinan-2-one

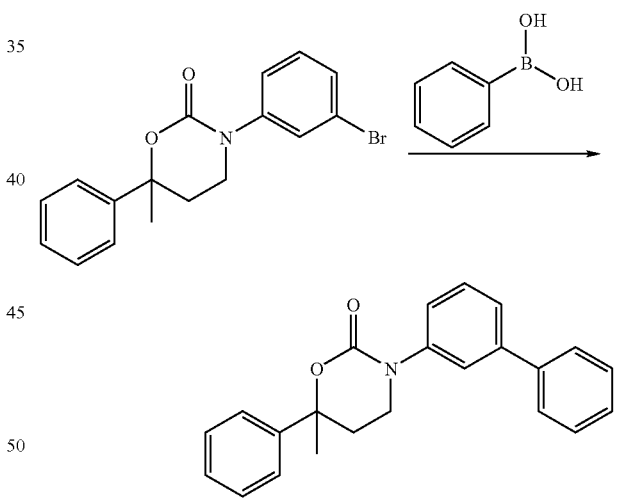

To a solution of 3-(3-bromophenyl)-6-methyl-6-phenyl-1,3-oxazinan-2-one (50 mg, 0.14 mmol) and phenylboronic acid (35 mg, 0.29 mmol) in THF (2 mL) was added a solution of NaHCO$_3$ (31 mg, 0.29 mmol) in H$_2$O (2 mL) followed by Pd(PPh$_3$)Cl$_2$ (9 mg, 0.01 mmol). The mixture was refluxed overnight. The mixture was concentrated to give the crude product, which was purified by column chromatography, followed by preparative HPLC to afford 3-(biphenyl-3-yl)-6-methyl-6-phenyl-1,3-oxazinan-2-one (10 mg, 20%). $^1$H NMR: (400 MHz, CDCl$_3$): δ 1.71 (s, 3H), 2.40 (m, 1H), 2.48 (m, 1H), 3.31 (m, 1H), 3.54 (m, 1H), 7.08 (m, 1H), 7.30 (m, 3H), 7.7.32-7.42 (m, 8H), 7.46 (m, 2H). LC-MS Method 3, $t_R$=1.362 min, m/z=344. $^1$H NMR (CDCl$_3$) 1.75 (s, 3H), 2.32-2.43 (m, 1H), 2.50 (m, 1H), 3.20 (m, 1H), 3.52 (m, 1H), 7.10 (d, 1H), 7.25-7.45 (m, 11H), 7.50 (d, 2H).

Example 14

6-allyl-3-(2',4'-difluorobiphenyl-3-yl)-6-phenyl-1,3-oxazinan-2-one

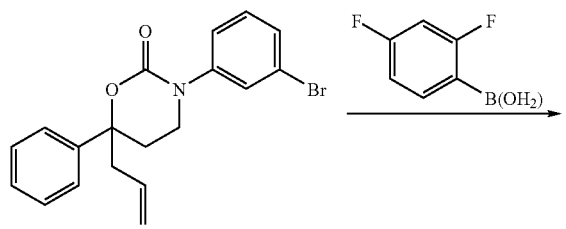

Step 1. 6-allyl-3-(2',4'-difluorobiphenyl-3-yl)-6-phenyl-1,3-oxazinan-2-one

To a solution of 6-allyl-3-(3-bromophenyl)-6-phenyl-1,3-oxazinan-2-one (50 mg, 0.134 mmol) and 2,4-difluorophenylboronic acid (40 mg, 0.215 mmol), $K_2CO_3$ (0.5 mL, 2 M) in 1,4-dioxane (1.5 ml) was slowly added $Pd(Ph_3)_2Cl_2$ (10 mg, 20%) at 0° C. under $N_2$. The mixture was refluxed overnight. The mixture was concentrated to give the crude product, which was purified by TLC and preparative HPLC to afford 6-allyl-3-(2',4'-difluorobiphenyl-3-yl)-6-phenyl-1,3-oxazinan-2-one (10 mg, 18%). $^1$H NMR (400 MHz, $CDCl_3$): δ=2.40 (m, 2H), 2.55-2.72 (m, 2H), 3.26 (m, 1H), 3.47 (m, 1H), 5.05 (m, 2H), 5.76 (m, 1H), 6.76-6.90 (m, 2H), 7.04 (m, 1H), 7.28 (m, 4H), 7.36 (m, 2H).

Example 15

6-(2-aminoethyl)-3-(2',4'-difluorobiphenyl-3-yl)-6-phenyl-1,3-oxazinan-2-one

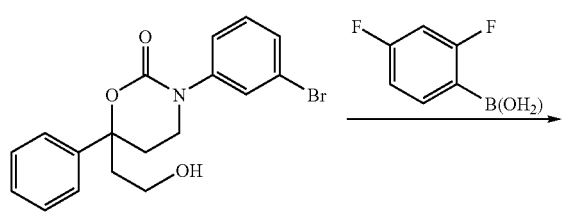

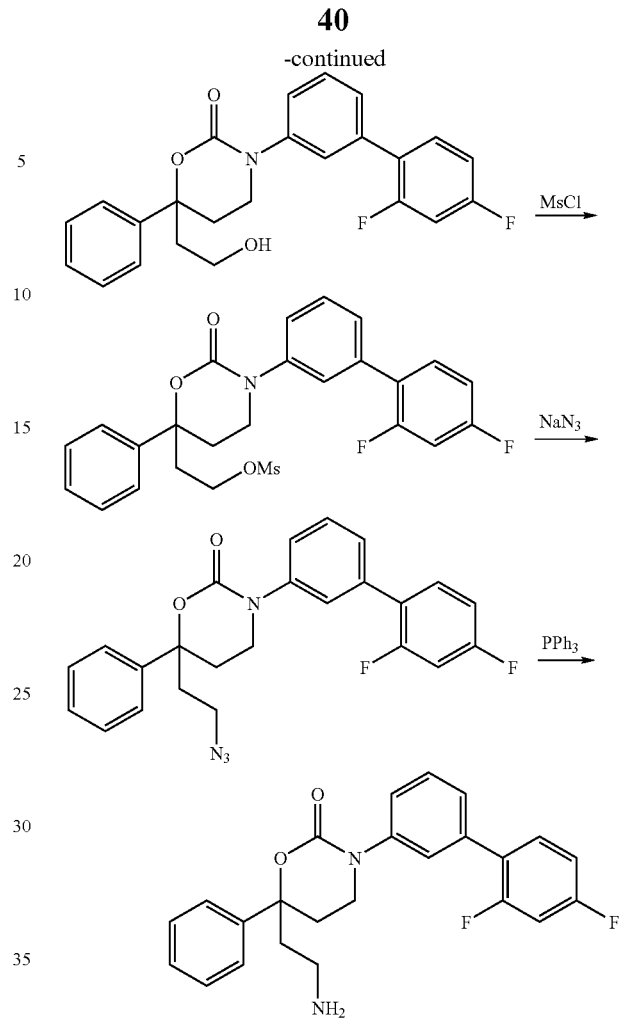

Step 1. 3-(2',4'-difluorobiphenyl-3-yl)-6-(2-hydroxyethyl)-6-phenyl-1,3-oxazinan-2-one To a solution of 3-(3-bromophenyl)-6-(2-hydroxyethyl)-6-phenyl-1,3-oxazinan-2-one (200 mg, 0.538 mmol), 4-fluorophenylboronic acid (128 mg, 0.806 mmol), and aq. $K_2CO_3$ (1 mL, 2 M) in 1,4-dioxane (3 ml) was slowly added $Pd(Ph_3)_2Cl_2$ (20 mg, 10%) at 0° C. under $N_2$. The mixture was refluxed overnight. The mixture was concentrated to give the crude product, which was purified by TLC and preparative HPLC to afford 3-(2',4'-difluorobiphenyl-3-yl)-6-(2-hydroxyethyl)-6-phenyl-1,3-oxazinan-2-one (200 mg, 91%). $^1$H-NMR (400 MHz, $CDCl_3$): δ=2.12-2.35 (m, 2H), 2.51 (m, 2H), 3.26 (m, 1H), 3.47-3.6 (m, 2H), 4.25 (m, 1H), 6.83 (m, 2H), 7.06 (m, 1H), 7.26-7.51 (m, 8H).

Step 2. 2-(3-(2',4'-difluorobiphenyl-3-yl)-2-oxo-6-phenyl-1,3-oxazinan-6-yl)ethyl methanesulfonate To a solution of 3-(2',4'-difluorobiphenyl-3-yl)-6-(2-hydroxyethyl)-6-phenyl-1,3-oxazinan-2-one (200 mg, 0.49 mmol) in dry $CH_2Cl_2$ (4 mL) was added $Et_3N$ (0.234 mL, 1.46 mmol) at 0~-5° C. A solution of methanesulfonyl chloride (67 mg, 0.59 mmol) in dry $CH_2Cl_2$ (1 mL) was added dropwise at the same temperature. After addition, the mixture was allowed to warm to rt gradually. When the reaction was complete, water (10 mL) was added and the mixture was extracted with $CH_2Cl_2$ (3×10 mL). The combined organic layers were washed with 10% aq citric acid, satd aq $NaHCO_3$ and brine, then dried over $Na_2SO_4$, filtered and concentrated to give 2-(3-(2',4'-difluorobiphenyl-3-yl)-2-oxo-6-phenyl-1,3-oxazinan-6-yl)ethyl methanesulfonate (230 mg, 97%), which was used in the next step without purification.

Step 3. 6-(2-azidoethyl)-3-(2',4'-difluorobiphenyl-3-yl)-6-phenyl-1,3-oxazinan-2-one To a solution of 2-(3-(2',4'-difluorobiphenyl-3-yl)-2-oxo-6-phenyl-1,3-oxazinan-6-yl)ethyl methanesulfonate (230 mg, 0.47 mmol) in anhydrous DMF (5 mL) was added NaN$_3$ (92 mg, 1.42 mmol). The reaction mixture was heated to 70° C. overnight. The reaction mixture was cooled to rt and diluted with EtOAc (30 mL), and water (20 ml). The organic phase was washed with water (3×20 mL), dried over Na$_2$SO$_4$ and evaporated to give 6-(2-azidoethyl)-3-(2',4'-difluorobiphenyl-3-yl)-6-phenyl-1,3-oxazinan-2-one (100 mg, 49%).

Step 4. 3-(2',4'-difluorobiphenyl-3-yl)-6-(2-hydroxyethyl)-6-phenyl-1,3-oxazinan-2-one To a solution of 6-(2-azidoethyl)-3-(2',4'-difluorobiphenyl-3-yl)-6-phenyl-1,3-oxazinan-2-one (100 mg, 0.23 mmol) in 20:1 THF/H$_2$O (3 mL) was added PPh$_3$ (72 mg, 0.28 mmol). The reaction mixture was stirred at rt overnight. The solvent was removed under reduced pressure, and the residue was purified by column chromatography on silica gel to afford 6-(2-aminoethyl)-3-(2',4'-difluorobiphenyl-3-yl)-6-phenyl-1,3-oxazinan-2-one (30 mg, 31%). $^1$H NMR (400 MHz, CDCl$_3$): δ=2.20-2.51 (m, 2H), 2.51-2.60 (m, 2H), 2.72 (m, 1H), 3.00 (m, 1H), 3.24 (m, 1H), 3.53 (m, 1H), 6.85-6.99 (m, 2H), 7.14 (m, 1H), 7.31-7.50 (m, 8H).

Example 16

6-allyl-3-((S)-1-(2',4'-difluorobiphenyl-4-yl)ethyl)-6-(4-fluorophenyl)-1,3-oxazinan-2-one

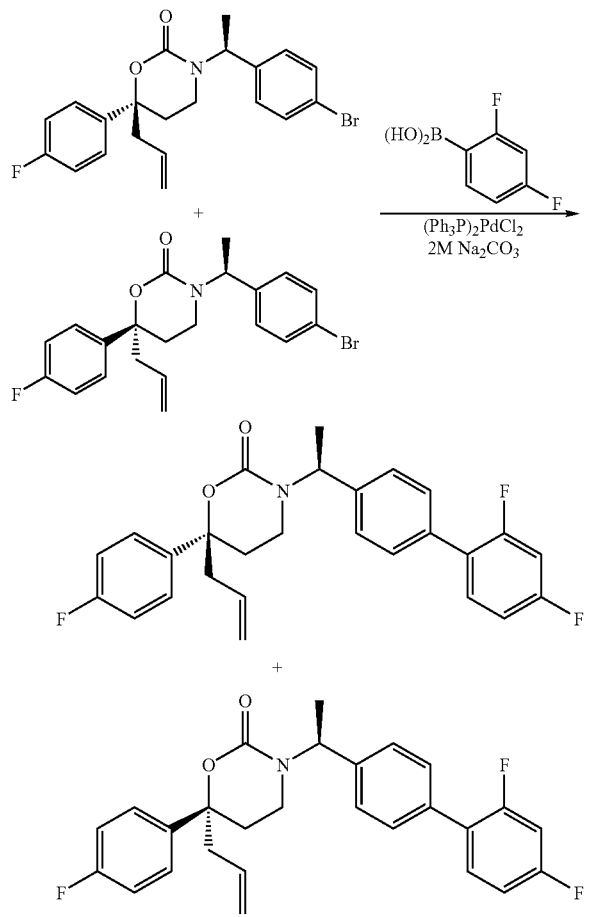

Step 1. 6-allyl-3-((S)-1-(2',4'-difluorobiphenyl-4-yl)ethyl)-6-(4-fluorophenyl)-1,3-oxazinan-2-one To a solution of 6-allyl-3-((S)-1-(4-bromophenyl)ethyl)-6-(4-fluorophenyl)-1,3-oxazinan-2-one (0.3860 g, 0.92 mmol, 1.0 equiv) in THF (10 mL) were added, under a nitrogen atmosphere, 2,4-difluorophenylboronic acid (0.2708 g, 1.71 mmol, 1.86 equiv), 2 M aq Na$_2$CO$_3$ (8 mL), and (Ph$_3$P)$_2$PdCl$_2$ (0.0308 g, 0.0438 mmol, 0.047 equiv). The mixture was stirred for 2 d at 100° C. Brine was then added, the mixture was extracted with Et$_2$O (3×), and the combined ether extracts were dried over Na$_2$SO$_4$. After the solvents were evaporated, the crude product was directly used in the next step without further purification. LC-MS t$_R$=2.13, 2.17 min in 3 min chromatography, m/z 452 (MH$^+$).

Analytical samples were separated by silica gel chromatography.

Isomer 1: (S)-6-allyl-3-((S)-1-(2',4'-difluorobiphenyl-4-yl)ethyl)-6-(4-fluorophenyl)-1,3-oxazinan-2-one. LC-MS Method 1, t$_R$=2.17 min, m/z=452. $^1$H NMR (CDCl$_3$) 7.47 (d, J=8.2 Hz, 2H), 7.42-7.30 (m, 5H), 7.08 (t, J=8.2 Hz, 2H), 6.98-6.88 (m, 2H), 5.82-5.68 (m, 2H), 5.08 (d, J=10.2 Hz, 1H), 5.02 (d, J=17.0 Hz, 1H), 2.78-2.71 (m, 2H), 2.66-2.54 (m, 2H), 2.25-2.20 (m, 1H), 2.13-2.05 (m, 1H), 1.30 (d, J=7.0 Hz, 3H).

Isomer 2: (R)-6-allyl-3-((S)-1-(2',4'-difluorobiphenyl-4-yl)ethyl)-6-(4-fluorophenyl)-1,3-oxazinan-2-one. LC-MS Method 1, t$_R$=2.13 min, m/z=452. $^1$H NMR (CDCl$_3$) 7.33-7.23 (m, 5H), 7.03 (t, J=8.2 Hz, 2H), 6.96-6.86 (m, 4H), 5.77-5.67 (m, 2H), 5.10 (d, J=10.3 Hz, 1H), 5.04 (d, J=17.3 Hz, 1H), 2.99-2.94 (m, 1H), 2.66-2.54 (m, 2H), 2.41-2.34 (m, 1H), 2.30-2.17 (m, 2H), 1.55 (d, J=7.0 Hz, 3H).

Example 17

3-((S)-1-(2',4'-difluorobiphenyl-4-yl)propyl)-6-(4-fluorophenyl)-6-(2-hydroxyethyl)-1,3-oxazinan-2-one

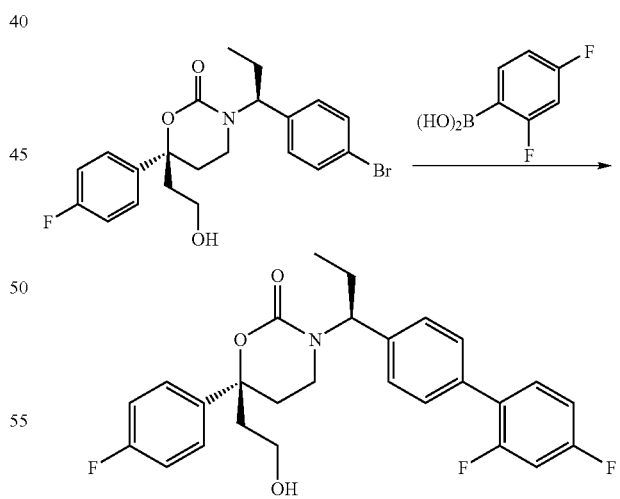

To a solution of (S)-3-((S)-1-(4-bromophenyl)propyl)-6-(4-fluorophenyl)-6-(2-hydroxy ethyl)-1,3-oxazinan-2-one (60 mg, 0.14 mmol), 2,4-difluorophenylboronic acid (26 mg, 0.17 mmol) and Pd(PPh$_3$)$_4$ (16 mg, 0.01 mmol) in dioxane (5 mL) was added a solution of CsCO$_3$ (2 M, 1 mL) at 0° C. Then the reaction mixture was refluxed overnight under nitrogen. The reaction mixture was washed with water and then extract with CH$_2$Cl$_2$ twice. The combined organic phases were dried over Na₂SO₄, filtered and concentrated to give the residue, which was purified by preparative HPLC to afford (S)-3-((S)-1-(2',4'-difluorobiphenyl-4-yl)propyl)-6-(4-fluorophenyl)-6-(2-hydroxyethyl)-1,3-oxazinan-2-one (17 mg, 26%). ¹H NMR (CD₃OD): 0.96 (m, 3H), 2.01 (m, 2H), 2.12 (m, 2H), 2.30 (m, 2H), 2.48 (m, 1H), 3.10 (m, 1H), 3.33 (m, 1H), 3.65 (m, 1H), 5.38 (m, 1H), 7.02 (m, 4H), 7.08 (m, 2H), 7.28 (m, 4H), 7.42 (m, 1H). 443-114-3.

(R)-3-((S)-1-(2',4'-difluorobiphenyl-4-yl)propyl)-6-(4-fluorophenyl)-6-(2-hydroxyethyl)-1,3-oxazinan-2-one was prepared from (R)-3-((S)-1-(4-bromophenyl)propyl)-6-(4-fluorophenyl)-6-(2-hydroxy ethyl)-1,3-oxazinan-2-one following a procedure analogous to that described immediately above. ¹H NMR (CD₃OD): 0.62 (m, 3H), 1.76 (m, 1H), 1.92 (m, 1H), 2.12 (m, 3H), 2.56 (m, 1H), 2.78 (m, 1H), 2.89 (m, 1H), 3.33 (m, 1H), 3.71 (m, 1H), 5.38 (m, 1H), 7.05 (m, 2H), 7.16 (m, 2H), 7.44 (m, 7H).

Example 18

(S)-3-((S)-1-(4'-fluorobiphenyl-4-yl)ethyl)-6-(2-hydroxyethyl)-6-(thiophen-2-yl)-1,3-oxazinan-2-one

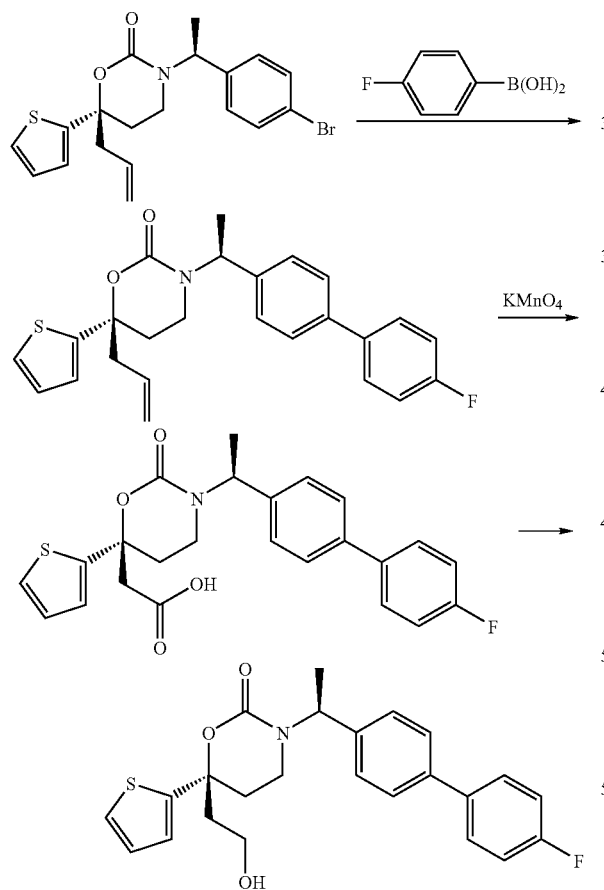

Step 1

Pd(PPh₃)₂Cl₂ (100 mg) was added to the solution of (R)-6-allyl-3-((S)-1-(4-bromophenyl)ethyl)-6-(thiophen-2-yl)-1,3-oxazinan-2-one (1.0 g, 2.5 mmol), 4-fluorophenylboronic acid (420 mg, 3.0 mmol) in 1,4-dioxane. Cs₂CO₃ (5 mL) was slowly added. The mixture was heated to reflux for 2 h. The mixture was quenched with water and separated, extracted with EtOAc twice, dried over anhydrous Na₂SO₄ and concentrated to afford the residue, which was purified by TLC to give (R)-6-allyl-3-((S)-1-(4'-fluorobiphenyl-4-yl)ethyl)-6-(thiophen-2-yl)-1,3-oxazinan-2-one (768 mg, 73%).

Step 2

To a solution of (R)-6-allyl-3-((S)-1-(4'-fluorobiphenyl-4-yl)ethyl)-6-(thiophen-2-yl)-1,3-oxazinan-2-one (300 mg, 0.71 mmol) was added aqueous solution of KMnO₄ (66 mg, 0.42 mmol) and NaIO₄ (537 mg, 2.52 mmol). The reaction mixture was stirred at rt overnight. The reaction mixture was filtered and concentrated, then extracted with CH₂Cl₂. The organic phases was dried over Na₂SO₄, filtered and concentrated to afford 2-((S)-3-((S)-1-(4'-fluorobiphenyl-4-yl)ethyl)-2-oxo-6-(thiophen-2-yl)-1,3-oxazinan-6-yl)acetic acid (218 mg, 70%).

Step 3

A solution of 2-((S'-3-((S)-1-(4'-fluorobiphenyl-4-yl)ethyl)-2-oxo-6-(thiophen-2-yl)-1,3-oxazinan-6-yl)acetic acid (218 mg, 0.5 mmol) in THF anhydrous (10 mL) was added BH₃ (3.0 mL) at 0□ and then stirred at reflux for 2 h. Then the reaction mixture quenched by water and separated, extracted with EtOAc twice. The organic phases was dried over Na₂SO₄, filtered and concentrated to afford the residue, which was purified by TLC to give (S)-3-((S)-1-(4'-fluorobiphenyl-4-yl)ethyl)-6-(2-hydroxyethyl)-6-(thiophen-2-yl)-1,3-oxazinan-2-one (85 mg, 40%). LC-MS Method 3 t_R=1.35, min, m/z=426, 448; ¹H NMR (CD₃OD): 1.50 (m, 3H), 2.15 (m, 2H), 2.30 (m, 1H), 2.40 (m, 1H), 2.60 (m, 1H), 3.15 (m, 1H), 3.45 (m, 1H), 3.70 (m, 1H), 5.60 (m, 1H), 6.90 (m, 1H), 7.00 (m, 1H), 7.10 (m, 4H), 7.35 (m, 3H), 7.55 (m, 2H).

(R)-3-((S)-1-(4'-fluorobiphenyl-4-yl)ethyl)-6-(2-hydroxyethyl)-6-(thiophen-2-yl)-1,3-oxazinan-2-one was prepared following a procedure analogous to that described immediately above. LC-MS Method 3 t_R=1.4, min, m/z=426, 448; ¹H NMR (CD₃OD) 1.38 (d, 3H), 2.01 (m, 1H), 2.18 (m, 3H), 2.41 (m, 1H), 2.86 (m, 1H), 3.02 (m, 1H), 3.41 (m, 1H), 3.72 (m, 1H), 5.62 (m, 1H), 6.98 (m, 1H), 7.03 (m, 1H), 7.15 (m, 1H), 7.36 (m, 3H), 7.58 (m, 4H).

Example 19

(R)-6-(3-hydroxypropyl)-3-((S)-1-(4-(6-oxo-1,6-dihydropyridin-3-yl)phenyl)ethyl)-6-phenyl-1,3-oxazinan-2-one

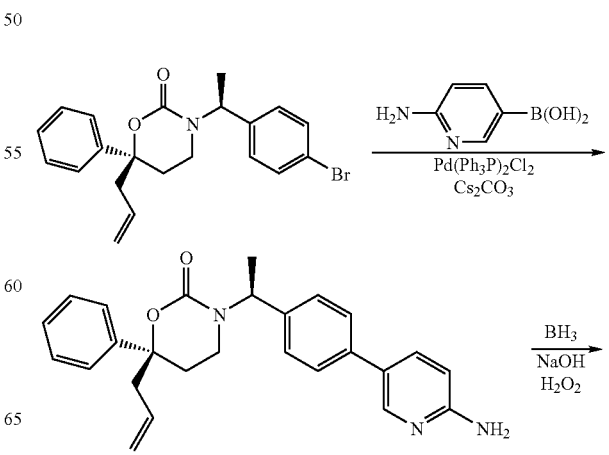

-continued

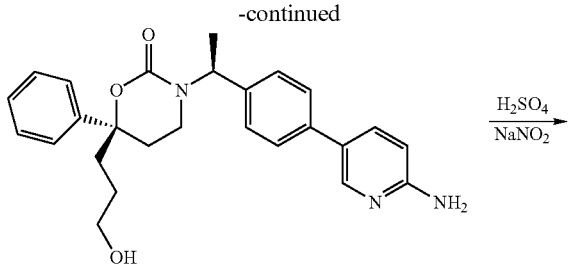

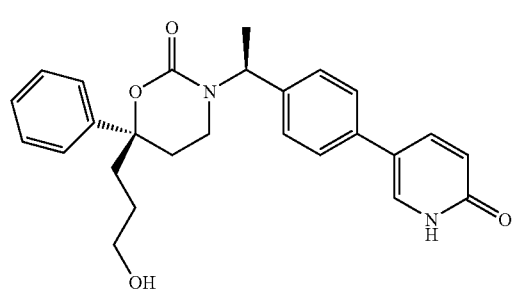

Step 1

A mixture of (R)-6-allyl-3-((S)-1-(4-bromophenyl)ethyl)-6-phenyl-1,3-oxazinan-2-one (150 mg, 0.375 mmol) and 6-aminopyridin-3-ylboronic acid (56 mg, 0.45 mmol), Pd(Ph$_3$P)$_2$Cl$_2$ (15 mg), and aqueous Cs$_2$CO$_3$ solution (0.5 mL, 2 M) in 1,4-dioxane (10 mL) was stirred and heated to reflux for 2 h. The organic phase was separated, and concentrated to give the crude product, which was purified by preparative HPLC to give (R)-6-allyl-3-((S)-1-(4-(6-aminopyridin-3-yl)phenyl)ethyl)-6-phenyl-1,3-oxazinan-2-one (90 mg, 60%).

Step 2

To a solution of (R)-6-allyl-3-((S)-1-(4-(6-aminopyridin-3-yl)phenyl)ethyl)-6-phenyl-1,3-oxazinan-2-one (90 mg, 0.23 mmol) in tetrahydrofuran (10 mL) was added BH$_3$ THF (3.0 mL, 1 mol/L, 4 mmol) at 0° C. under nitrogen atmosphere. The formed mixture was stirred for 2 h. The reaction was quenched by water. Then NaOH (2 mL, 3 mol/L) and H$_2$O$_2$ (1 mL) was added to the above mixture. When the reaction was over, the mixture was extracted with EtOAc. The combined organic phase was concentrated to give the crude product, which was purified by preparative HPLC to give (R)-3-((S)-1-(4-(6-aminopyridin-3-yl)phenyl)ethyl)-6-3-hydroxypropyl)-6-phenyl-1,3-oxazinan-2-one (40 mg, 41%).

Step 3

(R)-3-((S)-1-(4-(6-aminopyridin-3-yl)phenyl)ethyl)-6-(3-hydroxypropyl)-6-phenyl-1,3-oxazinan-2-one (40 mg, 0.09 mmol.) was dissolved in 3.5 M H$_2$SO$_4$ (10 mL), and 2 M NaNO$_2$ (10 mL) was added at 0° C. The reaction mixture was stirred at rt for 2 h and treated with NaOH solution. The mixture was extracted with EtOAc. The combined organic layer was washed with brine, dried over anhydrous Na$_2$SO$_4$, and concentrated to afford the residue, which was purified by preparative HPLC to give (R)-6-(3-hydroxypropyl)-3-((S)-1-(4-(6-oxo-1,6-dihydropyridin-3-yl)phenyl)ethyl)-6-phenyl-1,3-oxazinan-2-one (10 mg, 20%). LC-MS Method 2 t$_R$=1.66, min, m/z=433, 455; $^1$H NMR (CDCl$_3$): 1.36 (m, 2H), 1.50 (m, 3H), 1.68 (m, 2H), 1.92 (m, 2H), 2.10-2.30 (m, 3H), 2.84 (m, 1H), 3.50 (m, 2H), 5.12 (m, 1H), 6.62 (m, 1H), 6.86 (m, 2H), 7.08 (m, 2H), 7.18-7.32 (m, 5H), 7.46 (m, 1H), 7.62 (m, 1H).

Example 20

(S)-3-((S)-1-(4'-fluorobiphenyl-4-yl)ethyl)-6-(2-hydroxy-2-methylpropyl)-6-phenyl-1,3-oxazinan-2-one

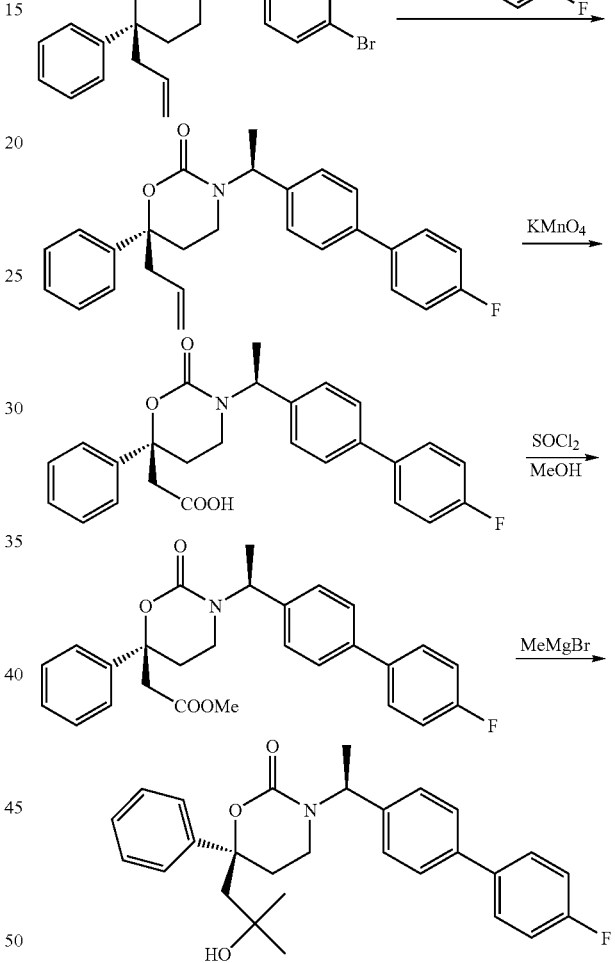

Step 1

A mixture of (R)-6-allyl-3-((S)-1-(4-bromophenyl)ethyl)-6-phenyl-1,3-oxazinan-2-one (5.83 g, 15 mmol), 4-fluorophenylboronic acid (3 g, 22 mmol), PdCl$_2$(PPh$_3$)$_2$ (1 g, 1.4 mmol), and aqueous Cs$_2$CO$_3$ solution (2 M, 8.0 mL) in 1,4-dioxane (50 mL) was heated to reflux for 2 h. The mixture was filtered, and the filtrate was extracted with EtOAc (3×). The combined organic layer was washed with brine, dried over Na$_2$SO$_4$ and concentrated to give the crude product, which was purified by preparative TLC to give (R)-6-allyl-3-((S)-1-(4'-fluorobiphenyl-4-yl)ethyl)-6-phenyl-1,3-oxazinan-2-one (5.3 g, 88%).

Step 2

To a solution of (R)-6-allyl-3-((S)-1-(4'-fluorobiphenyl-4-yl)ethyl)-6-phenyl-1,3-oxazinan-2-one (3 g, 7.23 mmol) in acetone (20 mL) was added a solution of KMnO₄ (685 mg, 4.34 mmol) and NaIO₄ (5.6 g, 26 mmol) in H₂O (15 mL) dropwise at 0° C. The mixture was stirred for 4 h. When TLC showed that the starting material had disappeared, the precipitate was removed by filtration, and the acetone was removed under reduced pressure. The resulting mixture was basified to pH=13 by the addition of 1 M aq NaOH, and then washed with ether (3×50 mL). The aqueous phase was acidified to pH=1 by addition of 1 N aq HCl, and extracted with CH₂Cl₂ (3×15 mL). The organic layers were combined, washed with brine, dried over Na₂SO₄ and concentrated in vacuo to give 2-((S)-3-((S)-1-(4'-fluorobiphenyl-4-yl)ethyl)-2-oxo-6-phenyl-1,3-oxazinan-6-yl)acetic acid (2.8 g, 90%).
Step 3

To a solution of 2-((S)-3-((S)-1-(4'-fluorobiphenyl-4-yl)ethyl)-2-oxo-6-phenyl-1,3-oxazinan-6-yl)acetic acid (1 g, 2.3 mmol) in MeOH (15 mL) was added thionyl chloride (408 mg, 3.5 mmol) dropwise at 0° C. under N₂ atmosphere. After refluxing overnight, the mixture was concentrated to give the crude product, which was purified by chromatography to give methyl 2-((S)-3-((S)-1-(4'-fluorobiphenyl-4-yl)ethyl)-2-oxo-6-phenyl-1,3-oxazinan-6-yl)acetate (680 mg, 68%).
Step 4

To a solution of methyl 2-((S)-3-((S)-1-(4'-fluorobiphenyl-4-yl)ethyl)-2-oxo-6-phenyl-1,3-oxazinan-6-yl)acetate (180 mg, 0.4 mmol) in dry THF (5 mL) under N₂ at −78° C. was added methylmagnesium bromide (1.5 mL, 3 M, 4.5 mmol) dropwise at −78° C. After addition, the mixture was stirred for 1 h at rt. Then the reaction was quenched with water and the mixture was extracted with ethyl acetate for three times (3×5 mL). The organic layers were combined, washed with brine, dried over Na₂SO₄, filtered and concentrated. The residue was purified by preparative HPLC to give (S)-3-((S)-1-(4'-fluorobiphenyl-4-yl)ethyl)-6-(2-hydroxy-2-methylpropyl)-6-phenyl-1,3-oxazinan-2-one (2.48 mg, 1%). ¹H NMR (CDCl₃): 1.05 (s, 1H), 1.13 (s, 3H), 1.50 (d, 3H), 2.14-2.23 (m, 2H), 2.25-2.40 (m, 1H), 2.80 (m, 1H), 5.63 (m, 1H), 6.94 (m, 2H), 7.02 (m, 2H), 7.18-7.30 (m, 7H), 7.38 (m, 2H). LC-MS Method 3 $t_R$=1.51, min, m/z=448, 470.

Example 21

5-(4-((S)-1-((R)-6-(4-fluorophenyl)-6-(3-hydroxypropyl)-2-oxo-1,3-oxazinan-3-yl)ethyl)phenyl)nicotinamide

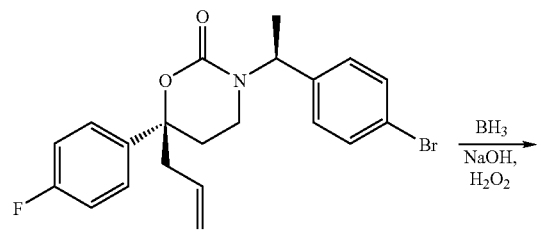

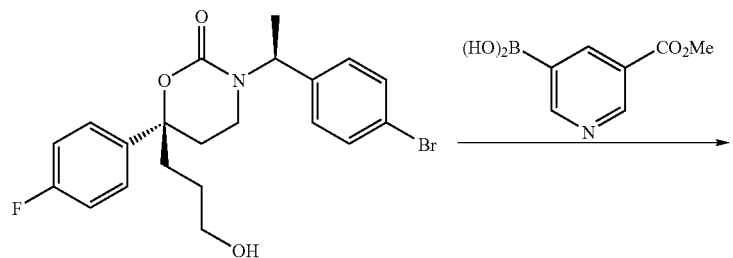

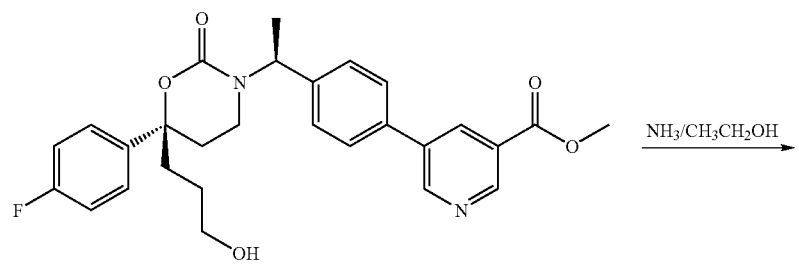

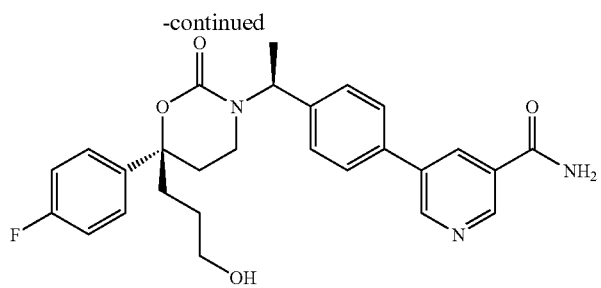

Step 1

To a solution of (R)-6-allyl-3-((S)-1-(4-bromophenyl)ethyl)-6-(4-fluorophenyl)-1,3-oxazinan-2-one (1 g, 2.4 mmol) in dry THF (15 mL) was added dropwise BH$_3$·THF (5 mL, 1 M) at 0° C. After stirring for 2 h at rt, the reaction mixture was cooled to 0° C. and water (1 mL), aqueous NaOH (0.5 mL, 3 M) and H$_2$O$_2$ (0.5 mL, 30%) were successively added. The mixture was stirred for 2-3 h at rt and diluted with water (8 mL). The pH was adjusted to 6-7 with 0.5 N HCl. The layers were separated, and the aqueous phase was extracted with EtOAc (3×10 mL). The combined organic layers were washed with a satd aq NaHCO$_3$ (20 mL) and brine (20 mL), dried over Na$_2$SO$_4$, and concentrated in vacuo to give the crude product, which was purified by preparative TLC to afford (R)-3-((S)-1-(4-bromophenyl)ethyl)-6-(4-fluorophenyl)-6-(3-hydroxypropyl)-1,3-oxazinan-2-one (400 mg, 38%).

Step 2

A mixture of (R)-3-((S)-1-(4-bromophenyl)ethyl)-6-(4-fluorophenyl)-6-(3-hydroxypropyl)-1,3-oxazinan-2-one (250 mg, 0.6 mmol), 5-(methoxycarbonyl)pyridin-3-ylboronic acid (163 mg, 0.9 mmol), PdCl$_2$(PPh$_3$)$_2$ (50 mg, 20%) and aqueous Cs$_2$CO$_3$ solution (2 M, 2 mL) in 1,4-dioxane (6 mL) was heated to reflux at 100° C. overnight under N$_2$. The mixture was filtered, and the filtrate was extracted with EtOAc for 3 times. The combined organic layer was washed with brine, dried over Na$_2$SO$_4$ and concentrated to the crude product, which was purified by preparative HPLC to give methyl 5-(4-((S)-1-((R)-6-(4-fluorophenyl)-6-(3-hydroxypropyl)-2-oxo-1,3-oxazinan-3-yl)ethyl)phenyl)nicotinate (220 mg, crude).

Step 3

Methyl 5-(4-((S)-1-((R)-6-(4-fluorophenyl)-6-(3-hydroxypropyl)-2-oxo-1,3-oxazinan-3-yl)ethyl)phenyl)nicotinate (30 mg, 0.1 mmol) was dissolved in anhydrous NH$_3$ in EtOH (5 mL). Then the mixture was stirred at rt overnight. The solvent was removed in vacuo to give the crude product, which was purified by preparative HPLC to provide 5-(4-((S)-1-((R)-6-(4-luorophenyl)-6-(3-hydroxypropyl)-2-oxo-1,3-oxazinan-3-yl)ethyl)phenyl)nicotinamide (10 mg, 34%). LC-MS Method 2 t$_R$=1.022 min, m/z=478; $^1$H NMR (CD$_3$OD): 1.31 (m, 1H), 1.56 (m, 3H), 1.59 (m, 1H), 1.91 (m, 2H), 2.17-2.28 (m, 1H), 2.33 (m, 1H), 2.44 (m, 1H), 3.14 (m, 1H), 3.44 (m, 2H), 5.60 (m, 1H), 7.04-7.17 (m, 4H), 7.29 (m, 2H), 7.49 (m, 2H), 8.41 (m, 1H), 8.86 (m, 1H), 8.97 (m, 1H).

Example 22

(S)-3-((S)-1-(4-bromophenyl)ethyl)-6-(2-hydroxy-2-methylpropyl)-6-phenyl-1,3-oxazinan-2-one

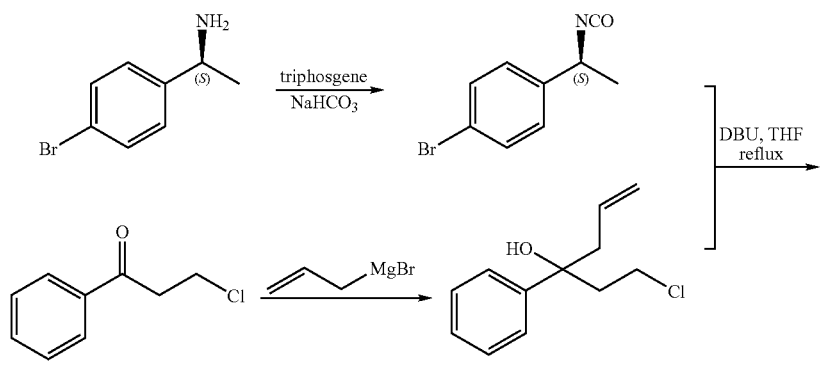

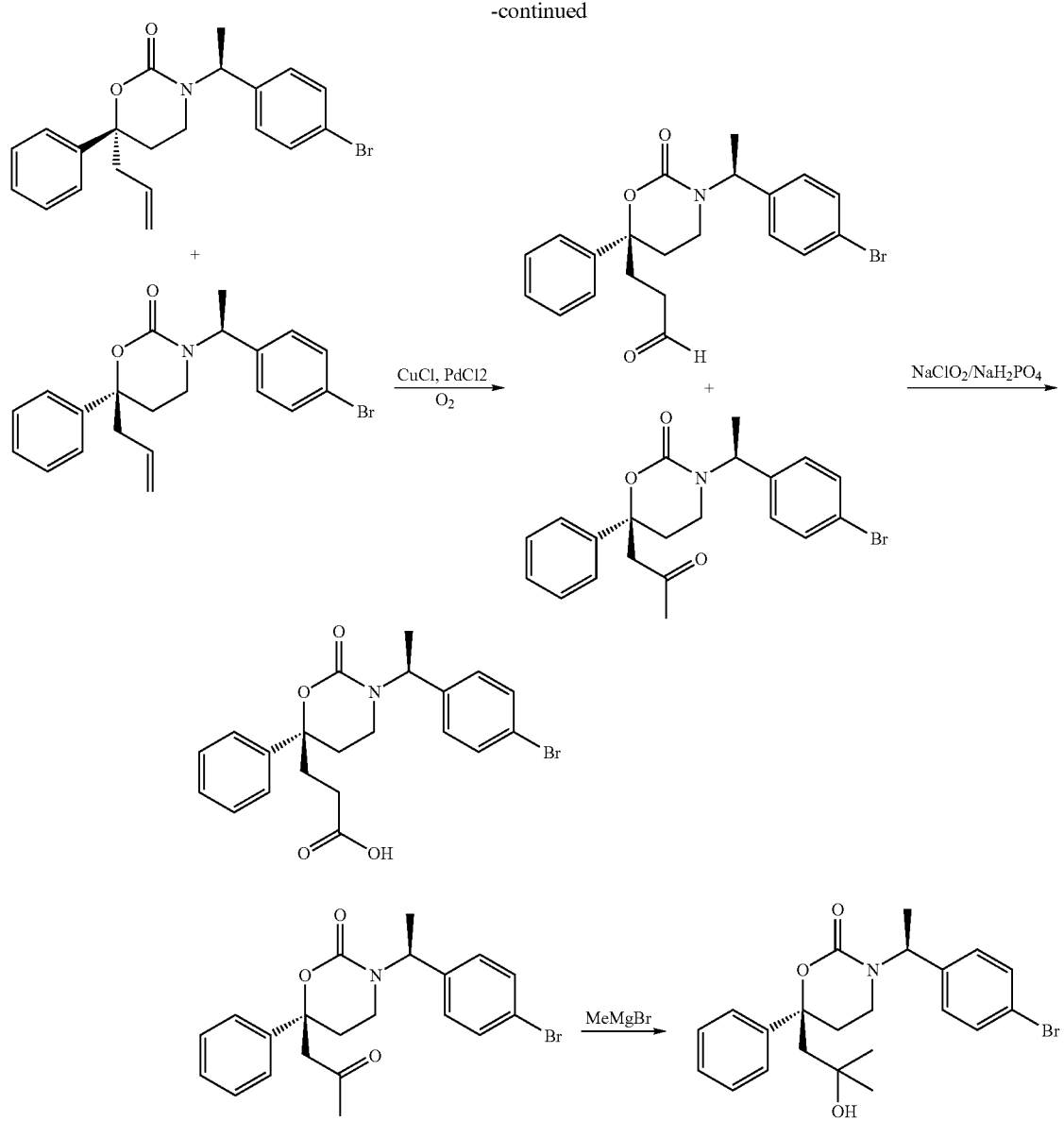

Step 1: (S)-1-bromo-4-(1-isocyanatoethyl)benzene

To a solution of (S)-1-(4-bromophenyl)ethanamine (240 g, 1.2 mol) in methylene chloride (3 L) and satd aq NaHCO$_3$ (3 L) solution was added triphosgene (118 g, 0.396 mol) at 0° C. The mixture was stirred for 15 min. The organic phase was separated, dried over Na$_2$SO$_4$ and concentrated to give 1-bromo-4-(1-isocyanato-ethyl)-benzene (170 g, 63%).

Step 2: 1-chloro-3-phenylhex-5-en-3-ol

To a solution of 3-chloro-1-phenylpropan-1-one (170 g, 1.01 mol) in anhydrous THF (1200 mL) was added allylmagnesium bromide (1.2 L, 1 mol/L) at −78° C. under nitrogen. The formed mixture was stirred for 30 min at −78° C. The reaction was quenched with aqueous NaHCO$_3$ solution. The organic phase was separated, dried over Na$_2$SO$_4$ and concentrated to give the crude product, which was purified by column chromatography (petroleum ether/EtOAc=100:1) to afford 1-chloro-3-phenylhex-5-en-3-ol (180 g, 86%). $^1$H NMR (CDCl$_3$): 2.27 (m, 2H), 2.51 (m, 1H), 2.74 (m, 1H), 3.22 (m, 1H), 3.58 (m, 1H), 5.16 (m, 2H), 5.53 (m, 1H), 7.23 (m, 1H), 7.39 (m, 4H).

Step 3: (R)-6-allyl-3-((S)-1-(4-bromophenyl)ethyl)-6-phenyl-1,3-oxazinan-2-one

A mixture of 1-chloro-3-phenyl-hex-5-en-3-ol (105 g, 0.050 mmol), (S)-(−)-1-(-bromophenyl)ethyl isocyanate (170 g, 0.752 mol), and DBU (228 g, 1.5 mol) in THF (1700 mL) was heated to reflux overnight. The mixture was diluted with EtOAc and washed with 1N aq HCl. The aqueous phase was extracted with EtOAc (3×). The combined organic phase was dried over Na$_2$SO$_4$. After the solvents were evaporated, the crude product was purified by column chromatography (petroleum ether/EtOAc=20:1 to 5:1) to give (R)-6-allyl-3-((S)-1-(4-bromophenyl)ethyl)-6-phenyl-1,3-oxazinan-2-one (100 g, 34%). $^1$H NMR (CDCl$_3$): 1.39 (d, 3H), 2.14 (m, 1H), 2.24 (m, 2H), 2.48-2.61 (m, 3H), 2.82 (m, 2H), 5.01 (m, 2H), 5.52 (q, 1H), 5.73 (m, 1H), 6.62 (d, 2H), 7.12 (m, 2H), 7.28 (m, 2H).

Step 4: (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal To a solution of (R)-6-allyl-3-((S)-1-(4-bromophenyl)ethyl)-6-phenyl-1,3-oxazinan-2-one (31 g, 78 mmol) and CuCl (19.3 g, 195 mmol) in dry DMF (150 mL) was added H₂O (50 mL) and PdCl₂ (4.10 g, 23 mmol) at rt. After addition, the mixture was stirred overnight under oxygen. After TLC showed the starting material had disappeared, the solid was filtered off. Water (200 mL) and EtOAc (200 mL) was added, the organic layers were separated and the aqueous layer was extracted with EtOAc (3×40 mL). The combined organic layer was washed with brine, dried over Na₂SO₄, filtered and concentrated to give a residue which was purified by column chromatography (petroleum ether/EtOAc=5:1 to 1:1) to give a mixture of (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal, (26 g, 81%).

Step 5: (S)-3-((S)-1-(4-bromophenyl)ethyl)-6-(2-oxopropyl)-6-phenyl-1,3-oxazinan-2-one To a mixture of (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal (20 g, 48.2 mmol) in t-BuOH (250 mL) and 2-methyl-2-butene (50 mL) was added a solution of NaClO₂ (19.3 g, 0.213 mol) and NaH₂PO₄ (28 g, 0.179 mol) in H₂O (300 mL) at 0° C. The formed mixture was stirred for 1 h at 0° C. The mixture was treated with water (100 mL) and extracted with CH₂Cl₂. The combined organic layer was dried over Na₂SO₄, filtered and concentrated to leave a residue, which was purified by column chromatography (petroleum ether/EtOAc=5:1 to 2.5:1) to afford (S)-3-((S)-1-(4-bromophenyl)ethyl)-6-(2-oxopropyl)-6-phenyl-1,3-oxazinan-2-one (10.0 g, 83%). ¹H NMR (CDCl₃): 1.49 (d, 3H), 2.12 (s, 3H), 2.33 (m, 2H), 2.63 (m, 1H), 2.86-3.08 (m, 3H), 5.57 (q, 1H), 6.66 (d, 2H), 7.19 (m, 2H), 7.33 (m, 5H).

Step 6: (S)-3-((S)-1-(4-bromophenyl)ethyl)-6-(2-hydroxy-2-methylpropyl)-6-phenyl-1,3-oxazinan-2-one To a solution of (S)-3-((S)-1-(4-bromophenyl)ethyl)-6-(2-oxopropyl)-6-phenyl-1,3-oxazinan-2-one (20 g, 46.4 mmol) in anhydrous THF (200 mL) was added dropwise methylmagnesium bromide (31 mL, 144 mmol) at −78° C. under nitrogen. Then the mixture was stirred at rt for 1 h. The reaction mixture was quenched with aq NaHCO₃ (50 mL) under ice water bath. The organic layers were separated. The aqueous layer was extracted with EtOAc (150 mL). The combined organic layers were washed with brine, dried over Na₂SO₄ and concentrated in vacuo to give the crude product, which was purified column chromatography (petroleum ether/EtOAc=5:1 to 2:1) to afford (S)-3-((S)-1-(4-bromophenyl)ethyl)-6-(2-hydroxy-2-methylpropyl)-6-phenyl-1,3-oxazinan-2-one (13 g, 65%). After re-crystallization from EtOH, 4 g of the pure compound was obtained. ¹H NMR (CDCl₃): 1.06 (s, 3H), 1.12 (s, 3H), 1.44 (d, 3H), 2.14 (m, 3H), 2.21 (m, 1H), 2.33 (m, 1H), 2.76 (m, 1H), 5.54 (q, 1H), 6.74 (d, 2H), 7.16 (d, 2H), 7.28 (m, 5H).

Example 23

Reverse Suzuki 6-(4-{1-[6-(2-Hydroxy-2-methyl-propyl)-2-oxo-6-phenyl-[1,3]oxazinan-3-yl]-ethyl}-phenyl)-N-methyl-nicotinamide

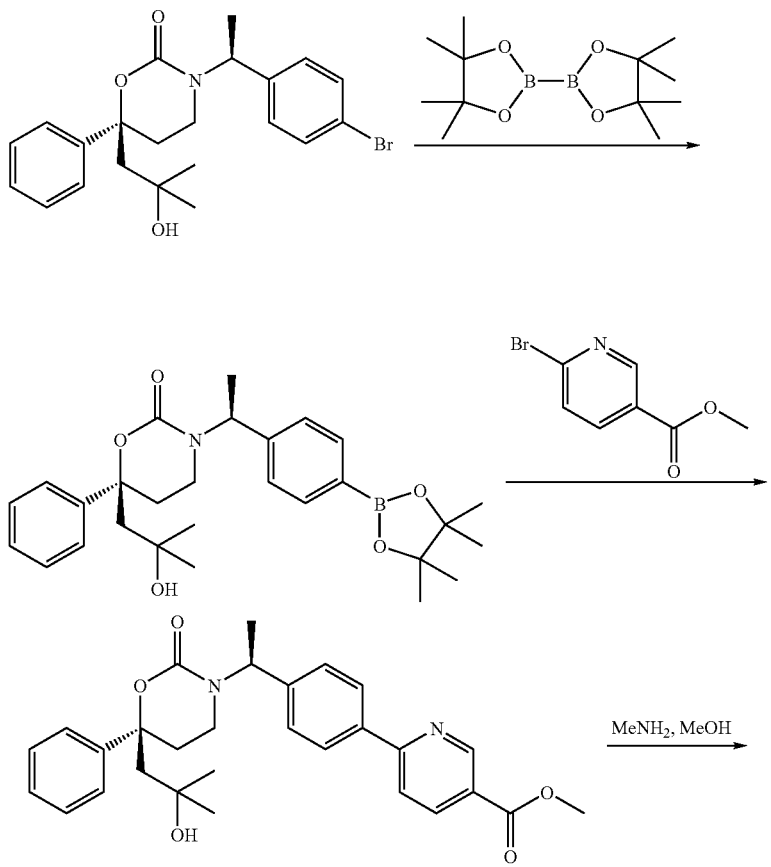

-continued

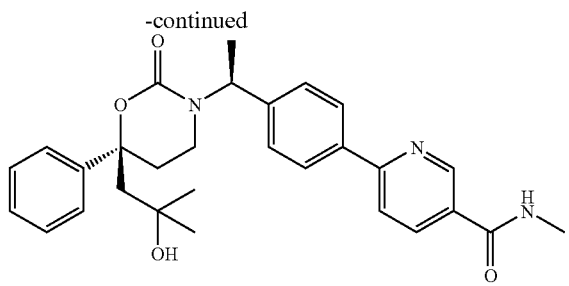

Step 1

To a solution of (S)-3-((S)-1-(4-bromophenyl)ethyl)-6-(2-hydroxy-2-methylpropyl)-6-phenyl-1,3-oxazinan-2-one (6.6 g, 15.2 mmol) and 4,4,4',4',5,5,5',5'-octamethyl-2,2'-bi(1,3,2-dioxaborolane) (6.1 g, 24.3 mmol) in dry DMSO (20 mL) was added KOAc (4.8 g, 48.6 mmol) and Pd(dppf)Cl$_2$ (372 mg, 0.46 mmol). After addition, the mixture was warmed to 100° C. for 20 h. After TLC showed the starting material had disappeared, the solid was filtered off. Water (60 mL) and EtOAc (20 mL) were added, the layers were separated and the aqueous layer was extracted with EtOAc (3×15 mL). The combined organic layer was washed with brine, dried over Na$_2$SO$_4$, filtered and concentrated to give (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (4.4 g, 60%), which was purified by column. NMR (CDCl$_3$): 1.03 (s, 3H), 1.12 (s, 3H), 1.22 (s, 12H), 1.49 (d, 3H), 2.13 (m, 4H), 2.26 (m, 1H), 2.73 (m, 1H), 5.64 (q, 1H), 6.91 (d, 2H), 7.38 (m, 5H), 7.51 (d, 2H).

Step 2

To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (500 mg, 1.04 mmol) and methyl 6-bromonicotinate (292 mg, 1.35 mmol) in dry 1,4-dioxane (5 mL) was added CsCO$_3$ (1 mL, 2 mmol) and Pd(PPh$_3$)$_2$Cl$_2$ (50 mg). After addition, the mixture was warmed to 110° C. for 30 min under microwave. After TLC showed the starting material had disappeared, the solid was filtered off. Water (20 mL) and EtOAc (10 mL) was added, the layers were separated and the aqueous layer was extracted with EtOAc (3×10 mL). The combined organic layer was washed with brine, dried over Na$_2$SO$_4$, filtered and concentrated to give methyl 6-(4-((S)-1-((S)-6-(2-hydroxy-2-methylpropyl)-2-oxo-6-phenyl-1,3-oxazinan-3-yl)ethyl)phenyl)nicotinate (507 mg, 89%), which was purified by preparative TLC. $^1$H NMR (CDCl$_3$): 1.13 (s, 3H), 1.19 (s, 3H), 1.61 (d, 3H), 2.24 (m, 4H), 2.37 (m, 1H), 2.88 (m, 1H), 4.02 (s, 3H), 5.76 (q, 1H), 7.11 (d, 2H), 7.29-7.47 (m, 6H), 7.78 (m, 1H), 7.82 (m, 2H), 8.38 (d, 1H), 9.31 (s, 1H).

Step 3

Methyl 6-(4-((S)-1-((S)-6-(2-hydroxy-2-methylpropyl)-2-oxo-6-phenyl-1,3-oxazinan-3-yl)ethyl)phenyl)nicotinate (150 mg, 0.307 mmol) was dissolved in NH$_2$Me/MeOH (10 mL). The mixture was stirred at rt overnight. The solvent was removed in vacuo to give the crude product, which was purified by preparative HPLC and chiral HPLC to afford 6-(4-((S)-1-((S)-6-(2-hydroxy-2-methylpropyl)-2-oxo-6-phenyl-1,3-oxazinan-3-yl)ethyl)phenyl)-N-methylnicotinamide (54 mg, 36%). LC-MS Method 2 t$_R$=1.117 min, m/z=430.1; $^1$H NMR (CD$_3$OD) 0.93 (s, 3H), 1.27 (s, 3H), 1.59 (d, 3H), 2.16 (s, 2H), 2.22-2.37 (m, 1H), 2.41-2.60 (m, 2H), 2.99 (s, 3H), 3.11 (m, 1H), 5.60 (m, 1H), 7.12 (d, 1H), 7.29 (m, 5H), 7.80 (m, 2H), 8.01 (d, 1H), 8.41 (d, 1H), 9.03 (s, 1H).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of preparing an oxazinone compound represented by the following structural formula:

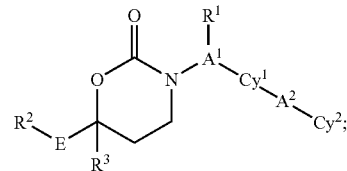

wherein:

R$^1$ is (a) absent or (b) is selected from (C$_1$-C$_6$)alkyl, (C$_2$-C$_6$)alkenyl, (C$_2$-C$_6$)alkynyl, optionally substituted (C$_1$-C$_3$)alkoxy(C$_1$-C$_3$)alkoxy, and (C$_1$-C$_3$)alkoxy(C$_1$-C$_3$) alkyl, each of which is optionally substituted with 1 to 4 groups independently selected from (C$_1$-C$_4$)alkyl, (C$_1$-C$_4$)alkoxy, (C$_1$-C$_4$)alkoxycarbonyl, benzyloxycarbonyl, hydroxy(C$_1$-C$_4$)alkyl, cyano(C$_1$-C$_4$)alkyl, (C$_1$-C$_4$) alkylamino, di(C$_1$-C$_4$)alkylamino, halogen, cyano, oxo, nitro, hydroxy, amino, MeSO$_2$—, MeSO$_2$N(Me)(C$_1$-C$_4$)alkyl, MeSO$_2$NH(C$_1$-C$_4$)alkyl, H$_2$NC(=O)CMe$_2$ (C$_1$-C$_4$)alkyl, H$_2$NC(=O)CHMe(C$_1$-C$_4$)alkyl, H$_2$NC (=O)CH$_2$(C$_1$-C$_4$)alkyl, —OR, —NR$_2$, —COOR, —CONR$_2$, and —SO$_k$R, wherein k is 0, 1 or 2, and wherein each R is independently —H, an alkyl group, a cycloalkyl group or an aryl group;

E is (a) a bond or (b) (C$_1$-C$_3$)alkylene or (C$_1$-C$_2$)alkoxy, wherein the O is attached to R$^2$, each of which is optionally substituted with 1 to 4 groups independently selected from methyl, ethyl, trifluoromethyl and oxo;

R$^2$ is selected from (C$_1$-C$_6$)alkyl, aryl, heteroaryl, cycloalkyl and heterocyclyl, each of which is optionally substituted with 1 to 4 groups independently selected from (C$_1$-C$_4$)alkyl, (C$_1$-C$_4$)alkoxy, (C$_1$-C$_4$)alkoxycarbonyl, benzyloxycarbonyl, protected hydroxy(C$_1$-C$_3$) alkyl hydroxy(C$_1$-C$_4$)alkyl cyano(C$_1$-C$_4$)alkyl (C$_1$-C$_4$) alkylamino di(C$_1$-C$_4$)alkylamino, halogen, cyano, oxo, nitro, hydroxy, amino, MeSO$_2$—, MeSO$_2$N(Me)(C$_1$-C$_4$)alkyl, MeSO$_2$NH(C$_1$-C$_4$)alkyl, protected CONH$_2$, protected carboxylic acid, H$_2$NC(=O)CMe$_2$(C$_1$-C$_4$) alkyl, H$_2$NC(=O)CHMe(C$_1$-C$_4$)alkyl, H$_2$NC(=O)

CH$_2$(C$_1$-C$_4$)alkyl, —OR, —NR$_2$, —COOR, —CONR$_2$, and —SO$_k$R, wherein k is 0, 1 or 2, and wherein each R is independently —H, an alkyl group, a cycloalkyl group or an aryl group;

R$^3$ is selected from (C$_1$-C$_6$)alkyl, (C$_2$-C$_6$)alkenyl, (C$_2$-C$_6$)alkynyl, (C$_3$-C$_5$)cycloalkyl(C$_1$-C$_4$)alkyl, (C$_1$-C$_3$)alkoxy (C$_1$-C$_3$)alkoxy and (C$_1$-C$_3$)alkoxy(C$_1$-C$_3$)alkyl, each of which is optionally substituted with 1 to 4 groups independently selected from (C$_1$-C$_4$)alkyl, (C$_1$-C$_4$)alkoxy, (C$_1$-C$_4$)alkoxycarbonyl, benzyloxycarbonyl, hydroxy (C$_1$-C$_4$)alkyl, protected hydroxy(C$_1$-C$_4$)alkyl, protected (C$_1$-C$_4$)alkylamino, cyano(C$_1$-C$_4$)alkyl, (C$_1$-C$_4$)alkylamino, di(C$_1$-C$_4$)alkylamino, halogen, cyano, oxo, protected hydroxy, protected amino, protected MeSO$_2$NH (C$_1$-C$_4$)alkyl, protected H$_2$NC(=O)CMe$_2$(C$_1$-C$_4$)alkyl, protected H$_2$NC(=O)CHMe(C$_1$-C$_4$)alkyl, protected H$_2$NC(=O)CH$_2$(C$_1$-C$_4$)alkyl, nitro, hydroxy, amino, MeSO$_2$—, MeSO$_2$N(Me)(C$_1$-C$_4$)alkyl, MeSO$_2$NH(C$_1$-C$_4$)alkyl, H$_2$NC(=O)CMe$_2$(C$_1$-C$_4$)alkyl, H$_2$NC(=O)CHMe(C$_1$-C$_4$)alkyl, H$_2$NC(=O)CH$_2$(C$_1$-C$_4$)alkyl, —OR, —NR$_2$, —COOR, —CONR$_2$, and —SO$_k$R, wherein k is 0, 1 or 2, and wherein each R is independently —H, an alkyl group, a cycloalkyl group or an aryl group;

A$^1$ is (a) a bond, or (b) (C$_1$-C$_3$)alkylene, CH$_2$CH$_2$O, wherein the oxygen is attached to Cy$^1$;

Cy$^1$ is aryl, heteroaryl, monocyclic cycloalkyl or monocyclic heterocyclyl, each of which is optionally substituted with 1 to 4 groups independently selected from (C$_1$-C$_4$) alkyl, (C$_1$-C$_4$)alkoxy, (C$_1$-C$_4$)alkoxycarbonyl, benzyloxycarbonyl, hydroxy(C$_1$-C$_4$)alkyl, cyano(C$_1$-C$_4$) alkyl, (C$_1$-C$_4$)alkylamino, di(C$_1$-C$_4$)alkylamino, halogen, cyano, oxo, nitro, protected hydroxy, protected amino, hydroxy, (C$_3$-C$_4$)cycloalkyl, (C$_3$-C$_4$)cycloalkyl (C$_1$-C$_2$)alkyl, protected CONH$_2$, protected (C$_1$-C$_4$) alkylaminocarbonyl, amino, protected (C$_3$-C$_4$)cycloalkylaminocarbonyl, {(C$_1$-C$_4$)alkyl}{(C$_3$-C$_4$) cycloalkyl}aminocarbonyl, protected (C$_1$-C$_4$) alkylcarbonylamino, MeSO$_2$—, MeSO$_2$N(Me)(C$_1$-C$_4$) alkyl, MeSO$_2$NH(C$_1$-C$_4$)alkyl, H$_2$NC(=O)CMe$_2$(C$_1$-C$_4$)alkyl, H$_2$NC(=O)CHMe(C$_1$-C$_4$)alkyl, H$_2$NC(=O) CH$_2$(C$_1$-C$_4$)alkyl, —OR, —NR$_2$, —COOR, —CONR$_2$, and SO$_k$R, wherein k is 0, 1 or 2, and wherein each R is independently —H, an alkyl group, a cycloalkyl group or an aryl group;

A$^2$ is (a) a bond, O, S or NR$^4$, wherein R$^4$ is (C$_1$-C$_3$)alkyl or (C$_3$-C$_6$)cycloalkyl; or (b) (C$_1$-C$_3$)alkylene or (C$_1$-C$_2$) alkoxy, each of which is optionally substituted with 1 to 4 groups independently selected from methyl, ethyl, and trifluoromethyl;

Cy$^2$ is (a) hydrogen or (b) aryl, heteroaryl, cycloalkyl or heterocyclyl, each of which is optionally substituted with 1 to 4 groups independently selected from (C$_1$-C$_4$) alkyl, (C$_1$-C$_4$)alkoxy, (C$_1$-C$_4$)alkoxycarbonyl, benzyloxycarbonyl, hydroxy(C$_1$-C$_4$)alkyl, cyano(C$_1$-C$_4$) alkyl, (C$_1$-C$_4$)alkylamino, di(C$_1$-C$_4$)alkylamino, halogen, cyano, oxo, nitro, protected hydroxy, protected amino, hydroxy, (C$_3$-C$_4$)cycloalkyl, (C$_3$-C$_4$)cycloalkyl (C$_1$-C$_2$)alkyl, protected CONH$_2$, protected (C$_1$-C$_4$) alkylaminocarbonyl, amino, protected (C$_3$-C$_4$)cycloalkylaminocarbonyl, {(C$_1$-C$_4$)alkyl}{(C$_3$-C$_4$) cycloalkyl}aminocarbonyl, protected (C$_1$-C$_4$) alkylcarbonylamino, MeSO$_2$—, MeSO$_2$N(Me)(C$_1$-C$_4$) alkyl, MeSO$_2$NH(C$_1$-C$_4$)alkyl, H$_2$NC(=O)CMe$_2$(C$_1$-C$_4$)alkyl, H$_2$NC(=O)CHMe(C$_1$-C$_4$)alkyl, H$_2$NC(=O) CH$_2$(C$_1$-C$_4$)alkyl, —OR, —NR$_2$, —COOR, —CONR$_2$, and —SO$_k$R, wherein k is 0, 1 or 2, and wherein each R is independently —H, an alkyl group, a cycloalkyl group or an aryl group;

said method comprising the step of reacting a β-haloalcohol compound represented by the following structural formula:

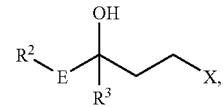

wherein X is a leaving group, with a isocyanate compound represented by the following structural formula:

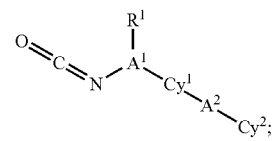

thereby forming the oxazinone compound.

2. The method of claim 1, wherein
R$^1$ is absent or is (C$_1$-C$_6$)alkyl;
A$^1$ is a bond, CH$_2$, or CH$_2$CH$_2$, or CH when R$^1$ is present;
A$^2$ is a bond, O, OCH$_2$CO or CH$_2$;
X is a Cl, Br, I or —OSO$_2$R, wherein R is (C$_1$-C$_4$)alkyl optionally substituted with one or more F, or phenyl optionally substituted with halogen, (C$_1$-C$_4$)alkyl or NO$_2$; and
E is a bond or (C$_1$-C$_3$)alkylene.

3. The method of claim 2, wherein
A$^1$ is a bond or CH when R$^1$ is present;
A$^2$ is a bond;
Cy$^2$ is hydrogen;
Cy$^1$ is phenyl substituted with Cl, Br, I or OSO$_2$CF$_3$, and optionally substituted with one or more additional substituents selected from (C$_1$-C$_4$)alkyl, (C$_1$-C$_4$)alkoxy, (C$_1$-C$_4$)alkoxycarbonyl, benzyloxycarbonyl, hydroxy (C$_1$-C$_4$)alkyl, cyano(C$_1$-C$_4$)alkyl, (C$_1$-C$_4$)alkylamino, di(C$_1$-C$_4$)alkylamino, halogen, cyano, oxo, nitro, hydroxy, amino, MeSO$_2$—, MeSO$_2$N(Me)(C$_1$-C$_4$) alkyl, MeSO$_2$NH(C$_1$-C$_4$)alkyl, H$_2$NC(=O)CMe$_2$(C$_1$-C$_4$)alkyl, H$_2$NC(=O)CHMe(C$_1$-C$_4$)alkyl, H$_2$NC(=O) CH$_2$(C$_1$-C$_4$)alkyl, —OR, —NR$_2$, —COOR, —CONR$_2$, and —SO$_k$R, wherein k is 0, 1 or 2, and wherein each R is independently —H, an alkyl group, a cycloalkyl group or an aryl group.

4. The method of claim 3, wherein the isocyanate compound is represented by the following structural formula:

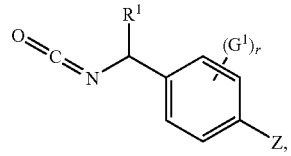

wherein
Z is a Cl, Br, I, OSO$_2$CF$_3$, OSO$_2$Me, or OSO$_2$C$_6$H$_4$Me;
r is 0, 1, 2 or 3; and each $G^1$ is independently selected from the group consisting of $(C_1$-$C_4)$alkyl, halo$(C_1$-$C_4)$alkyl, $(C_1$-$C_4)$alkoxy, halogen, cyano and nitro.

5. The method of claim 4, wherein:

$R^1$ is methyl or ethyl;

$R^2$ is phenyl, thienyl, or pyridyl, each optionally substituted with halogen, nitro, cyano, $(C_1$-$C_6)$alkyl, protected hydroxy$(C_1$-$C_3)$alkyl, $(C_1$-$C_3)$alkoxy, protected $CONH_2$, protected carboxylic acid and $SO_2Me$; and $R^3$ is methyl, ethyl, propyl, butyl, vinyl, allyl, 2-methyl-2-propenyl, or ethoxyethyl each optionally substituted with up to two groups independently selected from $(C_1$-$C_4)$alkyl $(C_1$-$C_4)$alkoxy, $(C_1$-$C_4)$alkoxycarbonyl, benzyloxycarbonyl, protected hydroxy$(C_1$-$C_4)$alkyl, cyano $(C_1$-$C_4)$alkyl, protected $(C_1$-$C_4)$alkylamino, di$(C_1$-$C_4)$alkylamino, halogen, cyano, oxo, nitro, protected hydroxy, protected amino, $MeSO_2$—, $MeSO_2N(Me)(C_1$-$C_4)$alkyl, protected $MeSO_2NH(C_1$-$C_4)$alkyl, protected $H_2NC(=O)CMe_2(C_1$-$C_4)$alkyl, protected $H_2NC(=O)CHMe(C_1$-$C_4)$alkyl and protected $H_2NC(=O)CH_2(C_1$-$C_4)$alkyl.

6. The method of claim 5, wherein $R^3$ is vinyl, allyl, 2-methyl-2-propenyl, $MeSO_2NHCH_2CH_2CH_2$, protected $H_2NC(=O)CH_2CH_2$, protected $H_2NC(=O)CMe_2CH_2$, 2-cyano-2-methylpropyl, 2-oxopropyl or $(C_1$-$C_4)$alkoxycarbonylmethyl.

7. The method of claim 6, wherein $R^2$ is phenyl optionally substituted with 1, 2 or 3 substituents selected from halo, cyano, protected $CONH_2$, $(C_1$-$C_4)$alkyl, $(C_1$-$C_4)$alkoxy and $SO_2Me$; and $R^3$ is allyl, 2-methyl-2-propenyl, protected $H_2NC(=O)CMe_2CH_2$ or 2-cyano-2-methylpropyl.

8. The method of claim 7, wherein $R^2$ is phenyl or fluorophenyl and $R^3$ is 2-methyl-2-propenyl, or 2-cyano-2-methylpropyl.

9. The method of claim 2, wherein:

$R^1$ is methyl or ethyl;

$R^2$ is phenyl, thienyl, or pyridyl, each optionally substituted with halogen, nitro, cyano, $(C_1$-$C_6)$alkyl, protected hydroxy$(C_1$-$C_3)$alkyl, $(C_1$-$C_3)$alkoxy, protected $CONH_2$, protected carboxylic acid and $SO_2Me$;

$R^3$ is methyl, ethyl, propyl, butyl, vinyl, allyl, 2-methyl-2-propenyl, or ethoxyethyl each optionally substituted with up to two groups independently selected from $(C_1$-$C_4)$alkyl, $(C_1$-$C_4)$alkoxy, $(C_1$-$C_4)$alkoxycarbonyl, benzyloxycarbonyl, protected hydroxy$(C_1$-$C_4)$alkyl, cyano $(C_1$-$C_4)$alkyl, protected $(C_1$-$C_4)$alkylamino, di$(C_1$-$C_4)$alkylamino, halogen, cyano, oxo, nitro, protected hydroxy, protected amino, $MeSO_2$—, $MeSO_2N(Me)(C_1$-$C_4)$alkyl, protected $MeSO_2NH(C_1$-$C_4)$alkyl, protected $H_2NC(=O)CMe_2(C_1$-$C_4)$alkyl, protected $H_2NC(=O)CHMe(C_1$-$C_4)$alkyl and protected $H_2NC(=O)CH_2(C_1$-$C_4)$alkyl;

$Cy^1$ is phenyl, cyclopropyl, cyclohexyl, pyrrolidinyl, piperidinyl, azepanyl, pyridyl, thiazolyl, pyrimidinyl, each optionally substituted with 1 to 4 groups independently selected from $(C_1$-$C_4)$alkyl, $(C_1$-$C_4)$alkoxy, $(C_1$-$C_4)$alkoxycarbonyl, benzyloxycarbonyl, hydroxy$(C_1$-$C_4)$alkyl, cyano$(C_1$-$C_4)$alkyl, $(C_1$-$C_4)$alkylamino, di$(C_1$-$C_4)$alkylamino, halogen, cyano, oxo, nitro, hydroxy, amino, $MeSO_2$—, $MeSO_2N(Me)(C_1$-$C_4)$alkyl, $MeSO_2NH(C_1$-$C_4)$alkyl, $H_2NC(=O)CMe_2(C_1$-$C_4)$alkyl, $H_2NC(=O)CHMe(C_1$-$C_4)$alkyl, $H_2NC(=O)CH_2(C_1$-$C_4)$alkyl, —OR, —$NR_2$, —COOR, —$CONR_2$, and —$SO_kR$, wherein k is 0, 1 or 2, and wherein each R is independently —H, an alkyl group, a cycloalkyl group or an aryl group; and $Cy^2$ is phenyl, thienyl, pyridyl, cyclopropyl, piperidinyl, piperazinyl, morpholinyl, thiazolyl, oxadiazolyl, thiadiazolyl, pyrazolyl, S,S-dioxothiazinyl, pyridazinyl, pyrimidinyl, pyrazinyl, benzimidazolyl, benztriazolyl, oxodihydropyridyl, oxodihydropyridazinyl, oxodihydropyrimidinyl and oxodihydropyrazinyl, each optionally substituted with 1 to 4 groups independently selected from $(C_1$-$C_4)$alkyl, $(C_1$-$C_4)$alkoxy, $(C_1$-$C_4)$alkoxycarbonyl, benzyloxycarbonyl, hydroxy$(C_1$-$C_4)$alkyl, cyano$(C_1$-$C_4)$alkyl, $(C_1$-$C_4)$alkylamino, di$(C_1$-$C_4)$alkylamino, halogen, cyano, oxo, nitro, hydroxy, amino, $MeSO_2$—, $MeSO_2N(Me)(C_1$-$C_4)$alkyl, $MeSO_2NH(C_1$-$C_4)$alkyl, $H_2NC(=O)CMe_2(C_1$-$C_4)$alkyl, $H_2NC(=O)CHMe(C_1$-$C_4)$alkyl, protected hydroxy, protected amino, protected $CONH_2$, protected $(C_1$-$C_4)$alkylaminocarbonyl, di$(C_1$-$C_4)$alkylaminocarbonyl, protected $(C_3$-$C_4)$cycloalkylaminocarbonyl, $\{(C_1$-$C_4)$alkyl$\}\{(C_3$-$C_4)$cycloalkyl$\}$aminocarbonyl, protected $(C_1$-$C_4)$alkylcarbonylamino $H_2NC(=O)CH_2(C_1$-$C_4)$alkyl, —OR, —$NR_2$, —COOR, —$CONR_2$, and —$SO_kR$, wherein k is 0, 1 or 2, and wherein each R is independently —H, an alkyl group, a cycloalkyl group or an aryl group; wherein substituents for a ring carbon atom of $Cy^1$ and $Cy^2$ are independently selected from halogen, cyano, oxo, nitro, protected hydroxy, protected amino, $(C_1$-$C_4)$alkyl, $(C_3$-$C_4)$cycloalkyl, $(C_3$-$C_4)$cycloalkyl$(C_1$-$C_2)$alkyl, $(C_1$-$C_4)$alkoxy, $(C_1$-$C_4)$alkoxycarbonyl, benzoxycarbonyl, protected $CONH_2$, protected $(C_1$-$C_4)$alkylaminocarbonyl, di$(C_1$-$C_4)$alkylaminocarbonyl, protected $(C_3$-$C_4)$cycloalkylaminocarbonyl, $\{(C_1$-$C_4)$alkyl$\}\{(C_3$-$C_4)$cycloalkyl$\}$aminocarbonyl and protected $(C_1$-$C_4)$alkylcarbonylamino, wherein suitable substituents for a substitutable ring nitrogen atom in $Cy^2$ are selected from the group consisting of $(C_1$-$C_4)$alkyl, $(C_3$-$C_4)$cycloalkyl, $(C_3$-$C_4)$cycloalkyl$(C_1$-$C_2)$alkyl, $(C_1$-$C_4)$alkoxycarbonyl, $(C_1$-$C_4)$alkylcarbonyl and benzyloxycarbonyl; wherein each substitutable ring nitrogen atom of $Cy^2$, if present, is either bonded to $A^2$, protected or substituted.

10. The method of claim 9, wherein $Cy^2$ is selected from the group consisting of benzimidazolyl, benzotriazolyl, oxodihydropyridyl, oxodihydropyridazinyl, oxodihydropyrimidinyl, oxodihydropyrazinyl, piperidinyl, pyridinyl, pyridazinyl, pyrimidinyl, pyrazinyl, pyrazolyl, thiazolyl and thiadiazolyl, each of which is optionally substituted with 1 to 4 groups independently selected from $(C_1$-$C_4)$alkyl, $(C_1$-$C_4)$alkoxy, $(C_1$-$C_4)$alkoxycarbonyl, benzyloxycarbonyl, hydroxy$(C_1$-$C_4)$alkyl, cyano$(C_1$-$C_4)$alkyl, $(C_1$-$C_4)$alkylamino, di$(C_1$-$C_4)$alkylamino, halogen, cyano, oxo, nitro, hydroxy, amino, $MeSO_2$—, $MeSO_2N(Me)(C_1$-$C_4)$alkyl, $MeSO_2NH(C_1$-$C_4)$alkyl, $H_2NC(=O)CMe_2(C_1$-$C_4)$alkyl, $H_2NC(=O)CHMe(C_1$-$C_4)$alkyl, $H_2NC(=O)CH_2(C_1$-$C_4)$alkyl, —OR, —$NR_2$, —COOR, —$CONR_2$, and —$SO_kR$, wherein k is 0, 1 or 2, and wherein each R is independently —H, an alkyl group, a cycloalkyl group or an aryl group;

$R^2$ is phenyl optionally substituted with 1, 2 or 3 substituents selected from halo, cyano, protected $CONH_2$, $(C_1$-$C_4)$alkyl, $(C_1$-$C_4)$alkoxy and $SO_2Me$; and $R^3$ is vinyl, allyl, 2-methyl-2-propenyl, $MeSO_2NHCH_2CH_2CH_2$, protected $H_2NC(=O)CH_2CH_2$, protected $H_2NC(=O)CMe_2CH_2$, 2-cyano-2-methylpropyl, 2-oxopropyl or $(C_1$-$C_4)$alkoxycarbonylmethyl.

11. The method of claim 10, wherein $R^3$ is allyl, 2-methyl-2-propenyl, protected $H_2NC(=O)CMe_2CH_2$ or 2-cyano-2-methylpropyl.

12. The method of claim 11, wherein $R^2$ is phenyl or fluorophenyl;
$R^3$ is 2-methyl-2-propenyl, or 2-cyano-2-methylpropyl; and
suitable substituents for a substitutable ring nitrogen atom in the group represented by $Cy^2$ are selected from the group consisting of $(C_1-C_4)$alkyl, $(C_3-C_4)$cycloalkyl, $(C_3-C_4)$cycloalkyl$(C_1-C_2)$alkyl, $(C_1-C_4)$alkoxycarbonyl and $(C_1-C_4)$alkylcarbonyl; and suitable substituents for a substitutable ring carbon atom in the $Cy^2$ are selected from the group consisting fluorine, chlorine, cyano, protected hydroxy, protected amino, $(C_1-C_4)$alkyl, $(C_3-C_4)$cycloalkyl, $(C_3-C_4)$cycloalkyl$(C_1-C_2)$alkyl, $(C_1-C_4)$alkoxy, protected $CONH_2$, protected $(C_1-C_4)$alkylaminocarbonyl, di$(C_1-C_4)$alkylaminocarbonyl, protected $(C_3-C_4)$cycloalkylaminocarbonyl, $\{(C_1-C_4)$alkyl$\}\{(C_3-C_4)$cycloalkyl$\}$aminocarbonyl and protected $(C_1-C_4)$alkylcarbonylamino.

13. The method of claim 1, wherein the β-haloalcohol compound is represented by the following structural formula:

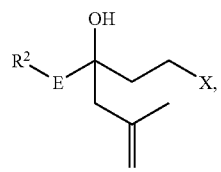

thereby forming a 2-methyl-2-propenyl intermediate represented by the following structural formula:

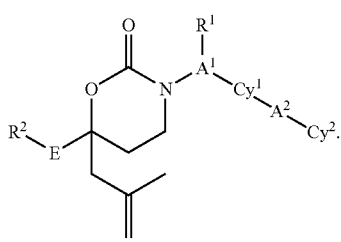

14. The method of claim 1, wherein the β-haloalcohol compound is represented by the following structural formula:

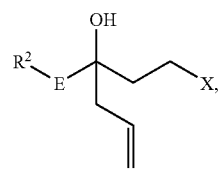

thereby forming a 2-propenyl intermediate represented by the following structural formula:

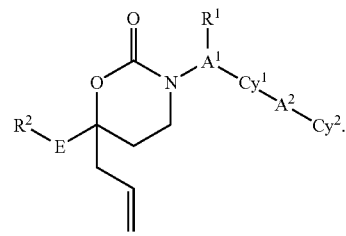

15. The method of claim 1 wherein the reaction between the isocyanate and the β-haloalcohol occurs in the presence of a base.

16. The method of claim 15, wherein the base is a non-nucleophilic amine base.

17. The method of claim 16, wherein the base 1,8-diazabicyclo[5.4.0]undec-7-ene.

* * * * *